US012734194B2

(12) United States Patent
McCully et al.

(10) Patent No.: US 12,734,194 B2
(45) Date of Patent: Sep. 15, 2026

(54) PROPHYLACTIC AND THERAPEUTIC USE OF MITOCHONDRIA AND COMBINED MITOCHONDRIAL AGENTS

(71) Applicant: Children's Medical Center Corporation, Boston, MA (US)

(72) Inventors: James D. McCully, Marblehead, MA (US); Pedro J. del Nido, Lexington, MA (US)

(73) Assignee: Children's Medical Center Corporation, Boston, MA (US)

( * ) Notice: Subject to any disclaimer, the term of this patent is extended or adjusted under 35 U.S.C. 154(b) by 904 days.

(21) Appl. No.: 17/607,975

(22) PCT Filed: Oct. 30, 2019

(86) PCT No.: PCT/US2019/058924
§ 371 (c)(1),
(2) Date: Nov. 1, 2021

(87) PCT Pub. No.: WO2020/222866
PCT Pub. Date: Nov. 5, 2020

(65) Prior Publication Data

US 2022/0347212 A1 Nov. 3, 2022

Related U.S. Application Data

(60) Provisional application No. 62/842,320, filed on May 2, 2019.

(51) Int. Cl.

| | |
|---|---|
| ***A61K 35/12*** | (2015.01) |
| ***A61B 6/50*** | (2024.01) |
| ***A61K 9/00*** | (2006.01) |
| ***A61P 9/10*** | (2006.01) |

(52) U.S. Cl.
CPC .............. *A61K 35/12* (2013.01); *A61B 6/504* (2013.01); *A61K 9/0019* (2013.01); *A61P 9/10* (2018.01)

(58) Field of Classification Search
CPC ...... A61K 35/12; A61K 9/0019; A61K 45/06; A61B 6/504; A61B 6/503; A61B 6/481; A61P 9/10; A61P 1/18; A61P 3/10; A61P 9/14; A61P 11/00; A61P 13/12; A61P 17/02; A61P 25/16
See application file for complete search history.

(56) References Cited

U.S. PATENT DOCUMENTS

| | | | |
|---|---|---|---|
| 2,561,043 | A | 7/1951 | Ayers |
| 2,854,143 | A | 9/1958 | Novak |
| 3,826,255 | A | 7/1974 | Diedrich et al. |
| 4,046,146 | A | 9/1977 | Rosskamp et al. |
| 4,253,468 | A | 3/1981 | Lehmbeck |
| 4,268,460 | A | 5/1981 | Boiarski et al. |
| 4,279,890 | A | 7/1981 | Harris et al. |
| 4,510,829 | A | 4/1985 | Kintzel et al. |
| 4,649,911 | A | 3/1987 | Knight et al. |
| 5,286,718 | A | 2/1994 | Elliott |
| 5,460,940 | A | 10/1995 | Yves et al. |
| 5,830,445 | A | 11/1998 | Bouillon et al. |
| 6,468,798 | B1 | 10/2002 | Debs et al. |
| 6,562,864 | B1 | 5/2003 | Larson |
| 6,693,086 | B1 | 2/2004 | Dow et al. |
| 6,695,227 | B1 | 2/2004 | Hayashi et al. |
| 6,777,227 | B2 | 8/2004 | Ricci et al. |
| 6,867,197 | B1 | 3/2005 | Davis et al. |
| 7,125,434 | B2 | 10/2006 | Yavorsky et al. |
| 7,279,326 | B2 | 10/2007 | Weissig et al. |
| 7,431,222 | B2 | 10/2008 | Monterrosa |
| 7,718,620 | B2 | 5/2010 | Szeto et al. |
| 7,745,651 | B2 | 6/2010 | Heyes et al. |
| 7,799,565 | B2 | 9/2010 | MacLachlan et al. |
| 7,803,397 | B2 | 9/2010 | Heyes et al. |
| 7,838,658 | B2 | 11/2010 | MacLachlan et al. |
| 7,901,708 | B2 | 3/2011 | MacLachlan et al. |
| 7,915,399 | B2 | 3/2011 | MacLachlan et al. |
| 7,923,984 | B2 | 4/2011 | Philbert |
| 7,982,027 | B2 | 7/2011 | MacLachlan et al. |
| 8,058,069 | B2 | 11/2011 | Yaworski et al. |
| 8,084,599 | B2 | 12/2011 | Rossie et al. |
| 8,101,741 | B2 | 1/2012 | MacLachlan et al. |
| 8,188,263 | B2 | 5/2012 | MacLachlan et al. |
| 8,236,943 | B2 | 8/2012 | Lee et al. |
| 8,283,333 | B2 | 10/2012 | Yaworski et al. |
| 8,349,809 | B2 | 1/2013 | Brown |
| 8,513,207 | B2 | 8/2013 | Brown |
| 8,616,195 | B2 | 12/2013 | Power et al. |

(Continued)

FOREIGN PATENT DOCUMENTS

| | | |
|---|---|---|
| AU | 2001013622 | 7/2001 |
| CA | 3049099 | 5/2018 |

(Continued)

OTHER PUBLICATIONS

Rana et al. (Perfusion, 2015, 30:94) (Year: 2015).*
AU Office Action in Australian Appln. No. 2021201217, dated Jan. 18, 2023, 4 pages.
Bayeva et al., "Mitochondria as a therapeutic target in heart failure," Journal of the American College of Cardiology, Feb. 12, 2013, 61(6):599-610.
CA Office Action in Canadian Appln. No. 3,011,472, dated Jan. 12, 2023, 5 pages.
CN Office Action in Chinese Appln. No. 2022111501695770, dated Nov. 18, 2022, 19 pages (with English translation).
EP European Search Report in European Appln. No. 20790601.7, dated Nov. 17, 2022, 12 pages.

(Continued)

*Primary Examiner* — David Steadman
*Assistant Examiner* — Joseph R Spangler
(74) *Attorney, Agent, or Firm* — Fish & Richardson P.C.

(57) ABSTRACT

The disclosure relates to compositions comprising isolated mitochondria or combined mitochondrial agents, and methods of treating or preventing disorders or damage associated with ischemia-reperfusion injury (IRI) using such compositions.

16 Claims, 49 Drawing Sheets

(56) References Cited

U.S. PATENT DOCUMENTS

| | | | |
|---|---|---|---|
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,315,773 | B2 | 4/2016 | Schiedner et al. |
| 10,370,458 | B2 | 8/2019 | McCully et al. |
| 11,491,480 | B2 | 11/2022 | McCully et al. |
| 11,903,974 | B2 | 2/2024 | Von Maltzahn et al. |
| 11,903,975 | B2 | 2/2024 | Von Maltzahn et al. |
| 2001/0047966 | A1 | 12/2001 | Colpan |
| 2002/0046410 | A1 | 4/2002 | Lanza et al. |
| 2004/0131641 | A1 | 7/2004 | Mikszta et al. |
| 2004/0161421 | A1 | 8/2004 | Komowski et al. |
| 2004/0171809 | A1 | 9/2004 | Korsmeyer |
| 2004/0192595 | A1 | 9/2004 | Murakami et al. |
| 2005/0224608 | A1 | 10/2005 | Khan et al. |
| 2007/0015777 | A1 | 1/2007 | Bush et al. |
| 2007/0128726 | A1 | 6/2007 | Koob et al. |
| 2008/0014144 | A1 | 1/2008 | Saltzman et al. |
| 2008/0260637 | A1 | 10/2008 | Dickman |
| 2008/0275005 | A1 | 11/2008 | Murphy |
| 2009/0202606 | A1 | 8/2009 | Kim et al. |
| 2011/0008310 | A1 | 1/2011 | Cataldo et al. |
| 2011/0130309 | A1 | 6/2011 | Cardone |
| 2011/0177051 | A1 | 7/2011 | Galski-Lorberboum |
| 2011/0313143 | A1 | 12/2011 | Martin et al. |
| 2011/0321200 | A1 | 12/2011 | Hyde et al. |
| 2012/0039810 | A1 | 2/2012 | Gorenstein et al. |
| 2012/0107285 | A1 | 5/2012 | Hyde et al. |
| 2012/0107937 | A1 | 5/2012 | Hyde et al. |
| 2012/0110683 | A1 | 5/2012 | Shomura et al. |
| 2012/0171716 | A1 | 7/2012 | Sun et al. |
| 2013/0022666 | A1 | 1/2013 | Brzezinska |
| 2013/0149778 | A1 | 6/2013 | Chang et al. |
| 2013/0217114 | A1 | 8/2013 | Yan et al. |
| 2013/0303436 | A1 | 11/2013 | Wilson |
| 2014/0051174 | A1 | 2/2014 | Burke et al. |
| 2014/0086886 | A1 | 3/2014 | Westenfelder |
| 2014/0106004 | A1 | 4/2014 | Wong et al. |
| 2014/0178993 | A1 | 6/2014 | Chang et al. |
| 2014/0193511 | A1 | 7/2014 | Yivgi-Ohana et al. |
| 2014/0314879 | A1 | 10/2014 | Lawendy et al. |
| 2015/0026833 | A1 | 1/2015 | Ande et al. |
| 2015/0079193 | A1 | 3/2015 | Yivgi-Ohana et al. |
| 2015/0344912 | A1 | 12/2015 | Kim et al. |
| 2016/0020823 | A1 | 1/2016 | Kuipers et al. |
| 2016/0138008 | A1 | 5/2016 | Doudna et al. |
| 2016/0208243 | A1 | 7/2016 | Zhang et al. |
| 2017/0120237 | A1 | 5/2017 | McCully et al. |
| 2017/0151287 | A1 | 6/2017 | Von Maltzahn et al. |
| 2017/0290763 | A1 | 10/2017 | Su |
| 2018/0057610 | A1 | 3/2018 | McCully et al. |
| 2018/0340022 | A1 | 11/2018 | Lee |
| 2019/0374582 | A1 | 12/2019 | Von Maltzahn et al. |
| 2020/0123273 | A1 | 4/2020 | McCully et al. |
| 2020/0306315 | A1 | 10/2020 | Von Maltzahn et al. |
| 2020/0306316 | A1 | 10/2020 | Von Maltzahn et al. |
| 2021/0023143 | A1 | 1/2021 | Yivgi-Ohana et al. |
| 2022/0160782 | A1 | 5/2022 | McCully |
| 2022/0267714 | A1 | 8/2022 | Ohta |
| 2022/0395531 | A1 | 12/2022 | McCully et al. |
| 2023/0183380 | A1 | 6/2023 | McCully et al. |
| 2023/0219081 | A1 | 7/2023 | McCully et al. |
| 2023/0416413 | A1 | 12/2023 | McCully et al. |

FOREIGN PATENT DOCUMENTS

| | | | |
|---|---|---|---|
| CN | 1187196 | | 7/1998 |
| CN | 1662548 | | 8/2005 |
| CN | 1832763 | | 9/2006 |
| CN | 101146826 | | 3/2008 |
| CN | 101693884 | | 4/2010 |
| CN | 104662011 | | 5/2015 |
| CN | 102791616 | | 7/2015 |
| CN | 107249600 | | 10/2017 |
| EP | 1519714 | A1 | 4/2005 |
| EP | 1664316 | A1 | 6/2006 |
| EP | 1766035 | | 3/2007 |
| EP | 1781593 | | 5/2007 |
| EP | 1519714 | | 10/2010 |
| EP | 1664316 | | 8/2012 |
| EP | 3402490 | | 11/2018 |
| JP | 2019507729 | A | 3/2019 |
| WO | WO 1988/007580 | | 10/1988 |
| WO | WO 2006/059329 | | 6/2006 |
| WO | WO 2008/137035 | | 11/2008 |
| WO | WO 2008/152626 | | 12/2008 |
| WO | WO 2012/085833 | | 6/2012 |
| WO | WO 2013/035101 | | 3/2013 |
| WO | WO 2013/171752 | | 11/2013 |
| WO | WO 2014/113638 | | 7/2014 |
| WO | WO 2015/192020 | | 12/2015 |
| WO | WO 2016/135723 | | 9/2016 |
| WO | WO 2017/095940 | | 6/2017 |
| WO | WO 2017/095944 | | 6/2017 |
| WO | WO 2017/095946 | | 6/2017 |
| WO | WO 2017/124037 | | 7/2017 |
| WO | WO 2020/214644 | A1 | 10/2020 |

OTHER PUBLICATIONS

EP Extended Search Report in European Appln. No. 19926810.3, dated Jan. 5, 2023, 11 pages.

EP Extended Search Report in European Appln. No. 20756733.0, dated Oct. 21, 2022, 12 pages.

EP Extended Search Report in European Appln. No. 20790601.7, dated Feb. 17, 2023, 10 pages.

EP Office Action in European Appln. No. 20155650.3, dated Dec. 6, 2022, 4 pages.

JP Japanese Office Action in Japanese Appln. No. 2020-173126, dated Nov. 1, 2022, 5 pages (with English translation).

McMurray et al., "Heart failure," Lancet, May 2005, 365:1877-89.

Roushandeh et al., "Mitochondrial transplantation as a potential and novel master key for treatment of various incurable diseases," Cytotechnology, Apr. 2019, 71(2):647-63.

Su et al., "Mitochondrial transplantation attenuates airway hyper-responsiveness by inhibition of cholinergic hyperactivity, " Theranostics, May 2016;6(8):1244-60.

Weixler et al., "Preventing Right Heart Failure in Pressure-Overload Hypertrophy through Transplantation of Autologous Mitochondria," The Thoracic and Cardiovascular Surgeon, Jan. 2019, 67(S 01):DGTHG-V116, 1 page.

CN Office Action in Chinese Appln. No. 201780013452.5, dated Jan. 31, 2023, 13 pages (with English translation).

CN Office Action in Chinese Appln. No. 201780013452.5, dated Jun. 21, 2023, 16 pages (with English translation).

JP Japanese Office Action in Japanese Appln. No. 2020-173126, dated Jul. 12, 2023, 5 pages (with English translation).

CA Office Action in Canadian Appln. No. 2,952,121, mailed on Oct. 31, 2023, 5 pages.

CA Office Action in Canadian Appln. No. 3,011,472, mailed on Aug. 29, 2023, 5 pages.

CA Office Action in Canadian Appln. No. 3,130,213, mailed on Nov. 2, 2023, 4 pages.

CN Office Action in Chinese Appln. No. 202080028568.8, mailed on Jul. 26, 2023, 14 pages (with English translation).

CN Office Action in Chinese Appln. No. 202080039304.2, mailed on Aug. 3, 2023, 16 pages (with English translation).

(56) References Cited

OTHER PUBLICATIONS

Deuse et al., "SCNT-derived ESCs with mismatched mitochondria trigger an immune response in allogeneic hosts, " Cell Stem Cell, Jan. 2015, 16(1):33-8.
EP Extended European Search Report in European Appln. No. 23179249.0, mailed on Nov. 30, 2023, 10 pages.
EP Office Action in European Appln. No. 20756733.0, mailed on Dec. 5, 2023, 10 pages.
EP Office Action in European Appln. No. 20790601.7, mailed on Oct. 11, 2023, 3 pages.
Hosseinian et al., "Prospects of mitochondrial transplantation in clinical medicine: Aspirations and challenges, " Mitochondrion, Jul. 2022, 65:33-44.
JP Office Action in Japanese Appln. No. 2022188165, mailed on Oct. 23, 2023, 8 pages (with English translation).
Kholmukhamedov et al., "Mitotracker probes and mitochondrial membrane potential," Shock, Jun. 2013, 39(6):543, 2 pages.
Piao et al., "Mitochondrial metabolic adaptation in right ventricular hypertrophy and failure, " Journal of Molecular Medicine, Oct. 2010, 88:1011-20.
RU Office Action in Russian Appln. No. 2021126922, mailed on Jul. 7, 2023, 11 pages (with English translation).
RU Office Action in Russian Appln. No. 2021126922, mailed on Nov. 14, 2023, 14 pages (with English translation).
Weixler et al., "Autogenous mitochondria transplantation for treatment of right heart failure," The Journal of Thoracic and Cardiovascular Surgery, Jul. 2021, 162(1):e111-21.
AU Office Action in Australian Appln. No. 2023200521, mailed on Feb. 9, 2024, 3 pages.
CN Office Action in Chinese Appln. No. 202080039304.2, mailed on Feb. 19, 2024, 12 pages (with English translation).
JP Office Action in Japanese Appln. No. 2021-547460, mailed on Dec. 22, 2023, 10 pages (with English translation).
kompas.com, "Dilated Cardiomyopathy," Keio University Hospital KOMPAS, Jan. 26, 2018, retrieved Jan. 17, 2024 from URL <https://kompas.hosp.keio.ac.jp/contents/000200.html>, 5 pages (with English translation).
medicalnote.jp, "About Pulmonary Heart Disease," Sep. 11, 2018, retrieved Dec. 12, 2023 from URL <https://medicalnote.jp/diseases/肺性心>, 3 pages (English translation).
twmu.jp, "Cardiac Enlargement and Cardiac Hypertrophy," Column, Adult Medical Center, Tokyo Women's Medical University, Jun. 1, 2012, retrieved Jan. 17, 2024 from URL <http://www.twmu.ac.jp/IOG/column/file32.html>, 3 pages (English translation).
tohoku.jp, "Elucidating the Mechanism of Pulmonary Hypertension Associated with Left Heart Failure—Identification of a Novel Drug Candidate for Heart Failure," Press Release, Graduate School of Medicine, Tohoku University, Jul. 10, 2018, retrieved Jan. 17, 2024 from URL <https://www.tohoku.ac.jp/japanese/newimg/pressimg/tohokuuniv-press20180710_Shimokawa180703_01web.pdf>, 12 pages (with English translation).
AU Office Action in Australian Appln. No. 2023201193, mailed on Apr. 29, 2024, 5 pages.
Averyanov et al., "Comparative effects of inhaled and intravenous mesenchymal stem cells in bleomycin-induced pulmonary fibrosis in rabbits," European Respiratory Journal, Jan. 2013, 42(57 supp).
Birmingham et al., "3' UTR seed matches, but not overall identity, are associated with RNAi off-targets," Nature Methods, Mar. 2006, 3(3):199-204.
Brand et al., "Assessing mitochondrial dysfunction in cells," Biochemical Journal, Apr. 2011, 435(2):297-312.
CN Office Action in Chinese Appln. No. 202080028568.8, mailed on Jun. 28, 2024, 19 pages (with English translation).
Edwards et al., "The remarkable flexibility of the human antibody repertoire; isolation of over one thousand different antibodies to a single protein, BLyS," Journal of Molecular Biology, Nov. 2003, 334(1):103-18.
Halim et al., "Aerosolised mesenchymal stem cells expressing angiopoietin-1 enhances airway repair," Stem Cell Reviews and Reports, Feb. 2019, 15:112-25.
Inagaki et al., "Epsilon protein kinase C as a potential therapeutic target for the ischemic heart," Cardiovascular Research, May 2006, 70(2):222-30.
JP Office Action in Japanese Appln. No. 2021-560961, mailed on Apr. 16, 2024, 8 pages (with English translation).
Kadenbach et al., "A second mechanism of respiratory control," FEBS Letters, Mar. 1999, 447(2-3):131-4.
Lloyd et al., "Modelling the human immune response: performance of a 1011 human antibody repertoire against a broad panel of therapeutically relevant antigens," Protein Engineering, Design & Selection, Mar. 2009, 22(3):159-68.
Slinde et al., "On the polydispersity of mitochondria in tissue homogenates and the determination of the average sedimentation coefficients of mixed populations of mitochondria," Analytical Biochemistry, Oct. 1978, 90(2):516-24.
Watano, "Introduction to the Feature Articles: Application of Aerosol to Medical Field—Recent Trend of Inhalation Therapy," Journal of Aerosol Research, Mar. 2006, 21(1):4, 3 pages (with English translation).
EP Office Action in European Appln. No. 19926810.3, mailed on Aug. 30, 2024, 8 pages.
Ahmad et al., "Mirol regulates intercellular mitochondrial transport & enhances mesenchymal stem cell rescue efficacy," The EMBO Journal, May 2, 2014, 33(9):994-1010.
Akurathi et al., "Preliminary Evaluation Of 18F-Rhodamine 6G As A Tumor-Imaging Agent," J Nucl Med, May 2013, 54 (Supplement 2): 1148, 2 pages.
Alfonzo et al., "Mitochondrial RNA import-the challenge to understand has just begun." Biol. Chem, Jun. 2009, 390(8):717-722.
Allen et al., Angiopellosis as an Alternative Mechanism of Cell Extravasation, Stem Cells, Jan. 2017, 35:170-180.
Altschul et al "Basic Local Alignment Search Tool," Journal of molecular biology, Oct. 5, 1990, 215(3):403-10.
Angsutararux et al., "Chemotherapy-Induced Cardiotoxicity: Overview of the Roles of Oxidative Stress," Oxid Med Cell Longev, Oct. 2015, 795602, 13 pages.
Arora et al., "Cell Culture Media: A Review" Mater Methods, Sep. 2013, 3(175):24, 1-21.
AU Office Action in Australian Application No. 2017208013, dated Nov. 16, 2021, 7 pages.
AU Office Action in Australian Appln. No. 2015274367, dated Oct. 8, 2020, 5 pages.
Augustin et al., "Characterization of peptides released from mitochondria: evidence for constant proteolysis and peptide efflux," Journal of Biological Chemistry, Jan. 28, 2005, 280(4):2691-9.
Bacman et al., "Specific elimination of mutant mitochondrial genomes in patient- derived cells by mitoTALENs," Nature Medicine, Sep. 2013, 19(9):1111-3.
Bansal et al., "Photocontrolled nanoparticle delivery systems for biomedical applications," Accounts of Chemical Research, Oct. 2014, 47(10), 3052-3060.
Barhoumi et al., "Ultraviolet light-mediated drug delivery: Principles, applications, and challenges, " Journal of Controlled Release, Dec. 2015, 219, 40 pages.
Bartel, "MicroRNAs: Genomics, Biogenesis, Mechanism, and Function," Cell, Jan. 23, 2004, 116:281-97.
Bartholomä et al., "18F-labeled rhodamines as potential myocardial perfusion agents: comparison of pharmacokinetic properties of several rhodamines," Nuclear Medicine and Biology, Oct. 1, 2015, 42(10):796-803.
Bartholomä et al., "Biological characterization of F18-labeled Rhodamine B, a potential positron emission tomography perfusion tracer," Nuclear Medicine and Biology, Nov. 1, 2013, 40(8):1043-8.
Bensley et al., "Studies on cell structure by the freezing-drying method VI. The preparation and properties of mitochondria," Anat Rec, Nov. 1934, 60:449-455.
Bershteyn et al., "Polymer-supported lipid shells, onions, and flowers," Soft Matter, Jan. 2008, 4(9):1787-91.
Birch-Machin et al., "An Evaluation of the Measurement of the Activities of Complexes I-IV in the Respiratory Chain of Human

(56) References Cited

OTHER PUBLICATIONS

Skeletal Muscle Mitochondria," Biochemical Medicine and Metabolic Biology, 51:35-42, Feb. 1994, 35-42.
Birsoy et al., "An Essential Role of the Mitochondrial Electron Transport Chain in Cell Proliferation Is to Enable Aspartate Synthesis," Cell, Jul. 2015, 162: 540-551.
Black et al., "Microarray and proteomic analysis of the cardioprotective effects of cold blood cardioplegia in the mature and aged male and female, " Physiological Genomics, Nov. 1, 2012, 44(21):1027-41.
Boezeman et al., "Systematic review of clinical applications of monitoring muscle tissue oxygenation with near-infrared spectroscopy in vascular disease," Microvasc Res, Mar. 2016, 104, 47 pages.
Boldogh et al., "Cell-Free Assays for Mitochondria-Cytoskeleton Interactions," Methods in Cell Biology, Jan. 1, 2007, 80:683-706.
Bolender et al., "Multiple pathways for sorting mitochondrial precursor proteins," EMBO Reports, Jan. 2008, 9(1):42-9.
Boudreau et al. (2014). Platelets release mitochondria serving as substrate for bactericidal group IIA-secreted phospholipase A2 to promote inflammation. Blood 124(14): 2173-2183.
Brown et al., "Mitochondrial function as a therapeutic target in heart failure," Nature Reviews Cardiology, Apr. 2017, 14(4):238-50.
CA Office Action in Canadian Appln. No. 2,952,121, dated Aug. 9, 2021, 4 pages.
Calvo et al., "MitoCarta2. 0: an updated inventory of mammalian mitochondrial proteins," Nucleic Acids Research, Jan. 4, 2016, 44(D1):D1251-7.
Cameron et al., "Development of therapeutics that induce mitochondrial biogenesis for the treatment of acute and chronic degenerative diseases," Journal of Medicinal Chemistry, Dec. 8, 2016, 59(23):10411-34.
Cannon et al., "Brown Adipose Tissue: Function and Physiological Significance," Physiol Rev, Jan. 2004, 84: 277-359.
Cavers et al., "Chondriosomes (mitochondria) and their significance," New Phytologist, Mar. 1, 1914, 13(3):96-106.
Cedikova et al., "Mitochondria in white, brown, and beige adipocytes," Stem cells international, 2016:1-11, Jan. 2016.
Chance et al., "A simple and rapid assay of oxidative phosphorylation," Nature, Jun. 1955, 175(4469):1120-1.
Chance, "The interaction of energy and electron transfer reactions in mitochondria: II. General properties of adenosine triphosphate-linked oxidation of cytochrome and reduction of pyridine nucleotide," Journal of Biological Chemistry, May 1, 1961, 236(5):1544-54.
Chang et al., "Treatment of human cells derived from MERRF syndrome by peptide-mediated mitochondrial delivery," Cytotherapy, Dec. 1, 2013, 15(12):1580-96.
Chattopadhyay et al., "T3 fails to restore mitochondrial thiol redox status altered by experimental hypothyroidism in rat testis," General and Comparative Endocrinology, Oct. 1, 2010, 169(1):39-47.
Chen et al., "Absolute quantification of matrix metabolites reveals the dynamics of mitochondrial metabolism," Cell, Aug. 2016, 166(5):1324-37.
Cheng et al., "Brief report: Mechanism of extravasation of infused stem cells," Stem Cells, 2012, 30: 2835-2842.
Choi et al., "Cardiac conduction through engineered tissue," The American Journal of Pathology, Jul. 1, 2006, 169(1):72-85.
Claude, "Fractionation Of Mammalian Liver Cells By Differential Centrifugation," J Exp Med, Apr. 1946, 84:61-89.
CN Office Action in Chinese Application No. 201580039651.4, dated Jul. 4, 2018, 9 pages (English translation).
CN Office Action in Chinese Application No. 201580039651.4, dated May 5, 2019, 9 pages (English translation).
CN Office Action in Chinese Appln. No. 201580039651.4, dated Aug. 17, 2020, 37 pages (with English translation).
CN Office Action in Chinese Appln. No. 201580039651.4, dated Jan. 21, 2021, 10 pages (with English translation).
CN Office Action in Chinese Appln. No. 201780013452.5, dated Nov. 19, 2021, 10 pages (with English translation).
Colman, "Effects of amino acid sequence changes on antibody-antigen interactions," Research in Immunology, Jan. 1, 1994, 145(1):33-6.
Cong et al., "Multiplex genome engineering using CRISPR/Cas systems," Science, Feb. 15, 2013, 339(6121):819-23.
Cowan et al., "Intracoronary delivery of mitochondria to the ischemic heart for cardioprotection." PloS one, Aug. 2016, 11(8): e0160889, 19 pages.
Cramer et al., "Methods for mycelial breakage and isolation of mitochondria and vacuoles of neurospora," Analytical Biochemistry, Feb. 1983, 128: 384-392.
Cypess et al., "Brown fat as a therapy for obesity and diabetes." Current Opinion in Endocrinology, Diabetes, and Obesity, Apr. 2010, 17: 143-149.
Dare et al., "The mitochondria-targeted anti-oxidant MitoQ decreases ischemia-reperfusion injury in a murine syngeneic heart transplant model," J Heart Lung Transplant, Nov. 2015, 34(11):1471-80.
Doench et al., "siRNAs can function as miRNAs," Genes & Development, Feb. 15, 2003, 17(4):438-42.
Doenst et al., "Cardiac metabolism in heart failure: implications beyond ATP production, " Circulation Research., Aug. 30, 2013, 113(6):709-24.
Dolezal et al., "Evolution of the molecular machines for protein import into mitochondria," Science, Jul. 21, 2006, 313(5785):314-8.
Doulamis et al., "Mitochondrial transplantation for myocardial protection in diabetic hearts," European Journal of Cardio-Thoracic Surgery, May 1, 2020, 57(5):836-45.
Ejsing et al., "Global analysis of the yeast lipidome by quantitative shotgun mass spectrometry," Proceedings of the National Academy of Sciences, Feb. 17, 2009, 106(7):2136-41.
Elliott et al., "Mitochondria organelle transplantation: introduction of normal epithelial mitochondria into human cancer cells inhibits proliferation and increases drug sensitivity," Breast Cancer Res. Treat., 2012, 136:347-354.
Emani et al., "Autologous mitochondrial transplantation for dysfunction after ischemia-reperfusion injury," The Journal of Thoracic and Cardiovascular Surgery, Jul. 1, 2017, 154(1):286-9.
EP European Search Report in European Appln. No. 20155650.3, dated Aug. 13, 2020, 15 pages.
EP European Search Report in European Appln. No. 20155650.3, dated Sep. 21, 2020, 17 pages.
EP Extended European Search Report in European Application No. 17739105.9 dated Jul. 8, 2019, 10 pages.
EP Extended European Search Report issued in European Patent Application No. 16871432.7, dated Jun. 4, 2019, 8 pages.
EP Extended European Search Report issued in European Patent Application No. 16871436.8, dated Jun. 4, 2019, 7 pages.
EP Office Action by European Appln. No. 20155650.3, dated Dec. 15, 2021, 5 pages.
EP Office Action in European Application No. 15733576.1, dated May 3, 2018, 5 pages.
EP Partial Supplementary European Search Report issued in European Patent Application No. 16871434.3, dated Jun. 4, 2019, 12 pages.
Ernster et al., "Mitochondria: a historical review," The Journal of Cell Biology, Dec. 1981, 91(3):227s-55s.
Facundo et al., "Mitochondrial ATP-sensitive K+ channels are redox-sensitive pathways that control reactive oxygen species production," ScienceDirect, Apr. 1, 2007, 42(7):1039-1048.
Faulk et al., "Magnesium cardioplegia enhances mRNA levels and the maximal velocity of cytochrome oxidase I in the senescent myocardium during global ischemia," Circulation, Nov. 1, 1995, 92(9):405-12.
Faulk et al., "Myocardial mitochondrial calcium accumulation modulates nuclear calcium accumulation and DNA fragmentation," The Annals of thoracic surgery, Aug. 1, 1995, 60(2):338-44.
Fernández-Vizarra et al., "Tissue-specific differences in mitochondrial activity and biogenesis," Mitochondrion, Jan. 1, 2011, 11(1):207-13.
Fernandez-Vizarra et al., "Isolation of mitochondria for biogenetical studies: An update," Mitochondrion, Apr. 2010, 10:253-262.
Finkel et al., "The ins and outs of mitochondrial calcium," Circulation Research, May 22, 2015, 116(11):1810-9.

(56) References Cited

OTHER PUBLICATIONS

Flaquer et al., "Mitochondrial genetic variants identified to be associated with posttraumatic stress disorder," Translational Psychiatry, Mar. 2015, 5(3):e524, 7 pages.
Frezza et al., "Organelle isolation: functional mitochondria from mouse liver, muscle and cultured filroblasts," Nature Protocols, 2007, 2(2): 287-295.
Friehs et al., "Pressure-overload hypertrophy of the developing heart reveals activation of divergent gene and protein pathways in the left and right ventricular myocardium," American Journal of Physiology-Heart and Circulatory Physiology, Mar. 1, 2013, 304(5):H697-708.
Geng et al., "Microfluidic electroporation for cellular analysis and delivery," Lab on a Chip, 2013, 13(19):3803-21.
Glancy et al., "Effect of calcium on the oxidative phosphorylation cascade in skeletal muscle mitochondria," Biochemistry, Apr. 23, 2013, 52(16):2793-809.
Gostimskaya et al., "Preparation of highly coupled rat heart mitochondria," Sep. 2010, J Vis Exp, 43: e2202, 4 pages.
Graham et al., "Isolation of Mitochondria from Tissues and UNIT 3.3 Cells by Differential Centrifugation," Current Protocol in Cell Biology, May 2001, 3(3.3), 15 pages.
Graham et al., "Isolation of nuclei and nuclear membranes from animal tissues," Current Protocols in Cell Biology, Oct. 2001, 12(1):3-10.
Gram et al., "Skeletal muscle mitochondrial H2O2 emission increases with immobilization and decreases after aerobic training in young and older men," The Journal of Physiology, Sep. 1, 2015, 593(17):4011-27.
Green et al., "Metabolic, enzymatic, and transporter responses in human muscle during three consecutive days of exercise and recovery," American Journal of Physiology-Regulatory, Integrative and Comparative Physiology, Oct. 2008, 295(4):R1238-50.
Grieve et al., "Microvascular obstruction by intracoronary delivery of mesenchymal stem cells and quantification of resulting myocardial infarction by cardiac magnetic resonance," Circulation: Heart Failure, May 2010, 3(3):e5-6, 3 pages.
Gross et al., "Isolation of functional mitochondria from rat kidney and skeletal muscle without manual homogenization," Anal Biochem, Nov. 2011, 418:213-223.
Guo et al., "Cardiovascular toxicities from systemic breast cancer therapy," Front Oncol, Dec. 4, 2014, 10 pages.
Hamilton, "The Mitochondria Mystery: Hidden risks for 'three-person' babies," Nature, Sep. 2015, 525(7570):444-6.
Han et al., "An unexpectedly labile mitochondrially encoded protein is required for Mta expression," Immunogenetics, Jul. 1989, 29: 258-264.
Hao et al., "Hydroxytyrosol promotes mitochondrial biogenesis and mitochondrial function in 3T3-LI adipocytes," The Journal of Nutritional Biochemistry, Jul. 1, 2010, 21(7):634-44.
Harms et al., "Brown and beige fat: development, function and therapeutic potential," Nature Medicine, Oct. 2013, 19: 1252-1263.
Hartwig et al., "A critical comparison between two classical and a kit-based method for mitochondria isolation," Proteomics, Jun. 2009, 9(11):3209-14.
Hendel et al., "Chemically modified guide RNAs enhance CRISPR-Cas genome editing in human primary cells," Nature Biotechnology, Sep. 2015, 33(9):985-9.
Herzog et al., "A novel informatics concept for high-throughput shotgun lipidomics based on the molecular fragmentation query language," Genome Biology, Jan. 2011, 12(1):1-25.
Herzog et al., "LipidXplorer: a software for consensual cross-platform lipidomics," PLoS One, PloS one, Jan. 17, 2012, 7(1):e29851, 7 pages.
Hoeper et al., "Mortality in pulmonary arterial hypertension: prediction by the 2015 European pulmonary hypertension guidelines risk stratification model," European Respiratory Journal, Aug. 1, 2017, 50(2), 10 pages.
Hogeboom et al., "Cytochemical studies of mammalian tissues; isolation of intact mitochondria from rat liver; some biochemical properties of mitochondria and submicroscopic particulate material," J Biol Chem, Feb. 1948, 172:619-635.
Ikon et al., "Exogenous cardiolipin localizes to mitochondria and prevents TAZ knockdown-induced apoptosis in myeloid progenitor cells," Biochem Biophys Res Commun, Aug. 2015, 464(2):580-5.
Islam et al., "Mitochondrial transfer from bone-marrow-derived stromal cells to pulmonary alveoli protects against acute lung injury," Nature Medicine, May 2012, 18: 759-765.
Jo et al., "Efficient mitochondrial genome editing by CRISPR/Cas9," BioMed Research International, Oct. 2015, vol. 2015.
JP Japanese Office Action in Japanese Appln. No. 2018-536875, dated Dec. 27, 2021, 15 pages (with English translation).
JP Office Action in Japanese Appln. No. 2017-517221, dated Mar. 19, 2019, 4 pages.
Kalogeris et al., "Cell biology of ischemia/reperfusion injury. International review of cell and molecular biology," Jan. 1, 2012, 298:229-317.
Kassab et al., "Morphometry of pig coronary arterial trees," American Journal of Physiology-Heart and Circulatory Physiology, Jul. 1, 1993, 265(1):H350-65.
Kaul et al., "Insulin resistance in type 1 diabetes mellitus," Metabolism, Dec. 2015, 64(12), 39 pages.
Kaza et al., "Myocardial rescue with autologous mitochondrial transplantation in a porcine model of ischemia/reperfusion," The Journal of Thoracic and Cardiovascular Surgery, Apr. 2017, 153(4), 934-943.
Keeney et al., "Mitochondrial gene therapy augments mitochondrial physiology in a Parkinson's disease cell model," Human Gene Therapy, Aug. 1, 2009, 20(8):897-907.
Kirby et al., "Biochemical assays of respiratory chain complex activity, " Methods in Cell Biology, Jan. 1, 2007, 80:93-119.
Kishida et al., "Reprogrammed Functional Brown Adipocytes Ameliorate Insulin Resistance and Dyslipidemia in Diet-Induced Obesity and Type 2 Diabetes," Stem Cell Reports, Oct. 2015, 5(4):569-81.
Kitani et al., "Internalization of isolated functional mitochondria: involvement of micropinocytosis," Journal of Cellular and Molecular Medicine, Aug. 2014, 18(8):1694-703.
Kornfeld et al., "Mitochondrial reactive oxygen species at the heart of the matter: new therapeutic approaches for cardiovascular diseases," Circulation Research, May 22, 2015, 116(11):1783-99.
Kunze et al., "The similarity between N-terminal targeting signals for protein import into different organelles and its evolutionary relevance," Frontiers in Physiology, Sep. 24, 2015, 6:259, 27 pages.
Kusminski et al., "Mitochondrial dysfunction in white adipose tissue," Trends in endocrinology & metabolism, 23(9):435-43, Sep. 2012.
Lang et al., "Recommendations for cardiac chamber quantification by echocardiography in adults: an update from the American Society of Echocardiography and the European Association of Cardiovascular Imaging," European Heart Journal—Cardiovascular Imaging, Mar. 1, 2015, 16(3):233-71.
Lau et al., "The 2015 ESC/ERS Guidelines for the diagnosis and treatment of pulmonary hypertension: a practical chronicle of progress," European Respiratory Journal, Oct. 1, 2015, 46(4):879-82.
Layland et al., "Adenosine: physiology, pharmacology, and clinical applications," JACC: Cardiovascular Interventions, Jun. 2014, 7(6):581-91.
Levitsky et al., "Mitochondrial DNA deletions in coronary artery bypass grafting patients," European Journal of Cardio-thoracic Surgery, Nov. 2003, 24: 777-784.
Lim et al., "Microarray analysis shows that some microRNAs downregulate large Nos. of target mRNAs," Nature, Feb. 2005, 433(7027):769-73.
Lim et al., "Cold-induced activation of brown adipose tissue and adipose angiogenesis in mice," Nature Protocols, Mar. 2012, 7: 606-615.
Lim et al., "Levosimendan Reduces Mortality in Adults with Left Ventricular Dysfunction Undergoing Cardiac Surgery: A Systematic Review and Meta-analysis," J Card Surg, Jul. 2015, 30(7):547-54.

(56) References Cited

OTHER PUBLICATIONS

Lin et al "Incorporation of VSV-G produces fusogenic plasma membrane vesicles capable of efficient transfer of bioactive macromolecules and mitochondria" Biomed Microdevices (2016) 18: 41.

Lin et al., "Isolated mitochondria infusion mitigates ischemia-reperfusion injury of the liver in rats," Shock, Mar. 2013, 39: 304-310.

Lin et al., "Human white adipose tissue vasculature contains endothelial colony-forming cells with robust in vivo vasculogenic potential," Angiogenesis, Oct. 2013, 16(4): 735-744.

Liu et al., "Disrupted Renal Mitochondrial Homeostasis after Liver Transplantation in Rats," PLoS One, Oct. 2015, 10(10):e0140906.

Maniataki et al., "Human mitochondrial tRNAMet is exported to the cytoplasm and associates with the Argonaute 2 protein. Rna," Jun. 1, 2005, 11(6):849-52.

Masuzawa et al., "Transplantation of autologously derived mitochondria protects the heart from ischemia-reperfusion injury," Amer J Physiol Heart Circ Physiol, Apr. 2013, 304:H966-H982.

Matsuda et al., "Developmental Differences in Cytosolic Calcium Accumulation Associated With Global Ischemia Evidence for Differential Intracellular Calcium Channel Receptor Activity," Circulation, Nov. 1997, 96(9 Supp):II-233-9.

McCully et al., "Injection of isolated mitochondria during early reperfusion for cardioprotection," American Journal of Physiology-Heart and Circulatory Physiology, Jan. 2009, 296: H94-H105.

McCully et al., "Abstract 2272: Mitochondrial Transplantation for Cardioprotection," Circulation, Oct. 2007, 116: II, 2 pages.

McCully et al., "Mitochondrial transplantation for therapeutic use," Clin. Trans. Med., Dec. 2016, 5:16, 13 pages.

McCully et al., "Adenosine-enhanced ischemic preconditioning: adenosine receptor involvement during ischemia and reperfusion," Am J Heart Cir Physiol, Feb. 2001, 280: H591-H602.

McCully et al., "Age-and Gender-Related Differences in Mitochondrial Oxygen Consumption and Calcium With Cardioplegia and Diazoxide," Ann Thorac Surg, Mar. 2007, 83: 1102-9.

MCully et al., "Diazoxide Amelioration of Myocardial Injury and Mitochondrial Damage During Cardiac Surgery," Ann Thorac Surg, Dec. 2002, 74: 2138-46.

Melero-Martin et al., "In vivo vasculogenic potential of human blood-derived endothelial progenitor cells," Blood, Jun. 2007, 109(11), 4761-4768.

Mercer et al., "Operating characteristics of some compressed-air nebulizers," American Industrial Hygiene Association Journal, Jan. 1, 1968, 29(1):66-78.

Millar et al. "Isolation and subfractionation of mitochondria from plants," Methods in cell biology, Jan. 1, 2001, 65:53-74.

Moskowitzova et al., "Mitochondrial transplantation prolongs cold ischemia time in murine heart transplantation," The Journal of Heart and Lung Transplantation, Jan. 1, 2019, 38(1):92, 25 pages.

Mumtaz et al., "Design of liposomes for circumventing the reticuloendothelial cells," Glycobiol, Nov. 1991, 1 (5): 505-510.

Néchad et al., "Development of brown fat cells in monolayer culture: I. Morphological and biochemical distinction from white fat cells in culture," Experimental Cell Research, Nov. 1, 1983, 149(1):105-18.

Neubauer, "The failing heart—an engine out of fuel," New England Journal of Medicine, Mar. 15, 2007, 356(11):1140-51.

Nishikawa et al., "Nonviral vectors in the new millennium: delivery barriers in gene transfer," Human Gene Therapy, May 20, 2001, 12(8):861-70.

Noly et al., "Right ventricular mitochondrial respiratory function in a piglet model of chronic pulmonary hypertension," The Journal of Thoracic and Cardiovascular Surgery, Jan. 1, 2020, 159(1):129-40.

Novak et al., "Preparation of subcellular fractions suitable for biochemical analyses from human subcutaneous adipose tissue obtained by needle biopsy—I. Isolation of mitochondria on a microscale," Experimental Cell Research, Aug. 1972, 73: 335-344.

Novobrantseva et al., "Systemic RNAi-mediated gene silencing in nonhuman primate and rodent myeloid cells," Molecular Therapy-Nucleic Acids, Jan. 1, 2012, 1:e4, 13 pages.

O'Connell et al., "The effects of cryopreservation on sperm morphology, motility and mitochondrial function, " Human Reproduction, Mar. 1, 2002, 17(3):704-9.

Olson et al., "Changes in endogenous substrates of isolated rabbit heart mitochondria during storage, " Journal of Biological Chemistry, Jan. 25, 1967, 242(2):325-32.

Orive et al., "Cell encapsulation: technical and clinical advances," Trends in Pharmacological Sciences, Aug. 1, 2015, 36(8):537-46.

Orme-Johnson, "Appendix 2. Direct and indirect inhibitors of mitochondrial ATP synthesis," Methods in Cell Biology, 2007, 80:813-26.

Pacak et al., "Actin-dependent mitochondrial internalization in cardiomyocytes: evidence for rescue of mitochondrial function," Biology Open, Jul. 2015, 4: 622-626.

Pacak et al., "Superparamagnetic iron oxide nanoparticles function as a long-term, multi-modal imaging label for non-invasive tracking of implanted progenitor cells," PLoS One, Sep. 24, 2014, 9(9):e108695.

Pallotti et al., "Isolation and subfractionation of mitochondria from animal cells and tissue culture lines," Methods in Cell Biology, Jan. 1, 2001, 65:1-35.

PCT International Preliminary Report on Patentability in International Application No. PCT/US2017/013564, dated Jul. 17, 2018, 14 pages.

PCT International Preliminary Report on Patentability in International Appln. No. PCT/US2019/058924, dated Nov. 2, 2021, 11 pages.

PCT International Preliminary Report on Patentability in International Appln. No. PCT/US2020/018371, dated Aug. 10, 2021, 12 pages.

PCT International Preliminary Report on Patentability in International Appln. No. PCT/US2020/028219, dated Sep. 28, 2021, 10 pages.

PCT International Search Report and Written Opinion in International Application No. PCT/US2015/035584, dated Sep. 2, 2015, 12 pages.

PCT International Search Report and Written Opinion in International Application No. PCT/US2016/064238, dated Apr. 13, 2017, 13 pages.

PCT International Search Report and Written Opinion in International Application No. PCT/US2016/064247 dated May 10, 2017, 16 pages.

PCT International Search Report and Written Opinion in International Application No. PCT/US2016/064251 dated May 8, 2017, 15 pages.

PCT International Search Report and Written Opinion in International Application No. PCT/US2017/013564, dated Jun. 5, 2017, 12 pages.

PCT International Search Report and Written Opinion in International Appln. No. PCT/US2019/058924, dated Jan. 21, 2020, 17 pages.

PCT International Search Report and Written Opinion in International Appln. No. PCT/US2020/018371, dated May 7, 2020, 14 pages.

PCT International Search Report and Written Opinion in International Appln. No. PCT/US2020/028219, dated Jul. 15, 2020, 12 pages.

Peschechera et al., ""Browning" of adipose tissue-regulation and therapeutic perspectives," Archives of physiology and biochemistry, 119(4):151-60, Oct. 2013.

Pfanner et al., "Assembling the mitochondrial outer membrane," Nature Structural & Molecular Biology, Nov. 2004, 11(11):1044-8.

Phillips et al., "Homogenous protein programming in the mammalian left and right ventricle free walls," Physiological Genomics, Nov. 2011, 43(21):1198-206.

Phinney et al., "Mesenchymal stem cells use extracellular vesicles to outsource mitophagy and shuttle microRNAs," Nature Communications, Oct. 7, 2015, 6(1):1-5.

Pinton et al., "Biosensors for the detection of calcium and pH," Methods in Cell Biology, Jan. 1, 2007, 80:297-325.

(56) References Cited

OTHER PUBLICATIONS

Preble et al., "Quality Control Parameters for Mitochondria Transplant in Cardiac Tissue," Mol. Biol., Jun. 2, 2014, 2(1):1008.
Preble et al., "Rapid isolation and purification of mitochondria for transplantation by tissue dissociation and differential filtration," JoVE (Journal of Visualized Experiments), Sep. 6, 2014, (91):e51682, 6 pages.
Quirós et al., "New roles for mitochondrial proteases in health, ageing and disease," Nature Reviews Molecular Cell biology, Jun. 2015, 16(6):345-59.
Rahman et al., "Demarcating the membrane damage for the extraction of functional mitochondria," Microsystems & Nanoengineering, Dec. 31, 2018, 4(1):1-2.
Rajewsky, "microRNA target predictions in animals," Nature Genetics, Jun. 2006, 38(6):S8-13.
Ran et al., "Double nicking by RNA-guided CRISPR Cas9 for enhanced genome editing specificity, " Cell, Sep. 12, 2013, 154(6):1380-9.
Ran et al., "Genome engineering using the CRISPR-Cas9 system," Nature Protocols, Nov. 2013, 8(11):2281-308.
Risum et al., "Variability of global left ventricular deformation analysis using vendor dependent and independent two-dimensional speckle-tracking software in adults," Journal of the American Society of Echocardiography, Nov. 1, 2012, 25(11):1195-203.
Rodiger et al., "Simultaneous isolation of intact mitochondria and chloroplasts from a single pulping of plant tissue," Journal of Plant Physiology, May 2010, 167: 620-624.
Rogers et al., "When Cells Become Organelle Donors," Physiology, Nov. 2013, 28: 414-422.
Rosner et al., "Merging high-quality biochemical fractionation with a refined flow cytometry approach to monitor nucleocytoplasmic protein expression throughout the unperturbed mammalian cell cycle," Nature Protocols, Mar. 2013, 8(3):602-26.
Roucou et al., "A cytochrome c-GFP fusion is not released from mitochondria into the cytoplasm upon expression of Bax in yeast cells," FEBS letters, Apr. 14, 2000, 471(2-3):235-9.
Rousou et al., "Opening of mitochondrial KATP channels enhances cardioprotection through the modulation of mitochondrial matrix volume calcium accumulation, and respiration," American Journal of Physiology—Heart and Circulatory Physiology, Nov. 2004, 287:H967-H976.
Rowley et al., "Meeting lot-size challenges of manufacturing adherent cells for therapy," Bioprocess Int, Mar. 2012, 10(3), 16-22.
Rubino et al., "HmtDB, a genomic resource for mitochondrion-based human variability studies," Nucleic Acids Research, Jan. 2012, 40(D1):D1150-9.
Rudikoff et al., Single amino acid substitution altering antigen-binding specificity,: Proceedings of the National Academy of Sciences, Mar. 1, 1982, 79(6):1979-83.
Rustom et al., "Nanotubular Highways for Intercellular Organelle Transport," Science, Feb. 2004, 303: 1007-1010.
Sampaio et al., "Membrane lipidome of an epithelial cell line," Proceedings of the National Academy of Sciences, Feb. 1, 2011, 108(5): 1903-7.
Sass et al., "Folding of Fumarase during Mitochondrial Import Determines its Dual Targeting in Yeast," The Journal of Biological Chemistry, Nov. 2008, 278: 45109-45116.
Schmitt et al., "A semi-automated method for isolating functionally intact mitochondria from cultured cells and tissue biopsies," Anal Biochem, Dec. 2013, 443:66-74.
Seyfried, "Cancer as a mitochondrial metabolic disease," Frontiers in Cell and Developmental Biology, Jul. 2015, 3: 43 (12 pages).
Shapiro et al., "Clearance and maintenance of blood nucleotide levels with adenosine triphosphate-magnesium chloride injection," Circulatory Shock, Jan. 1, 1992, 36(1):62-7.
Sharei et al., "A vector-free microfluidic platform for intracellular delivery," Proceedings of the National Academy of Sciences, Feb. 5, 2013, 110(6):2082-7.
Shin et al., "A novel biological strategy for myocardial protection by intracoronary delivery of mitochondria: safety and efficacy," JACC: Basic to Translational Science, Dec. 2019, 4(8):871-88.
Sieber et al., "A protein shuttle system to target RNA into mitochondria, " Nucleic Acids Research, Aug. 1, 2011, 39(14):e96, 9 pages.
Sivitz et al., "Mitochondrial dysfunction in diabetes: from molecular mechanisms to functional significance and therapeutic opportunities," Antioxidants & Redox signaling, Feb. 15, 2010, 12(4):537-77.
Skrabanja et al., "Potential value of adenosine 5'-triphosphate (ATP) and adenosine in anaesthesia and intensive care medicine," British Journal of Anaesthesia, May 1, 2005, 94(5):556-62.
Slowinska et al., "Mitochondrial membrane potential and reactive oxygen species in liquid stored and cryopreserved turkey (*Meleagris gallopavo*) spermatozoa" Poultry Science, 97:3709-3717, 2018.
Soubannier et al., "A vesicular transport pathway shuttles cargo from mitochondria to lysosomes," Current Biology, Jan. 24, 2012, 22(2):135-41.
Spees et al., "Mitochondrial transfer between cells can rescue aerobic respiration," Proceedings of the National Academy of Sciences, Jan. 31, 2006, 103(5):1283-8.
Spinazzi et al., "Assessment of mitochondrial respiratory chain enzymatic activities on tissues and cultured cells," Nature Protocols, Jun. 2012, 7(6):1235-46.
Spuch et al., "Liposomes for targeted delivery of active agen+A3ts against neurodegenerative diseases (Alzheimer's disease and Parkinson's disease)," Journal of Drug Delivery, Jul. 13, 2011, vol. 2011, 13 pages.
Starkov, "Measurement of mitochondrial ROS production" Methods Mol Biol (2010) vol. 648, pp. 245-255.
Stephanopoulos et al., "Choosing an effective protein bioconjugation strategy," Nature Chemical Biology, Dec. 2011, 7: 876-884.
Stitt et al., "Metabolite Levels in Specific Cells and Subcellular Compartments of Plant Leaves," Methods In Enzymology, Jan. 1989, 174: 518-552.
Stojanovski et al., "Import of proteins into mitochondria," Methods in Cell Biology, Jan. 2007, 80:783-806.
Sun et al. "Systemic combined melatonin-mitochondria treatment improves acute respiratory distress syndrome in the rat," Journal of Pineal Research, 2015, 58: 137-150.
Surma et al., "An automated shotgun lipidomics platform for high throughput, comprehensive, and quantitative analysis of blood plasma intact lipids," European Journal of Lipid Science and Technology, Oct. 2015, 117(10):1540-9.
Suzuki et al., "In vivo porcine model of reperfused myocardial infarction: in situ double staining to measure precise infarct area/area at risk," Catheterization and Cardiovascular Interventions, Jan. 1, 2008, 71(1):100-7.
Templeton et al., "Improved DNA: liposome complexes for increased systemic delivery and gene expression," Nature Biotechnology, Jul. 1997, 15(7):647-52.
Thuwanut et al., "Cryopreservation of epididymal cat spermatozoa: effects of in vitro antioxidative enzymes supplementation and lipid peroxidation induction," Theriogenology, May 1, 2010, 73(8):1076-87.
Titov et al., "Complementation of mitochondrial electron transport chain by manipulation of the NAD+/NADH ratio," Science, Apr. 8, 2016, 352(6282):231-5.
Tonelli et al., "Causes and circumstances of death in pulmonary arterial hypertension," American Journal of Respiratory and Critical Care Medicine, Aug. 1, 2013, 188(3):365-9.
Toyoda et al., "Opening of Mitochondrial ATP-Sensitive Potassium Channels Enhances Cardioplegic Protection," Ann Thorac Surg, Apr. 2001, 71: 1281-9.
Treulen et al., "Cryopreservation induces mitochondrial permeability transition in a bovine sperm model," Cryobiology, Aug. 2018, 83:65-74.
Trudeau et al., "Lysosome acidification by photoactivated nanoparticles restores autophagy under lipotoxicity," Journal of Cell Biology, Jul. 4, 2016, 214(1):25-34.

(56) References Cited

OTHER PUBLICATIONS

Tsukube et al., Amelioration of ischemic calcium overload correlates with high-energy phosphates in senescent myocardium, Am J Physiol Heart Cir Physiol, Jul. 1997, 273: H418-H425.
Tsukube et al., "Developmental Differences In Cytosolic Calcium Accumulation Associated With Surgically Induced Global Ischemia: Optimization Of Cardioplegic Protection And Mechanism Of Action," The Journal of Thoracic and cardiovascular Surgery, Jul. 1996, 112: 175-184.
Uchenna Agu et al., "The lung as a route for systemic delivery of therapeutic proteins and peptides, " Respiratory Research, Aug. 2001, 2(4): 1-2.
Ui-Tei et al., "Sensitive assay of RNA interference in Drosophila and Chinese hamster cultured cells using firefly luciferase gene as target," FEBS Letters, Aug. 18, 2000, 479(3):79-82.
Vander Heiden et al. "Bcl-xL Regulates the Membrane Potential and Volume Homeostasis of Mitochondria" Cell, Nov. 28, 1997, 91(5):627-37.
Vander Heiden et al., "Understanding the Warburg Effect: The Metabolic Requirements of Cell Proliferation," Science, May 2009, 324: 1029-1033.
Varkouhi et al., "Endosomal escape pathways for delivery of biologicals," Journal of Controlled Release, May 2011, 151(3):220-8.
Vlieghe et al., "Synthetic therapeutic peptides: science and market," Drug Discovery Today, Jan. 1, 2010, 15(1-2):40-56.
Wakiyama et al., "Selective opening of mitochondrial ATP-sensitive potassium channels during surgically induced myocardial ischemia decreases necrosis and apoptosis," European Journal of Cardio-Thoracic Surgery, Mar. 1, 2002, 21(3):424-33.
Walter et al., "Advanced tools for the analysis of protein phosphorylation in yeast mitochondria," Analytical Biochemistry, Aug. 1, 2018, 554:23-7.
Wang et al., "Correcting human mitochondrial mutations with targeted RNA import," Proceedings of the National Academy of Sciences, Mar. 27, 2012, 109(13):4840-5.
Weber-Lotfi et al., "DNA import competence and mitochondrial genetics," Biopolymers and Cell, Jan. 2014(30)1:71-3.
Weber-Lotfi et al., "Nucleic acid import into mitochondria: new insights into the translocation pathways," Biochimica et Biophysica Acta (BBA)-Molecular Cell Research, Dec. 1, 2015, 1853(12):3165, 43 pages.
Wibom et al., "Measurement of ATP production and respiratory chain enzyme activities in mitochondria isolated from small muscle biopsy samples," Analytical Biochemistry, Dec. 15, 2002, 311(2):139-51.
Wieckowski et al., "Isolation of mitochondria-associated membranes and mitochondria from animal tissues and cells," Nat Protoc, Nov. 2009, 4:1582-1590.
Wright, "A new nebuliser," The Lancet, Jul. 1958, 272(7036):24-5.
Wu et al., "Covalent labeling of mitochondria with a photostable fluorescent thiol-reactive rhodamine-based probe," Analytical Methods, Mar. 2012, 4(6):1699-703.
Wu et al., "MicroRNAs direct rapid deadenylation of mRNA," Proceedings of the National Academy of Sciences, Mar. 14, 2006, 103(11):4034-9.
Yamaguchi et al., "Mitochondria frozen with trehalose retain a number of biological functions and preserve outer membrane integrity" Cell Death and Differentiation, 14:616-624, 2007.
Yin et al., "Adipocyte mitochondrial function is reduced in human obesity independent of fat cell size," The Journal of Clinical Endocrinology & Metabolism, Feb. 1, 2014, 99(2):E209-16.
Yin et al., "Non-viral vectors for gene-based therapy," Nature Reviews Genetics, Aug. 2014, 15(8):541-55.
Yu et al., "Capitalizing Resolving Power of Density Gradient Ultracentrifugation by Freezing and Precisely Slicing Centrifuged Solution: Enabling Identification of Complex Proteins from Mitochondria by Matrix Assisted Laser Desorption/Ionization Time-of-Flight Mass Spectrometry," Journal of Analytical Methods in Chemistry, 2016:1-7, 2016.
Yu et al., "Gene delivery to mitochondria by targeting modified adenoassociated virus suppresses Leber's hereditary optic neuropathy in a mouse model," Proceedings of the National Academy of Sciences, May 15, 2012, 109(20):E1238-47.
Yu et al., "Interaction between bevacizumab and murine VEGF-A: a reassessment," Investigative Ophthalmology & Visual Science, Feb. 2008, 49(2):522-7.
Zamzamiet et al., "Mitochondrial permeability transition in apoptosis and necrosis," Cell Death and Differentiation, Nov. 1, 2005, 12(S2):1478.
Zeng et al., "Both natural and designed micro RNAs can inhibit the expression of cognate mRNAs when expressed in human cells," Molecular Cell, Jun. 1, 2002, 9(6):1327-33.
Zetsche et al. "Cpf1 is a single RNA-guided endonuclease of a class 2 CRISPR-Cas system," Cell, Oct. 2015, 163:759-771.
Zhao et al., "Glutathione selectively modulates the binding of platinum drugs to human copper chaperone Cox17," Biochem J, Dec. 2015, 472(2):217-23.
Zhou et al., "Progress in the Field of Constructing Near-Infrared Light-Responsive Drug Delivery Platforms," Journal of Nanoscience and Nanotechnology, Mar. 2016, 16: 2111-2125.
Meschaninova et al., "Novel convenient approach to the solid-phase synthesis of oligonucleotide conjugates," Molecules, Nov. 2019, 24(23):4266, 14 pages.
Opalinska et al., "Nucleic-acid therapeutics: basic principles and recent applications," Nature Reviews Drug Discovery, Jul. 2002, 1(7):503-14.
Smith et al., "Nucleic acid nanostructures for biomedical applications," Nanomedicine, Jan. 2013, 8(1):105-21.
Stanfield et al., "Antibody Structure," Microbiology Spectrum, Mar. 2014, 2(2), 11 pages.
Amarzguioui et al., "An algorithm for selection of functional siRNA sequences," Biochemical and Biophysical Research Communications, Apr. 2004, 316(4):1050-8.
AU Office Action in Australian Application No. 2021201217, dated Feb. 1, 2022, 3 pages.
Cell Biology A Laboratory Handbook, 3rd ed., Fernandez-Vizaeea et al., Nov. 2005, Chapter 10, 12 Pages.
Chalk et al., "Improved and automated prediction of effective siRNA," Biochemical and Biophysical Research Communications, Jun. 2004, 319(1):264-74.
EP Extended European Search Report in European Appln. No. 20155650.3, mailed on Dec. 28, 2020, 14 pages.
Feng et al., "Isolation and Observation of Mitochondrion," Experimental Instructions for Cell Biology and Cell Engineering Experiments, Human Science and Technology Press, Aug. 1, 2013, 39-41, 10 pages (English translation of the relevant portion is provided).
Gabriel et al., "The mitochondrial machinery for import of precursor proteins," Protein Targeting Protocols, Jan. 2007, 390, 99-117.
Gasteiger et al., "Protein Identification and Analysis Tools on the ExPASy Server," The Proteomics Protocols Handbook, Mar. 2005, 571-607.
Hamilton, "The hidden risks for'three-person'babies," Nature, Sep. 2015, 525(7570), 3 pages.
Heale et al., "siRNA target site secondary structure predictions using local stable substructures," Nucleic Acids Research, Jan. 2005, 33(3):e30, 10 pages.
JP Office Action in Japanese Appln. No. 2018-536875, dated Jan. 27, 2021, 22 pages (with English translation).
Khvorova et al., "Functional siRNAs and miRNAs Exhibit Strand Bias," Cell, Oct. 2003, 115(2):209-16.
Pei et al., "On the art of identifying effective and specific siRNAs, " Nature Methods, Sep. 2006, 3(9):670-6.
Reynolds et al., "Rational siRNA design for RNA interference," Nature Biotechnology, Mar. 2004, 22(3):326-30.
Scanlon et al., "Pharmacological investigation of mitochondrial Ca2+ transport in central neurons: studies with CGP-37157, an inhibitor of the mitochondrial Na+--Ca2+ exchanger," Cell Calcium, Nov. 2000, 28(5-6):317-27.
Schwarz et al., "Asymmetry in the assembly of the RNAi enzyme complex," Cell, Oct. 2003, 115(2):199-208.

(56) References Cited

OTHER PUBLICATIONS

Sims et al., "Isolation of mitochondria from rat brain using Percoll density gradient centrifugation," Nature Protocols, Jul. 2008, 3(7):1228-39.
Ui-Tei, "Is the efficiency of RNA silencing evolutionarily regulated?," International Journal of Molecular Sciences, May 2016, 17(5):719, 10 pages.
EP Office Action in European Appln. No. 19926810.3, mailed on Jan. 7, 2026, 7 pages.

* cited by examiner

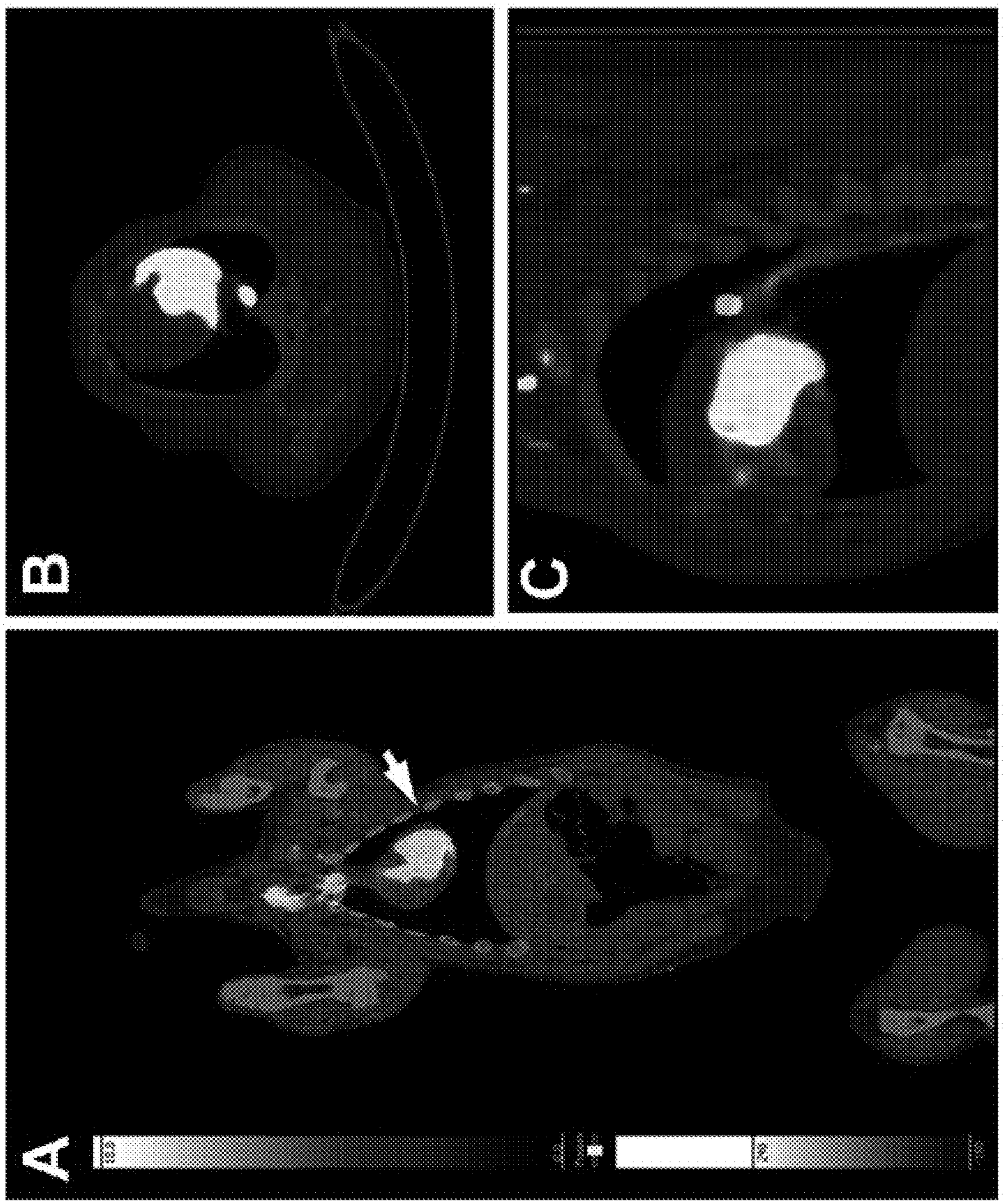
FIG. 11A-C

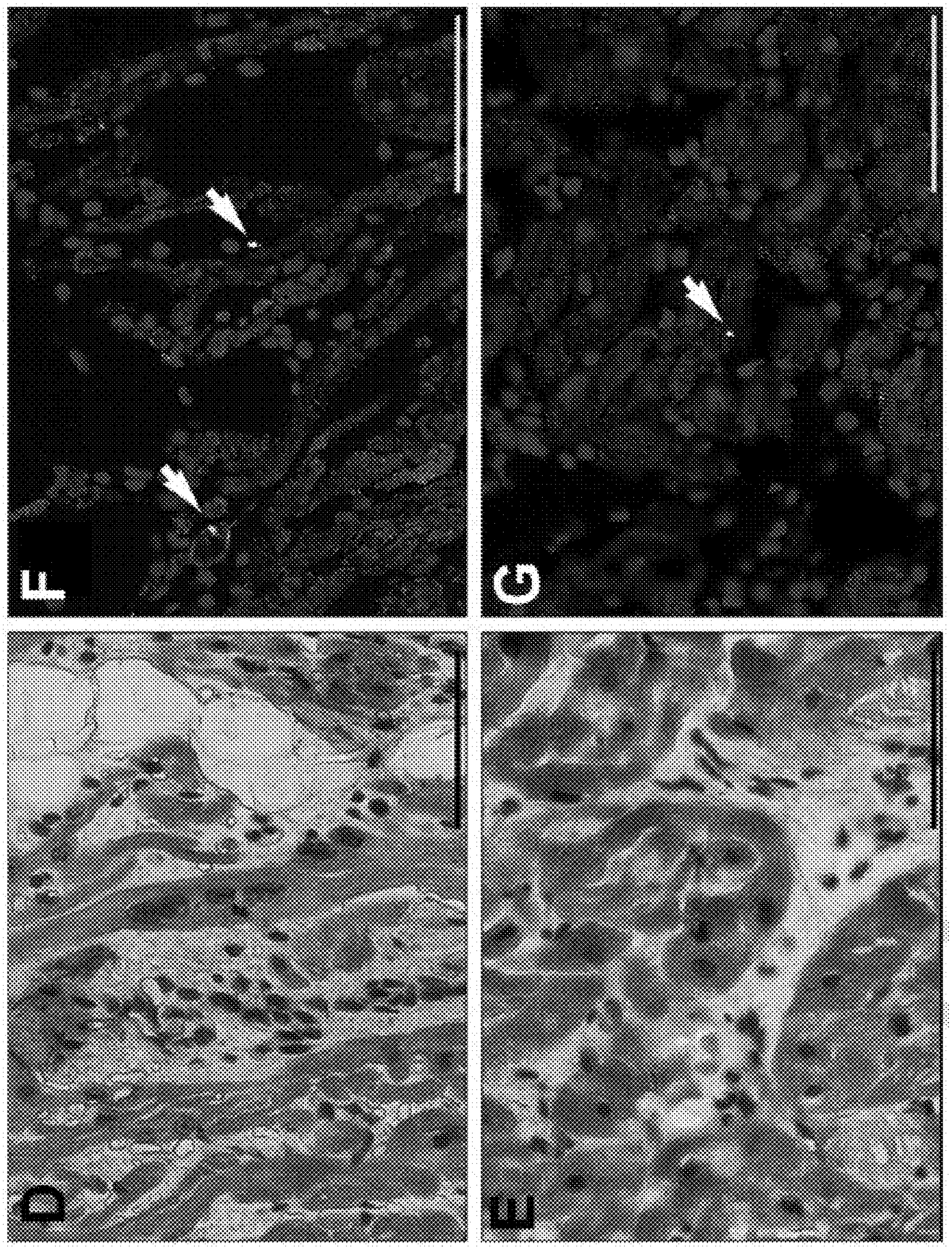
FIG. 11D-G

A
| | Baseline | Vehicle | $10^3$ Mitochondria | $10^5$ Mitochondria | $10^7$ Mitochondria | $10^9$ Mitochondria | $10^{11}$ Mitochondria |
|---|---|---|---|---|---|---|---|
| HR (beats/min) | 81.1 ± 9.3 | 78.7 ± 4.9 | 78.6 ± 7.9 | 78.7 ± 8.6 | 78.5 ± 8.4 | 78.9 ± 8.3 | 79.4 ± 7.8 |
| MAP (mmHg) | 69.9 ± 2.5 | 72.1 ± 4.3 | 68.9 ± 1.9 | 70.8 ± 2.3 | 70.1 ± 1.8 | 71.2 ± 1.8 | 71.9 ± 2.4 |
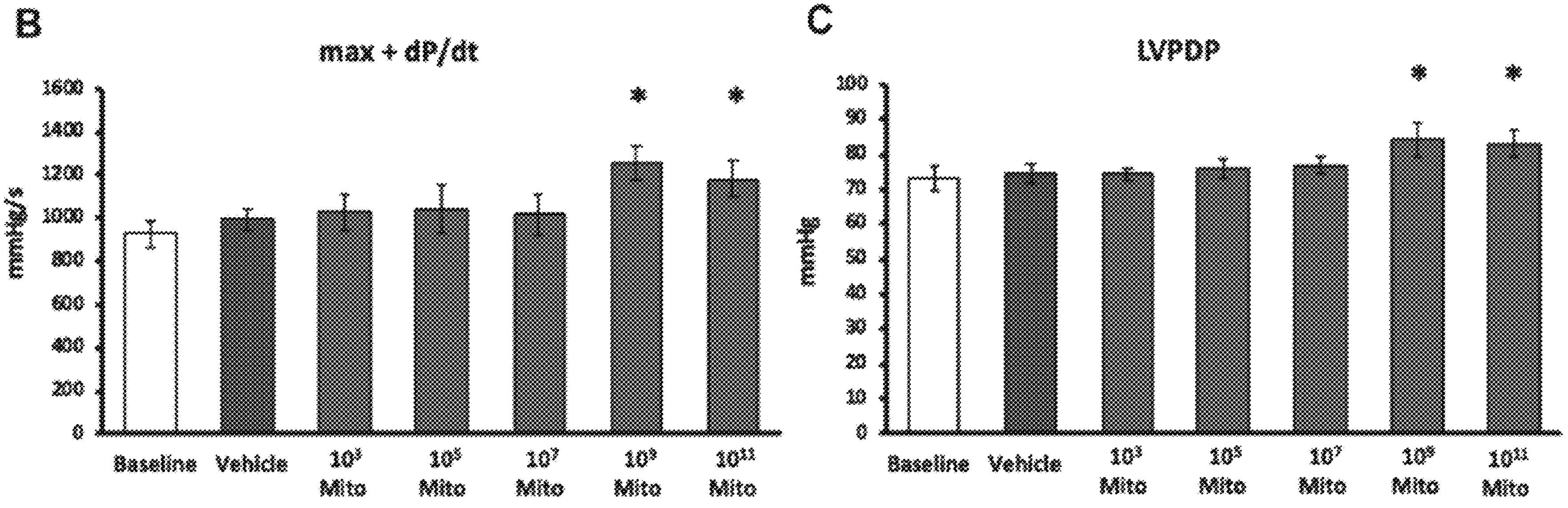
FIG. 12A-C

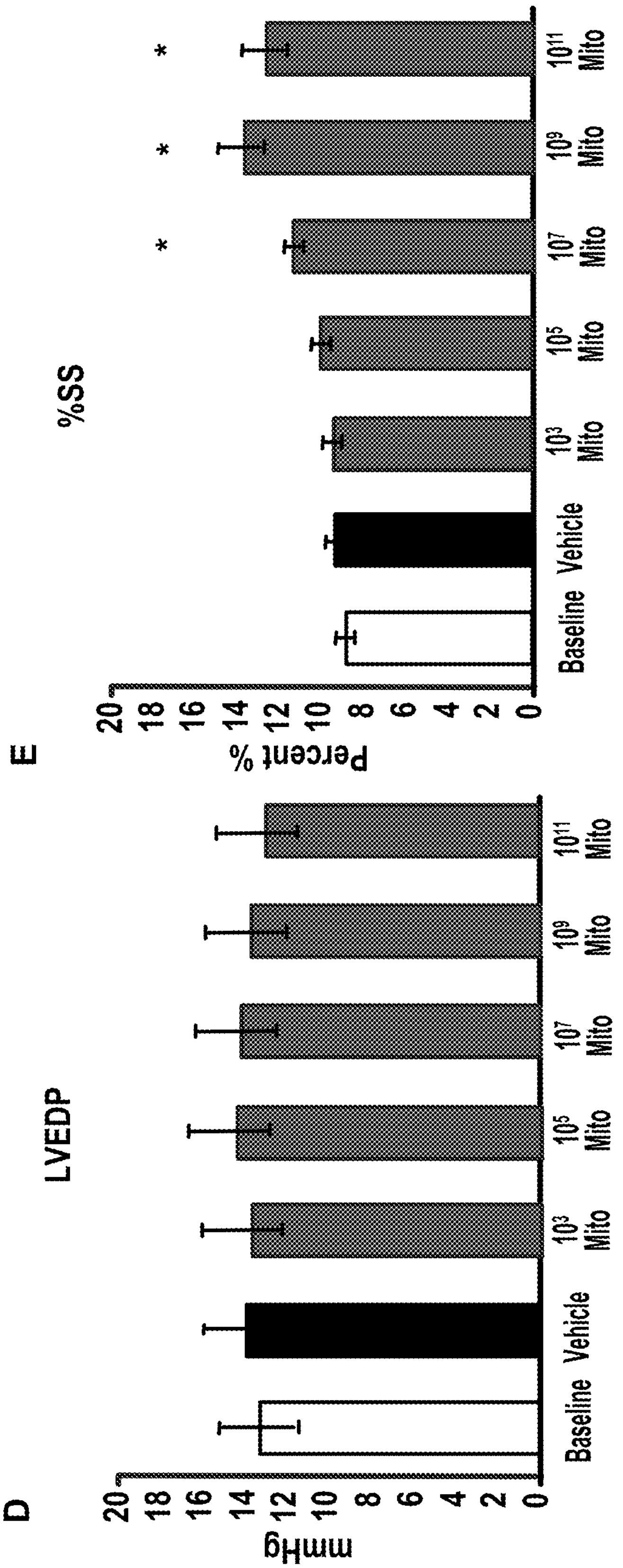
FIG. 12D-E

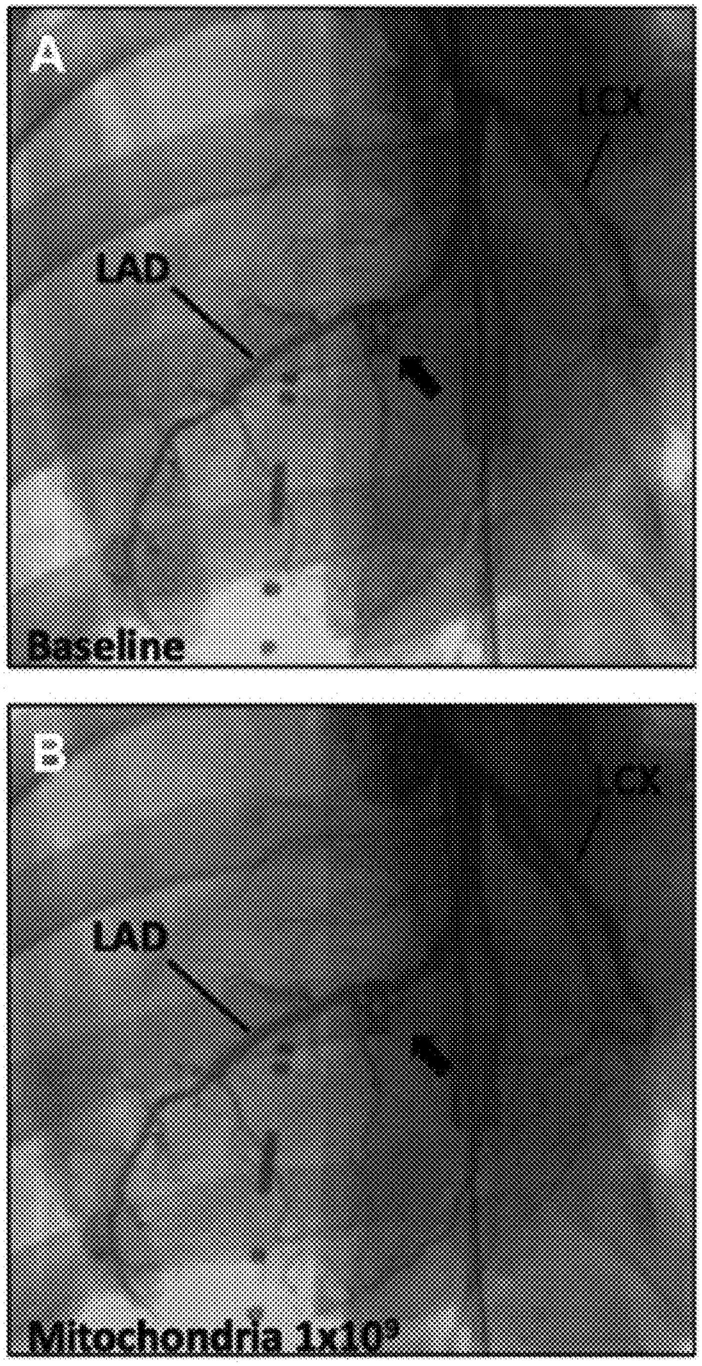
FIG. 13A-B

| Group | AUC | SE | 95% CI | P (vs. Vehicle) |
|---|---|---|---|---|
| Mitochondria 1 x $10^{11}$ | 18,262.3 | 2,131.6 | (14,084.4, 22,440.2) | < 0.001 |
| Mitochondria 1 x $10^{9}$ | 19,843.7 | 1,208.5 | (17,475.3, 22,212.0) | < 0.001 |
| Mitochondria 1 x $10^{7}$ | 10,001.7 | 914.3 | (8,209.7, 11,793.6) | 0.032 |
| Mitochondria 1 x $10^{5}$ | 8,154.6 | 647.5 | (6,885.4, 9,423.7) | 0.335 |
| Mitochondria 1 x $10^{3}$ | 7,718.3 | 695.0 | (6,356.1, 9,080.6) | 0.622 |
| Vehicle | 7,242.9 | 624.7 | (6,018.6, 8,467.3) | Reference |

FIG. 13D

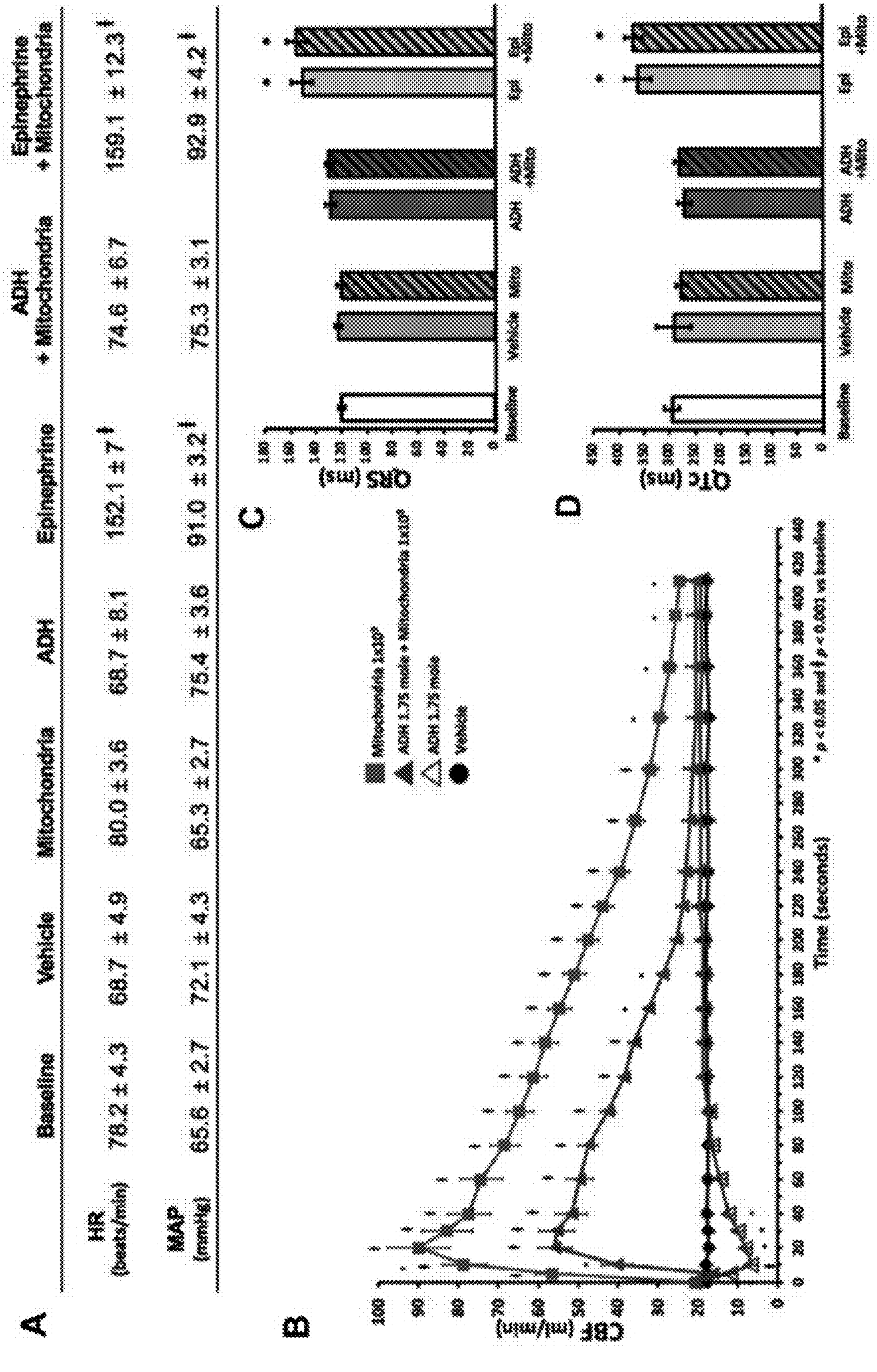
A
| | Baseline | Vehicle | Mitochondria | ADH | Epinephrine | ADH + Mitochondria | Epinephrine + Mitochondria |
|---|---|---|---|---|---|---|---|
| HR (beats/min) | 78.2 ± 4.3 | 68.7 ± 4.9 | 80.0 ± 3.6 | 68.7 ± 8.1 | 152.1 ± 7‡ | 74.6 ± 6.7 | 159.1 ± 12.3‡ |
| MAP (mmHg) | 65.6 ± 2.7 | 72.1 ± 4.3 | 65.3 ± 2.7 | 75.4 ± 3.6 | 91.0 ± 3.2‡ | 75.3 ± 3.1 | 92.9 ± 4.2‡ |
FIG. 14A-D

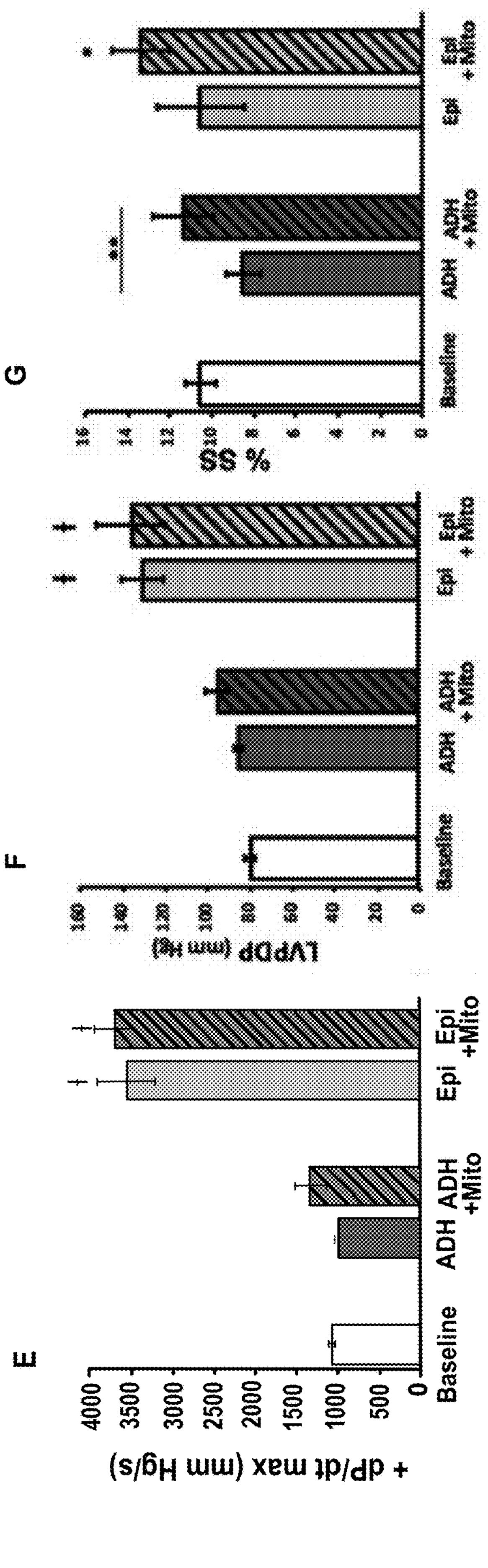
FIG. 14E-G

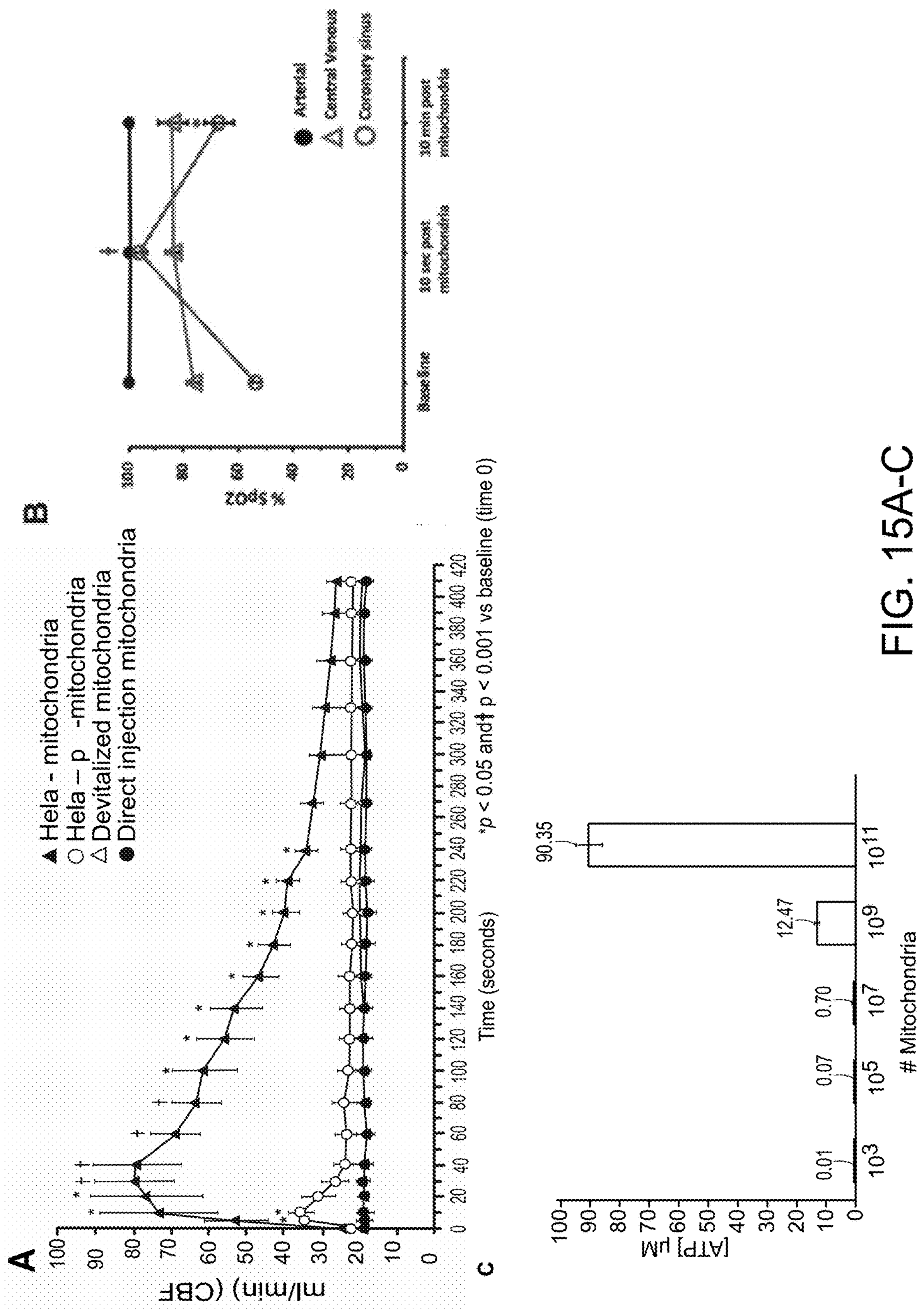
FIG. 15A-C

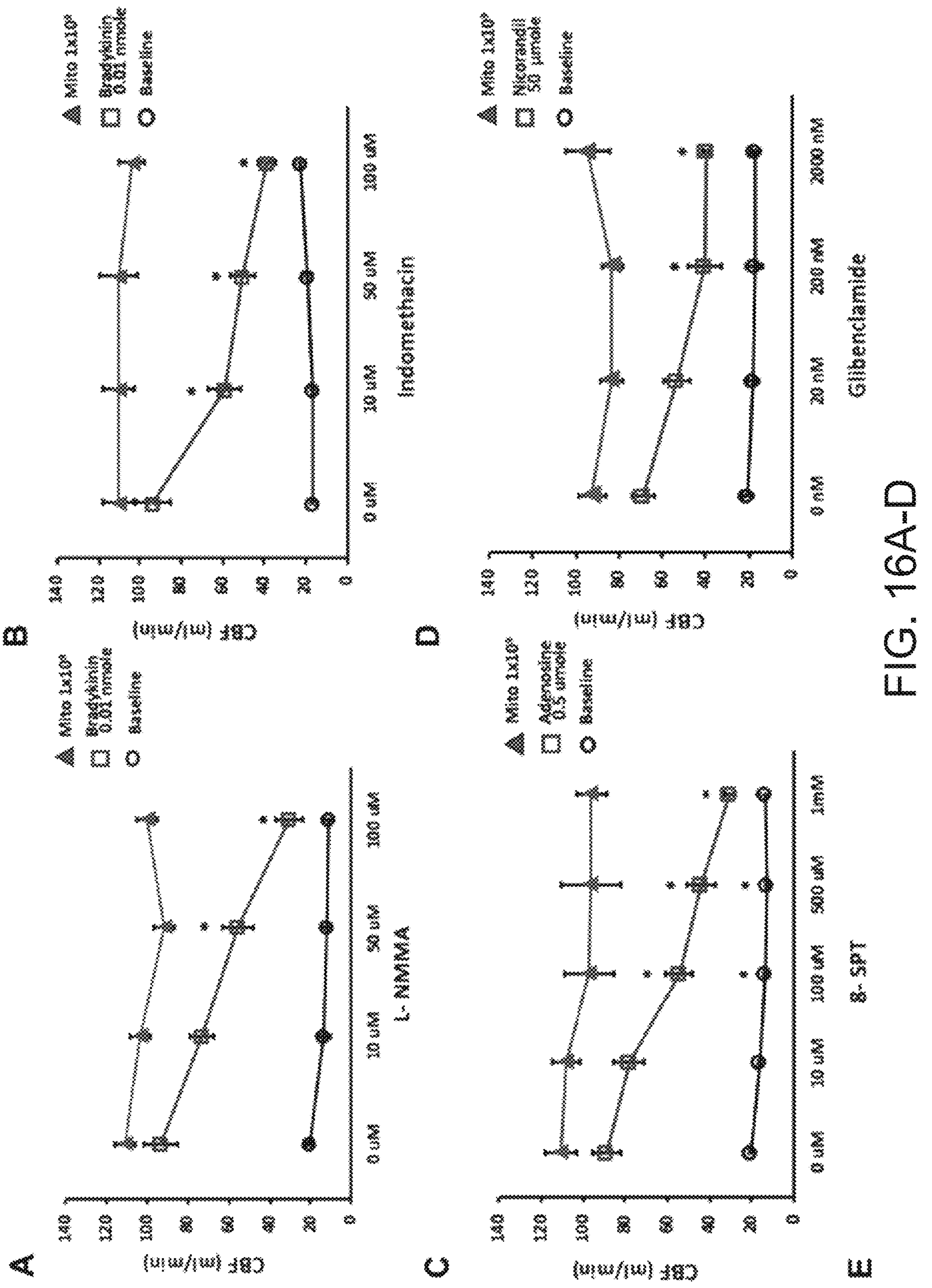
FIG. 16A-D

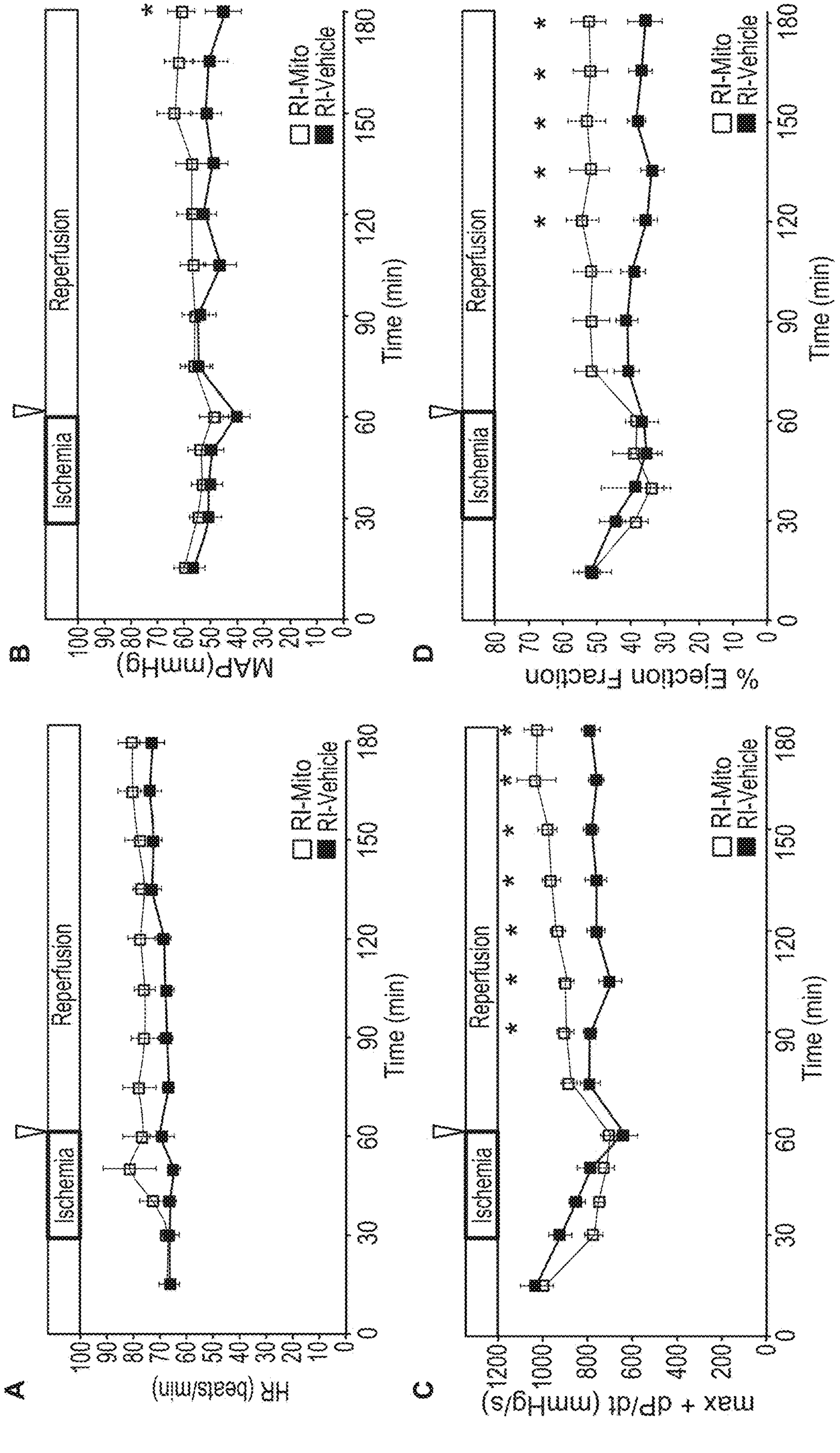
FIG. 17A-D

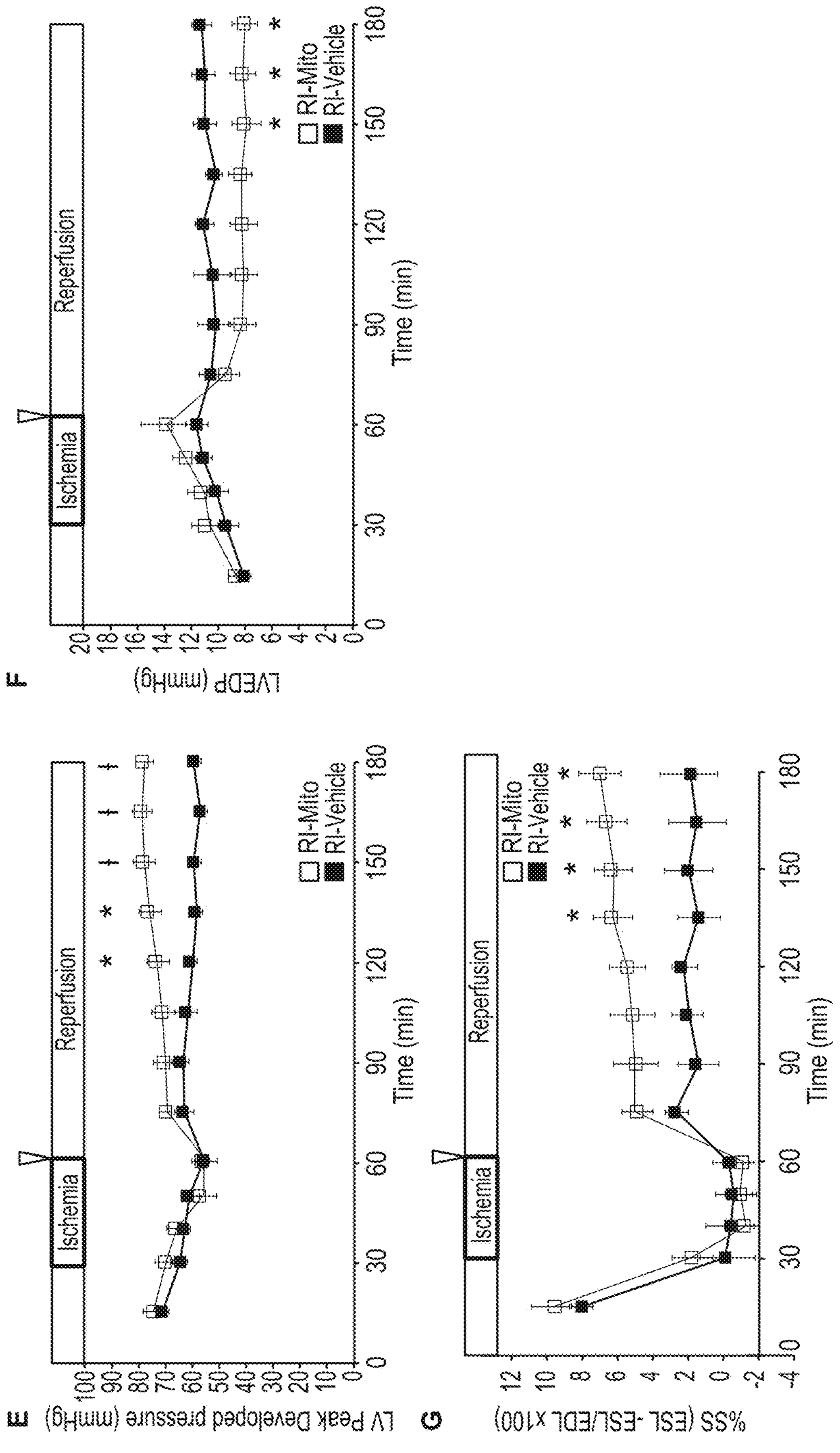
FIG. 17E-G

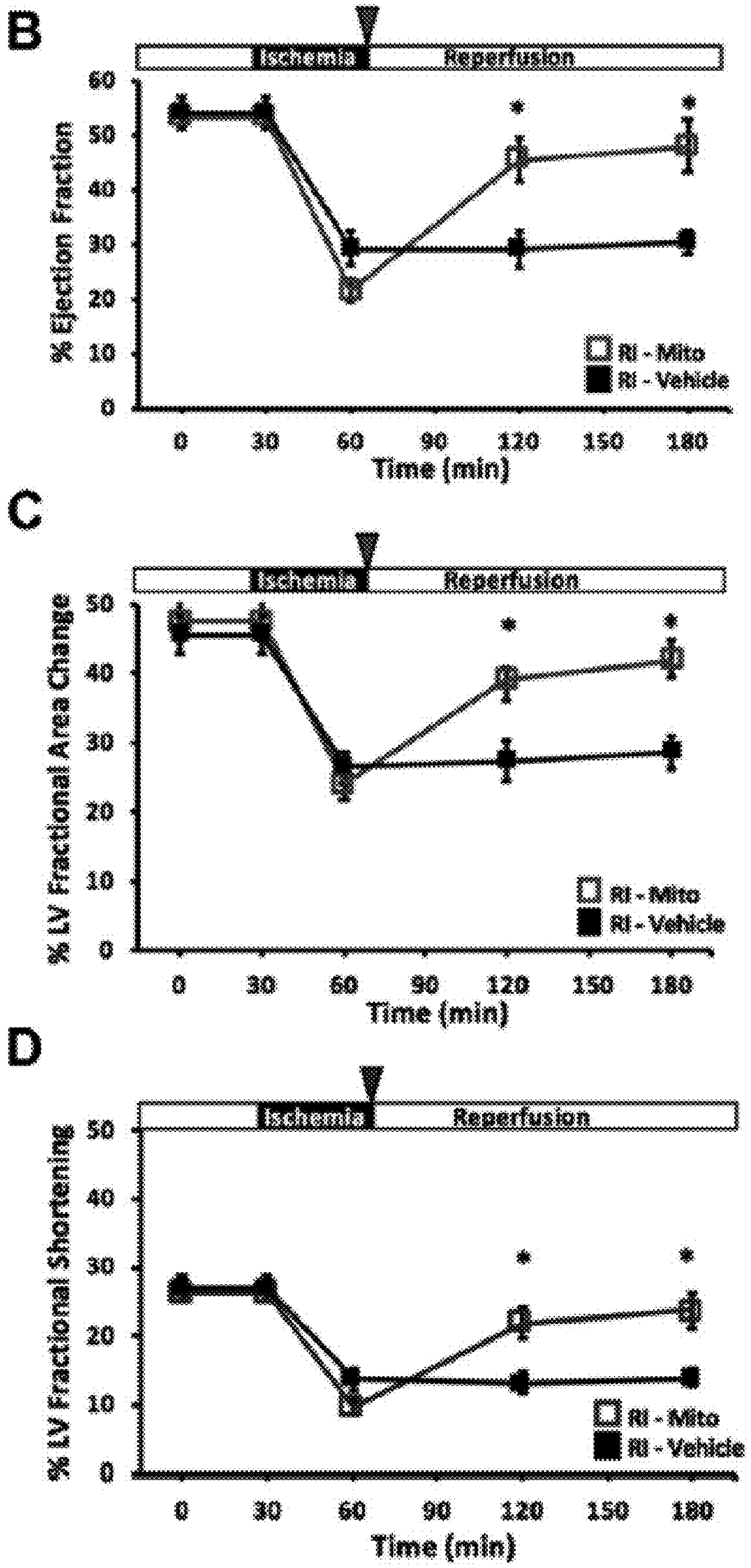
FIG. 18B-D

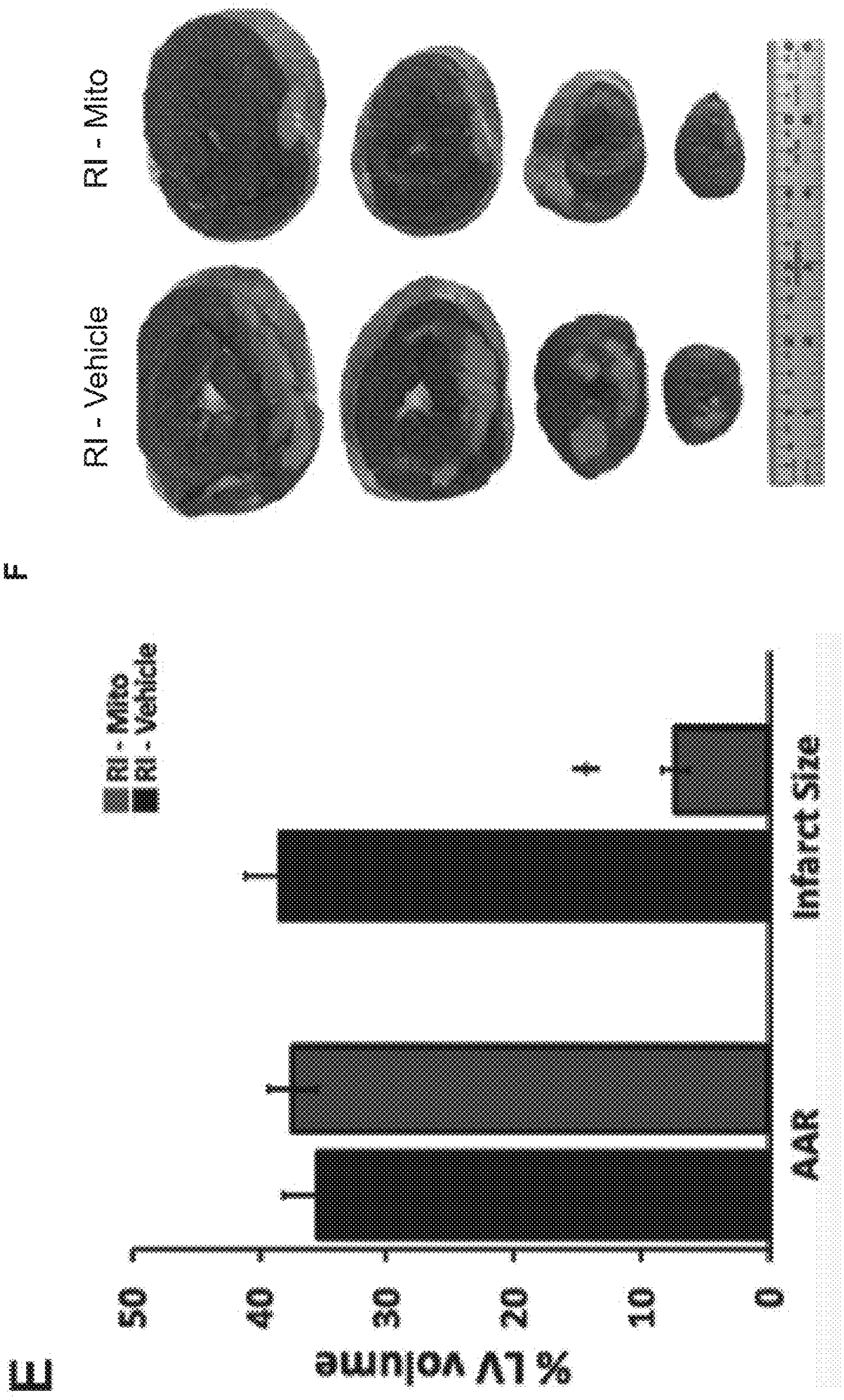
FIG. 18E-F

PROPHYLACTIC AND THERAPEUTIC USE OF MITOCHONDRIA AND COMBINED MITOCHONDRIAL AGENTS

CLAIM OF PRIORITY

This application is a U.S. National Phase Application under 35 U.S.C. § 371 of International Application No. PCT/US2019/058924, filed on Oct. 30, 2019, which claims the benefit of U.S. Provisional Application Ser. No. 62/842,320, filed on May 2, 2019. The entire contents of the foregoing are incorporated herein by reference.

STATEMENT AS TO FEDERALLY SPONSORED RESEARCH

This invention was made with Government support under grant numbers HL103642, HL029077, and HL068915, awarded by the National Institutes of Health. The Government has certain rights in the invention.

FIELD

The disclosure relates to prophylactic and therapeutic use of mitochondria and combined mitochondrial agents.

BACKGROUND

Coronary artery disease is the leading cause of death and disability worldwide with more than 9 million attributed deaths in 2016 (WHO. CHERG-WHO methods and data sources for child causes of death 2000-2016. 2018: Global Health Estimates Technical Paper WHO/HIS/IE).

There is sufficient data to show that ischemia-reperfusion injury (IRI) leads to alterations in cellular energy and homeostatic ions, accumulation of reactive oxygen species and DNA damage (Levitsky S, Laurikka J, Stewart R D, Campos C T, Lahey S J, McCully J D. Mitochondrial DNA deletions in coronary artery bypass grafting patients. Eur J Cardio-thoracic Surg. 2003; 24(5):777-784; Finkel T, Menazza S, Holmström K M, et al. The ins and outs of mitochondrial calcium. Circ Res. 2015; 116(11):1810-1819; Komfeld O S, Hwang S, Disatnik M H, Chen C H, Qvit N M-RD. Mitochondrial reactive oxygen species at the heart of the matter: new therapeutic approaches for cardiovascular diseases. Circ Res. 2015; 116(11):1783-1799). This ultimately activates signaling pathways for apoptosis and necrosis and presents as myocardial dysfunction (Zamzami N, Larochette N, Kroemer G. Mitochondrial permeability transition in apoptosis and necrosis. Cell Death Differ. 2005; 12:1478-1480). There is a need for therapeutics that can treat and reduce the risk of coronary artery disease, particularly ischemia-reperfusion injury.

SUMMARY

The disclosure relates to prophylactic and therapeutic use of mitochondria and combined mitochondrial agents.

In one aspect, described herein is a method of minimizing ischemia-reperfusion injury (IRI) in a subject during a procedure, comprising: administering to the subject a therapeutically effective amount of a composition comprising isolated mitochondria and/or a combined mitochondrial agent; and performing the procedure (e.g., a medical procedure, a surgery, an organ transplantation).

In one aspect, described herein is a method of reducing risk of ischemia-reperfusion injury (IRI) in a subject, comprising: identifying a subject at risk for IRI; and administering to the subject a therapeutically effective amount of a composition comprising isolated mitochondria and/or a combined mitochondrial agent.

In one aspect, described herein is a method of ameliorating at least one symptom of ischemia-reperfusion injury (IRI) in a subject caused by a procedure, comprising: administering to a subject having at least one symptom of IRI a therapeutically effective amount of a composition comprising isolated mitochondria and/or a combined mitochondrial agent; and performing the procedure.

In one aspect, described herein is a method of treating ischemia, reperfusion, an ischemic event, or an ischemic injury in a subject, comprising: administering to a subject having ischemia, reperfusion, an ischemic event, or an ischemic injury, a therapeutically effective amount of a composition comprising isolated mitochondria and/or a combined mitochondrial agent.

In one aspect, described herein is a method of preventing or treating cell damage, tissue damage, and/or organ damage associated with IRI in a subject, comprising: identifying the subject at risk for, or having, cell damage, tissue damage, and/or organ damage associated with IRI; and administering to the subject a therapeutically effective amount of a composition comprising isolated mitochondria and/or a combined mitochondrial agent.

In some embodiments, the composition is administered prior to ischemia or ischemic event.

In some embodiments, the subject has an ischemia-related disease. In some embodiments, the ischemia-related disease is an acute and/or chronic coronary syndrome. In some embodiments, the ischemia-related disease is a myocardial infarction. In some embodiments, the ischemia-related disease is a liver IRI, heart IRI, kidney IRI, brain IRI, lung IRI, pancreas IRI, or skeletal muscle IRI. In some embodiments, the ischemia-related disease is an ischemic injury-compartmental syndrome.

In some embodiments, the subject has diabetes.

In some embodiments, the composition is administered to the subject by injecting the composition into a blood vessel of the subject. In some embodiments, the blood vessel is the hepatic portal vein of the subject. In some embodiments, the blood vessel is the coronary artery of the subject. In some embodiments, the blood vessel is the renal artery of the subject.

In some embodiments, the blood vessel is the pulmonary artery of the subject. In some embodiments, the blood vessel is the prostate artery of the subject.

In some embodiments, the composition is administered to a tissue or an organ by direct injection. In some embodiments, the organ is selected from the following: heart, kidney, lung, skin, eye, liver, pancreas, lung, or prostate. In some embodiments, the tissue is of a limb or appendage.

In some embodiments, the administering is performed by intravenous, intra-articular, subcutaneous, intraperitoneal, intramuscular, intradermal, or intracardiac injection.

In some embodiments, the subject is administered a single dose of the composition. In some embodiments, the subject is administered multiple doses of the composition. In some embodiments, the multiple does are administered every 5 minutes, 10 minutes, 15 minutes, 20 minutes, or 30 minutes for a period lasting about or at least 10 minutes, 30 minutes, 60 minutes, 90 minutes, or 120 minutes.

In some embodiments, the mitochondria are autogeneic. In some embodiments, the mitochondria are allogeneic. In some embodiments, the mitochondria are xenogeneic.

In some embodiments, a method further comprises, prior to the administering step, a step of collecting the isolated mitochondria from cells, and wherein the administering step includes administering the isolated mitochondria to the subject immediately after the isolated mitochondria are collected from cells.

In some embodiments, the composition comprises about or at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ mitochondria and/or combined mitochondrial agents.

In some embodiments, the treatment prevents or reduces structural damage of mitochondria in the subject. In some embodiments, the treatment prevents or reduces functional damage of mitochondria in the subject. In some embodiments, the treatment prevents or reduces IRI-associated damage of a cell in the subject. In some embodiments, the treatment prevents or reduces IRI-associated damage of a tissue in the subject. In some embodiments, the treatment prevents or reduces IRI-associated damage of an organ in the subject. In some embodiments, the treatment reduces recovery time of the subject. In some embodiments, the treatment improves global function of an organ or a tissue in the subject. In some embodiments, the treatment improves regional function of an organ or a tissue in the subject.

In some embodiments, the tissue is selected from the group consisting of skin tissue, skeletal muscle, adipose tissue, facial muscle, bone marrow tissue, eye tissue, heart valves, veins, and tendons.

In some embodiments, the organ is selected from the group consisting of brain, thyroid, thymus, heart, lung, liver, pancreas, kidney, bladder, pancreas, small intestine, large intestine, colon, eye, and skin.

In some embodiments, subject has or is at risk of a metabolic disorder, a cancer, an immunological disease, or a mitochondrial dysfunction disorder.

In some embodiments, the IRI, ischemia, reperfusion, the ischemic event, or the ischemic injury is associated with a medical procedure (e.g., surgery, or organ/tissue transplant).

In some embodiments, the composition comprises a carrier, wherein the carrier is selected from the group consisting of respiration buffer, mitochondria buffer, University of Wisconsin (UW) solution, blood, or serum.

In one aspect, described here is a method of delivering an agent to a target site of a subject prior to ischemia at the target site comprising administering a therapeutically effective amount of a composition comprising isolated mitochondria and/or combined mitochondrial agent into a blood vessel that carries blood to the target site or tissue at the target site of the subject. In some embodiments, the target site is heart, kidney, pancreas, lung, liver, eye, optic nerve, brain, thymus, thyroid, intestine, colon, skin, or skeletal muscle of the subject. In some embodiments, the blood vessel is part of the vascular system of the subject that carries blood to the target site.

In some embodiments, the combined mitochondrial agent comprises a pharmaceutical agent linked to mitochondria by a covalent bond. In some embodiments, the combined mitochondrial agent comprises a pharmaceutical agent embedded in the mitochondria. In some embodiments, the combined mitochondrial agent comprises a therapeutic agent. In some embodiments, the combined mitochondrial agent comprises a diagnostic agent. In some embodiments, the combined mitochondrial agent comprises an antibody or an antigen binding fragment.

In one aspect, described herein is a method of treating or minimizing the risk of IRI in a subject having or at risk of developing a mitochondrial dysfunction disorder, comprising: administering to a subject having or at risk of developing a mitochondrial dysfunction disorder a therapeutically effective amount of a pharmaceutical composition comprising isolated mitochondria or a combined mitochondrial agent, wherein the composition is administered to the subject prior to the IRI. In some embodiments, the composition is administered to the subject by injecting the composition into a blood vessel of the subject. In some embodiments, the mitochondrial dysfunction disorder is Kearns-Sayre syndrome, MERRF syndrome, MELAS syndrome or Leber's disease. In some embodiments, the mitochondrial dysfunction disorder is Barth Syndrome. In some embodiments, the mitochondrial dysfunction disorder is diabetes. In some embodiments, the blood vessel is the greater pancreatic artery of the subject. In some embodiments, the mitochondrial dysfunction disorder is Parkinson's disease. In some embodiments, the pharmaceutical composition comprises a combined mitochondrial agent comprising a pharmaceutical agent.

In some embodiments, the mitochondria are autogeneic. In some embodiments, the autogeneic mitochondria have exogenous mtDNA. In some embodiments, the mitochondria are allogeneic. In some embodiments, the mitochondria are from the subject's first-degree relative. In some embodiments, the mitochondria are xenogeneic.

In one aspect, described herein is a method for minimizing IRI-associated damage in an organ comprising injecting an effective amount of isolated mitochondria or combined mitochondrial agent into a blood vessel of the organ prior to ischemia and/or reperfusion occurring in the organ. In some embodiments, the organ is treated in situ or ex vivo. In some embodiments, the organ is a transplanted organ or organ to be transplanted. In some embodiments, the organ is selected from the group consisting of brain, thyroid, thymus, heart, lung, liver, pancreas, kidney, bladder, pancreas, small intestine, large intestine, colon, eye, and skin. In some embodiments, the organ is a heart. In some embodiments, the organ is a kidney.

In one aspect, described herein is a method of treating IRI or IRI-associated damage in an egg cell, an embryo cell, an embryo, or a fetus comprising (1) obtaining an effective number of mitochondria; and (2) contacting the egg cell, the embryo cell, the embryo, or the fetus with the effective number of mitochondria prior to the IRI. In some embodiments, the egg cell, the embryo cell, the embryo, or the fetus has or is at risk of a mitochondrial defect. In some embodiments, the egg cell is prepared for in vitro fertilization. In some embodiments, the embryo cell is prepared during in vitro fertilization. In some embodiments, the embryo is prepared during in vitro fertilization. In some embodiments, the embryo is treated in vivo. In some embodiments, the fetus is treated in vivo. In some embodiments, the mitochondria are obtained from a subject, and wherein the subject is a male, who provides sperms for in vitro fertilization.

In one aspect, described herein is a method of improving mitochondrial structure and/or function in a cell at risk for IRI comprising contacting the cell prior to an ischemia with isolated mitochondria or a combined mitochondrial agent in an amount sufficient to improve mitochondrial structure and/or function in the cell. In some embodiments, the cell is a stem cell.

In one aspect, described herein is a method of improving mitochondrial structure and/or function in a tissue of a subject at risk for IRI comprising identifying a subject at risk for IRI; and administering to the tissue of the subject a composition comprising isolated mitochondria or a combined mitochondrial agent in an amount sufficient to improve mitochondrial structure and/or function in the tissue prior to an IRI. In some embodiments, the tissue is skin tissue, skeletal muscle tissue, facial muscle, bone marrow tissue, or white adipose tissue. In some embodiments, the composition is administered to the tissue by injecting the composition into the tissue.

In one aspect, described herein is a method of transplanting a cell, a group of cells, or a tissue to a subject, the method comprising contacting the cell, the group of cells, or the tissue with an effective amount of a composition comprising isolated mitochondria prior to transplantation; and transplanting the cell or the tissue into the subject. In some embodiments, the cell is a stem cell. In some embodiments, the tissue is selected from the group comprising bone marrow, skin tissue, skeletal muscle, adipose tissue, and combinations thereof.

In one aspect, described herein is a method of improving mitochondrial function in a cell or a tissue at risk of IRI, the method comprising contacting the cell or the tissue with an effective amount of a composition comprising isolated mitochondria and/or a combined mitochondrial agent prior to the IRI, to thereby improve mitochondrial function in the cell or tissue. In some embodiments, the cell is a transplanted cell. In some embodiments, the cell is a stem cell. In some embodiments, the tissue is a transplanted tissue. In some embodiments, the tissue is selected from the group comprising bone marrow, skin tissue, skeletal muscle, adipose tissue, and combinations thereof.

In one aspect, described herein is a method of treating or reducing the risk of developing IRI in a subject having a metabolic disorder comprising administering a composition comprising isolated mitochondria or a combined mitochondrial agent into white adipose tissue of the subject in an amount sufficient to treat the metabolic disorder, wherein the composition is administered to the subject having a metabolic disorder before ischemia. In some embodiments, the metabolic disorder is obesity or type II diabetes.

In some embodiments, the present disclosure provides methods to improve (e.g., shorten) recovery time following IRI in a subject comprising providing a subject a composition comprising mitochondria or mitochondrial agents. In some embodiments, the present disclosure provides methods to improve organ, tissue, and/or cell function following IRI in a subject comprising providing a subject a composition comprising mitochondria or mitochondrial agents. In some embodiments, the present disclosure provides methods to improve organ, tissue, and/or cell recovery following IRI in a subject comprising providing a subject a composition comprising mitochondria or mitochondrial agents. In some embodiments, the present disclosure provides methods of prophylactic protection of an organ, tissue, and/or cell prior to IRI in a subject comprising providing a subject a composition comprising mitochondria or mitochondrial agents. In some embodiments, the present disclosure provides methods to protect an organ, tissue, and/or cell during an IRI in a subject comprising providing a subject a composition comprising mitochondria or mitochondrial agents.

Administration of mitochondria and/or combined mitochondrial agents is also referred to as "mitochondrial transplantation" (MT).

In some embodiments, the present disclosure provides pharmaceutical compositions comprising mitochondria and methods of treating disorders using such pharmaceutical compositions. The specification further provides diagnostic and imaging methods using such pharmaceutical compositions. The described methods are based, at least in part, on the discovery that isolated mitochondria themselves, and isolated mitochondria linked to a therapeutic agent, diagnostic agent and/or imaging agent, can be delivered to a patient's tissue by injecting them into the patient's blood vessels. That is, direct injection or application of mitochondria to the target tissue, while contemplated by certain methods described herein, is not always necessary. Rather, in some instances, methods described herein take advantage of the discovery that after mitochondria are injected or infused, for example, into an artery, the mitochondria can transverse the artery wall and be taken up by cells of the patient's tissues. Methods described herein can provide localized, regional, systemic, and general distribution of mitochondria or mitochondria with therapeutic, diagnostic, and/or imaging agents to tissues or cells for a variety of prophylactic, treatment, diagnostic, and/or imaging purposes using relatively simple medical procedures.

In one aspect, the disclosure relates to methods of treating a subject having an IRI and/or ischemia-related disease. The methods include the step of administering a therapeutically effective amount of a composition comprising isolated mitochondria, or a composition comprising a combined mitochondrial agent, to the subject, e.g., by direct injection, by vascular infusion, and/or by injecting the composition into the blood vessel of the subject. The ischemia-related disease can be any disease that involves ischemia, e.g., an acute coronary syndrome, a myocardial infarction, a liver ischemia-reperfusion injury, an ischemic injury-compartmental syndrome, a chronic ischemia, heart failure, and/or hypertension. The IRI can be any injury involving ischemia, e.g., myocardial infarction, stroke, organ transplant, and the like.

In some embodiments, the disclosure relates to methods of prophylactic treatment of IRI and/or ischemia-related disease. The methods comprise steps of administering a therapeutically effective amount of a composition comprising isolated mitochondria, or a composition comprising a combined mitochondrial agent, to the subject, e.g., by direct injection, by vascular infusion, and/or by injecting the composition into the blood vessel of the subject. The ischemia-related disease can be any disease that involves ischemia, e.g., an acute coronary syndrome, a myocardial infarction, a liver ischemia-reperfusion injury, or an ischemic injury-compartmental syndrome. In some embodiments, the subject that has ischemia-related disease has diabetes.

In certain embodiments, the blood vessel is the blood vessel or part of the vascular system which carries the blood to the target site, the target organ, or the target area, e.g., the coronary artery of the subject, the hepatic portal vein of the subject, the greater pancreatic artery of the subject, or the prostate artery of the subject.

In certain embodiments, the mitochondria can have different sources, e.g., the mitochondria can be autogeneic, allogeneic, or xenogeneic. In certain embodiments, the autogeneic mitochondria can have exogenous mtDNA. In some embodiments, the mitochondria are from a subject's relative (e.g., first-degree relative).

In some embodiments, the described methods include the steps of collecting the isolated mitochondria from cells prior to administration. The isolated mitochondria or combined mitochondrial agent can be administered to the subject immediately after the isolated mitochondria are collected from cells.

As used herein, the term "isolated mitochondria" means functional and intact mitochondria that are free of extraneous eukaryotic cell material.

A "combined mitochondrial agent" is an isolated mitochondrion that is combined artificially with a pharmaceutical, diagnostic, or imaging, or any other agent. The agent is combined with a mitochondrion in any fashion, for example, linked (e.g., chemically or electrostatically linked) to a mitochondrion, attached to a mitochondrion, embedded in the mitochondrial membrane, substantially enclosed within a mitochondrion, or encapsulated entirely by a mitochondrion, as long as the mitochondrion and the agent are in physical contact with each other. Combined mitochondrial agents are designed such that the mitochondrion act as a "carrier" that can transport the agent to a patient's tissues after injection.

The terms "subject" and "patient" are used throughout the specification to describe an animal, human or non-human, to whom treatment according to the methods of the present disclosure is provided. Veterinary applications are clearly anticipated by the present disclosure. The term includes but is not limited to birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

The term "treat" or "treatment" is used herein to denote delaying the onset of, inhibiting, alleviating the effects of, or prolonging the life of a patient suffering from, a condition, e.g., a disease described herein.

An "ischemia-related disease" is a disease that involves ischemia. Ischemia, as used herein, is a reduced blood flow to an organ and/or tissue. The reduced blood flow may be caused by any suitable mechanism, including a partial or complete blockage (an obstruction), a narrowing (a constriction), and/or a leak/rupture, among others, of one or more blood vessels that supply blood to the organ and/or tissue.

By "immediately after mitochondria are collected from cells" is meant after mitochondria are collected from cells and before any substantial reduction in viability of the mitochondria can occur.

As used herein, the term "transplantation" is used throughout the specification as a general term to describe the process of implanting an organ, tissue, mass of cells, individual cells, or cell organelles into a recipient. The term "cell transplantation" is used throughout the specification as a general term to describe the process of transferring at least one cell, e.g., an islet cell, or a stem cell, to a recipient. For example, such transplantation can be performed by removing the β-cells (or intact islets) from a donor's pancreas and putting them into a recipient patient whose pancreas cannot produce sufficient insulin. The terms include all categories of transplants known in the art, except blood transfusions. Transplants are categorized by site and genetic relationship between donor and recipient. The term includes, e.g., autotransplantation (removal and transfer of cells or tissue from one location on a patient to the same or another location on the same subject), allotransplantation (transplantation between members of the same species), and xenotransplantation (transplantations between members of different species).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety for any and all purposes. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 11A shows biodistribution and myocardial uptake of autologous mitochondria by intracoronary delivery via a representative PET image 10 min after intracoronary injection of $^{18}$F-rhodamine-6G iron (II, III) oxide nanoparticle-labeled mitochondria. Tracer accumulation is observed in the left ventricle (arrow) and along the coronary angiography catheter present through the right carotid arterial access (arrowhead).

FIG. 11B shows a representative PET image 10 min after intracoronary injection of $^{18}$F-rhodamine-6G iron (II, III) oxide nanoparticle-labeled mitochondria. Tracer accumulation is observed in the left ventricle (arrow) and along the coronary angiography catheter present through the right carotid arterial access (arrowhead).

FIG. 11C shows a representative PET image 10 min after intracoronary injection of $^{18}$F-rhodamine-6G iron (II, III) oxide nanoparticle-labeled mitochondria. Tracer accumulation is observed in the left ventricle (arrow) and along the coronary angiography catheter present through the right carotid arterial access (arrowhead).

FIG. 11D shows a representative Prussian blue stain of iron oxide-labeled human mitochondria transplanted into a swine myocardium.

FIG. 11E shows a representative Prussian blue stain of iron oxide-labeled human mitochondria transplanted into a swine myocardium.

FIG. 11F shows a representative fluorescence immunohistochemistry of the transplanted mitochondria in consecutive slices of Panel D (arrows).

FIG. 11G shows a representative fluorescence immunohistochemistry of the transplanted mitochondria in consecutive slices of Panel E (arrows). Green: antihuman mitochondria (MTC02); red: antisarcomeric α-actinin; blue (DAPI): nuclei. Scale bars=100 mm.

FIG. 12A is a table illustrating heart rate (HR) and mean arterial pressure (MAP) at baseline, after intracoronary injection of vehicle and different concentrations of mitochondria (n=6).

FIG. 12B is a bar graph illustrating a representative global functional assessment of the left ventricle, maximal rate of increase of left ventricular pressure (maximal proportion dP/dt), after intracoronary injection of mitochondria at different mitochondrial concentrations (n=6).

FIG. 12C is a bar graph illustrating a representative global functional assessment of the left ventricle, left ventricular peak developed pressure (LVPDP), after intracoronary injection of mitochondria at different mitochondrial concentrations (n=6).

FIG. 12D is a bar graph illustrating a representative global functional assessment of the left ventricle, left ventricular end-diastolic pressure (LVEDP), after intracoronary injection of mitochondria at different mitochondrial concentrations (n=6).

FIG. 12E is a bar graph illustrating regional left ventricular contractile assessment by proportion segmental shortening (% SS) (n=6). All values are mean±SEM, averaged during 60 cardiac cycles immediately after intracoronary injections. * p<0.05 versus vehicle. Mito=mitochondria.

FIG. 13A shows a representative coronary angiography of swine under baseline condition.

FIG. 13B shows a representative coronary angiography of swine immediately after intracoronary injection of $1\times10^9$ mitochondria. Transonic flow probe (arrows).

FIG. 13D is a table illustrating comparisons of the area under the curve (AUC) of graph in FIG. 13C using the trapezoidal rule from time 0 to 410 s, in milliliters per min×s.

FIG. 14A is a table illustrating heart rate and mean arterial pressure after intracoronary injection of mitochondria ($1\times10^9$) at normal condition (baseline) and during coronary vasoconstriction induced by antidiuretic hormone (ADH; 1.75 nmol) and tachycardia induced by epinephrine (Epi; 0.5 mmol). † p<0.001 versus baseline (n=6).

FIG. 14B is a line graph illustrating coronary blood flow (CBF) after intracoronary injection of mitochondria ($1\times10^9$), vehicle, ADH, and ADH+mitochondria ($1\times10^9$). * p<0.05 and † p<0.001 versus baseline (time 0) (n=6).

FIG. 14C is a bar graph illustrating lengths of QRS complex after intracoronary injection of mitochondria ($1\times10^9$), vehicle, ADH, ADH+mitochondria, epinephrine, and epinephrine+mitochondria.

FIG. 14D is a bar graph illustrating lengths of corrected QT intervals (QTc) after intracoronary injection of mitochondria ($1\times10^9$), vehicle, ADH, ADH+mitochondria, epinephrine, and epinephrine+mitochondria.

FIG. 14E is a bar graph illustrating representative left ventricular contractile assessment of maximal rate of increase of left ventricular pressure (maximal proportion dP/dt) after intracoronary injection of the designated agents.

FIG. 14F is a bar graph illustrating representative left ventricular contractile assessment of left ventricular peak developed pressure (LVPDP) after intracoronary injection of the designated agents.

FIG. 14G is a bar graph illustrating representative left ventricular contractile assessment of left ventricular end-diastolic pressure (LVEDP) after intracoronary injection of the designated agents. * $p<0.05$ versus baseline, † $p<0.001$ versus baseline, and ** $p<0.05$ between groups designated by bars (n=6). Values are mean±SEM, averaged during 60 cardiac cycles after intracoronary injections of designated agents.

FIG. 15A is a line graph illustrating coronary blood flow on direct myocardial injection of mitochondria at 10 different sites in close proximity to the left anterior descending artery ($1\times10^9$ total; n=3), intracoronary injection of devitalized mitochondria ($1\times10^9$; n=4), and mitochondria isolated from HeLa cells and from HeLa-$p^0$ cells (n=6). * $p<0.05$ and † $p<0.001$ versus baseline (time 0).

FIG. 15B is a line graph illustrating percentage oxygen saturation (% $SpO_2$) of blood from the carotid artery (arterial), superior vena cava (central venous), and coronary sinus collected 10 s (during peak increase in coronary blood flow) and 10 min after intracoronary injection of mitochondria (n=4). Values are mean±SEM. * $p<0.05$ and † $p<0.001$ versus baseline % $SpO_2$ within each group.

FIG. 15C is a bar graph illustrating ATP content present in various concentrations of mitochondria.

FIG. 16A is a line graph illustrating representative CBF on intracoronary injection of mitochondria ($1\times10^9$) after pretreatment with increasing concentrations of nitric oxide synthase inhibitor nitro-monomethyl L-arginine (L-NMMA). CBF after bradykinin injection (nitric oxide synthase activator, 0.01 nmol) shows positive inhibition of nitric oxide synthase (n=4). Baseline indicates CBF after 20 min of pretreatment with L-NMMA before intracoronary injection of mitochondria or bradykinin.

FIG. 16B is a line graph illustrating representative CBF on intracoronary injection of mitochondria after pretreatment with increasing concentrations of cyclooxygenase inhibitor indomethacin. CBF after bradykinin injection (cyclooxygenase activator, 0.01 nmol) shows positive inhibition of cyclooxygenase (n=4).

FIG. 16C is a line graph illustrating representative CBF on intracoronary injection of mitochondria after pretreatment with increasing concentrations of adenosine receptor inhibitor 8-p-sulfophenyl theophylline (8-SPT). CBF after adenosine (0.5 mmol) injection shows positive inhibition of adenosine receptor (n=4).

FIG. 16D is a line graph illustrating representative CBF on intracoronary injection of mitochondria after pretreatment with increasing concentrations of $K_{ATP}$-channel inhibitor glibenclamide. CBF after nicorandil injection ($K_{ATP}$-channel activator, 50 mmol) shows positive inhibition of $K_{ATP}$ channels (n=4).

FIG. 17A is a line graph illustrating heart rate after intracoronary mitochondrial transplantation in regional myocardial IRI in the vehicle-only group (RI-Vehicle) and mitochondria group (RI-Mito) at pre-ischemia, during 30 min of regional ischemia and 120 min of reperfusion.

FIG. 17B is a line graph illustrating mean arterial pressure after intracoronary mitochondrial transplantation in regional myocardial IRI in the vehicle-only group (RI-Vehicle) and mitochondria group (RI-Mito) at pre-ischemia, during 30 min of regional ischemia and 120 min of reperfusion.

FIG. 17C is a line graph illustrating max+dP/dt (mm Hg) after intracoronary mitochondrial transplantation in regional myocardial IRI in the vehicle-only group (RI-Vehicle) and mitochondria group (RI-Mito) at pre-ischemia, during 30 min of regional ischemia and 120 min of reperfusion.

FIG. 17D is a line graph illustrating proportion ejection fraction after intracoronary mitochondrial transplantation in regional myocardial IRI in the vehicle-only group (RI-Vehicle) and mitochondria group (RI-Mito) at pre-ischemia, during 30 min of regional ischemia and 120 min of reperfusion.

FIG. 17E is a line graph illustrating left ventricular peak developed pressure (mm Hg) after intracoronary mitochondrial transplantation in regional myocardial IRI in the vehicle-only group (RI-Vehicle) and mitochondria group (RI-Mito) at pre-ischemia, during 30 min of regional ischemia and 120 min of reperfusion.

FIG. 17F is a line graph illustrating left ventricular end-diastolic pressure (mm Hg) after intracoronary mitochondrial transplantation in regional myocardial IRI in the vehicle-only group (RI-Vehicle) and mitochondria group (RI-Mito) at pre-ischemia, during 30 min of regional ischemia and 120 min of reperfusion.

FIG. 17G is a line graph illustrating proportion segmental shortening at the end of systole in the vehicle-only group (RI-Vehicle) and mitochondria group (RI-Mito) at pre-ischemia, during 30 min of regional ischemia and 120 min of reperfusion. Arrowheads denote the time of intracoronary injection of either vehicle or mitochondria. * $p<0.05$ and † $p<0.001$ between the 2 groups.

FIG. 18B is a line graph illustrating representative echocardiographic analysis of left ventricular (LV) function, % Ejection Fraction, analyzed from the short-axis view and M-mode tracings at the midpapillary level. Values are mean±SEM; * $p<0.05$ versus RI-Vehicle.

FIG. 18C is a line graph illustrating representative echocardiographic analysis of left ventricular (LV) function, % LV Fractional Area Change, analyzed from the short-axis view and M-mode tracings at the midpapillary level. Values are mean±SEM; * $p<0.05$ versus RI-Vehicle.

FIG. 18D is a line graph illustrating representative echocardiographic analysis of left ventricular (LV) function, % LV Factional Shortening, analyzed from the short-axis view and M-mode tracings at the midpapillary level. Values are mean±SEM; * $p<0.05$ versus RI-Vehicle.

FIG. 18E is a bar graph illustrating area at risk (proportion LV volume) and infarct size proportion of area at risk) after 120 min of reperfusion. † $p<0.001$ versus RI-Vehicle. Arrowheads denote the time of intracoronary injection of either vehicle or mitochondria.

FIG. 18F shows representative photograph of hearts stained with triphenyl tetrazolium, showing infarct sizes in RI-Vehicle and RI-Mitochondria groups.

DETAILED DESCRIPTION

Figure 1A:
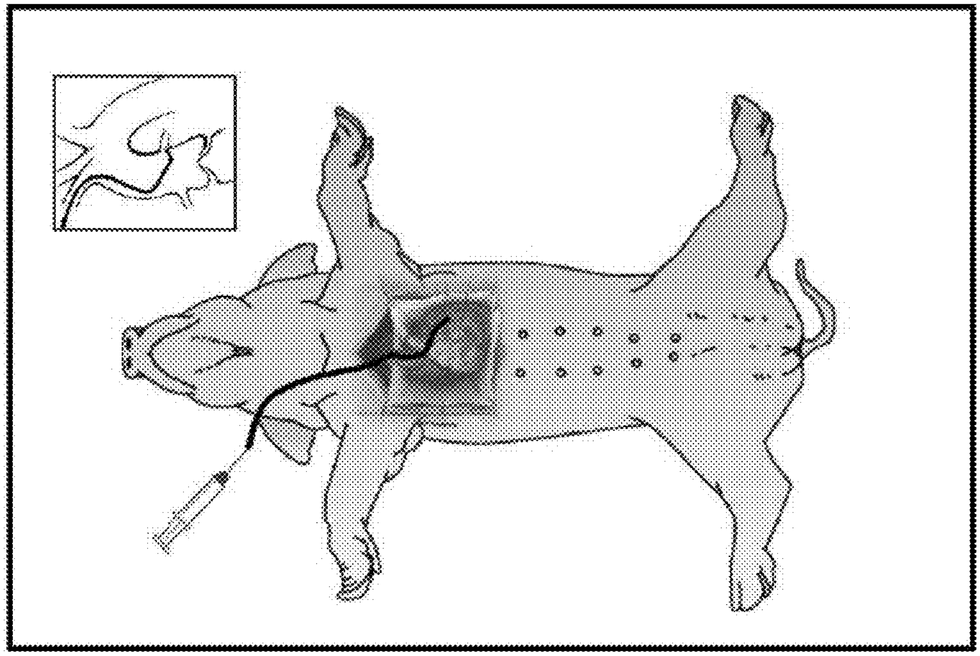
FIG. 1A shows a female Yorkshire pig sedated and intubated in a schematic diagram of one experimental model.

The present disclosure is based in part on the surprising discovery that mitochondria can be used to prevent, treat, and/or reduce one or more of the symptoms of ischemia-reperfusion injury (IRI), even before the IRI has occurred. Thus, in one aspect, the present disclosure provides methods of minimizing ischemia-reperfusion injury (IRI), reducing risk of IRI, ameliorating at least one symptom of IRI, preventing or treating cell damage, tissue damage, and/or organ damage associated with IRI, in a subject at risk of IRI. As used herein, the term "at risk of IRI" refers to an increased risk of IRI as compared to the risk of IRI for an average person in the population (e.g., within the same age group). In some embodiments, the risk is about or at least 50%, 60%, 70%, 80%, 90%, or 100% higher than the risk of IRI for an average person in the population. In some embodiments, the risk is about or at least 2, 3, 4, 5, 6, 7, 8, 9, 10 times higher than the risk of IRI for an average person in the population. This increased risk of IRI can be due to various factors, for example, genetic factors (e.g., genetic mutations), environmental factors (e.g., occupation risk, pollution), various diseases, medical procedures (e.g., surgery, organ/tissue transplantation), etc. Once a subject has been identified as having a risk of IRI, a therapeutically effective amount of composition as described herein can be administered to the subject to reduce the risk of IRI. In some embodiments, the risk arises from a potential medical procedure. As used herein, the term "medical procedure" refers to a course of action intended to achieve a result in the delivery of healthcare. The medical procedure can include e.g., diagnostic procedures, therapeutic procedures, and surgical procedures. Some medical procedures include e.g., extracorporeal membrane oxygenation (ECMO), chemotherapy, radiation therapy, tracheal intubation, gene therapy, anesthesia, ablation, amputation, cardiopulmonary resuscitation (CPR), cryosurgery, endoscopic surgery, hemilaminectomy, image-guided surgery, knee cartilage replacement therapy, laminectomy, laparoscopic surgery, lithotomy, lithotriptor, lobotomy, neovaginoplasty, radiosurgery, stereotactic surgery, vaginoplasty, transplantation (e.g., tissue or organ transplantation), xenotransplantation, etc. It is known that some medical procedures can increase the risk of IRI. In these cases, a therapeutically effective amount of composition as described herein can be administered to the subject before these procedures to minimize the risk.

Preventing and Treating IRI and Associated Tissue Damage

Ischemia-reperfusion is the interruption of blood flow to bodily tissue and the subsequent and often abrupt restoration of blood flow to the tissue. While restoration of blood flow following ischemia is essential to preserve functional tissue, the reperfusion itself is known to be harmful to the tissue. Both ischemia and reperfusion are known to be important contributors to tissue necrosis. Several mechanisms appear to play a causative role in the generation of tissue damage associated with ischemia-reperfusion injury.

In some embodiments, a composition of the present disclosure is useful for the prevention or reduction of tissue damage associated with an ischemia-reperfusion injury. In some embodiments, a composition of the present disclosure is useful for reduction or amelioration at least one symptom associated with an ischemia-reperfusion injury. The methods and compositions are useful for decreasing the morbidity and mortality for patients susceptible to or suffering from tissue damage associated with ischemia-reperfusion injury.

In some embodiments, a method comprises administering a therapeutically effective amount of mitochondria to a subject having or likely to incur tissue damage associated with ischemia-reperfusion injury. In some embodiments, the method comprises administering a therapeutically effective amount of mitochondria to a subject prior to IRI. In some embodiments, the method comprises administering a single dose of therapeutically effective amount of mitochondria to a subject prior to IRI. In some embodiments, the method comprises administering multiple doses of therapeutically effective amount of mitochondria to a subject prior to IRI. In some embodiments, the method comprises administering a series of doses of therapeutically effective amount of mitochondria to a subject prior to IRI.

The heart is a highly energetic organ that requires a continuous supply of oxygen to maintain normal function. Under aerobic conditions, the heart derives its energy primarily from the mitochondria, which constitute 30% of the total myocardial cell volume. Following the onset of ischemia, there is a rapid decline in high-energy phosphate levels with alterations in mitochondrial structure, volume, oxygen consumption, and ATP synthesis.

Attempts to lessen myocardial tissue necrosis and improve post-ischemic function using pharmacological and/or exogenous substrate interventions, either alone or in combination with procedural techniques, have provided only limited cardioprotection. Despite these interventions, mitochondrial damage and dysfunction continue to represent major problems following myocardial ischemia and remain significant causes of morbidity and mortality.

Without being bound by theory, mitochondrial damage occurs mainly during ischemia rather than during reperfusion, and preservation of mitochondrial respiratory function enhances contractile recovery and decreases myocardial infarct size.

Methods described herein can be used to treat, ameliorate at least one symptom of, reduce at least one symptom of, and/or prevent or treat tissue damage associated with ischemic heart, cardiac transplantation, cardiac infarction, procedures involving cross-clamp times, procedures involving heart with marginal function, procedures involving hearts with high risk of ischemia, interventional catheter-based procedures at high risk of ischemia, and procedures in which cardioplegic protection is not assured. For example, an effective amount of isolated mitochondria can be injected into the blood vessel of a subject, for example, the coronary vasculature of the subject. For example, about or at least $1\times10^9$ of mitochondria can be administered into the coronary vasculature of the subject. Without being bound by theory, the injected mitochondria are internalized by cardiomyocytes after administration and provide enhanced oxygen consumption, upregulate chemokines that enhance post-infarct cardiac function, and upregulate the expression of protein pathways that are important in preserving myocardial energetics. In another example, an effective amount of mitochondria can be directly injected to the area at risk (regional ischemic area). The injection can be repeated several times at different sites of the heart or at the same site.

Reperfusion injury is the tissue damage by blood supply when blood returns to the tissue after a period of ischemia or lack of oxygen. The absence of oxygen and nutrients during the ischemic period results in inflammation and oxidative damage when blood flow is restored. The inflammatory response further leads to the reperfusion injury in the tissue. Therefore, in some instances, a method of treatment also comprises administering immune suppressors to a subject. The immune suppressors can be, e.g., administrated separately, but as a concurrent treatment with the mitochondria or mitochondrial agent. In some embodiments, immune suppressors can be linked to mitochondria to form a combined mitochondrial agent, which can be used for a method of treatment. In some embodiments, useful immune suppressors are bisphosphonates.

The ischemia/reperfusion injury in other organs and tissues is often associated with mitochondrial damage and dysfunction as well. These organs and tissues include, but are not limited to, lung, kidney, liver, skeletal muscle, brain, pancreas, skin, eye, etc. These injuries or diseases include, but are not limited to, organ transplantation, organ failure, ischemic colitis, mesenteric ischemia, brain ischemia, aneurism, stroke, acute limb ischemia, cyanosis, gangrene, surgery involving cross-clamps, procedures with high risk of ischemia, and the like. In some embodiments, a method to treat ischemia injury or IRI in the lung, kidney, liver, skeletal muscle, brain, and the like, comprises administering mitochondria to a subject prior to ischemia or ischemic event. In some embodiments, the isolated mitochondria and/or combined mitochondrial agent is directly injected to the organ or tissue. In some embodiments, the isolated mitochondria and/or combined mitochondrial agent is injected into a blood vessel which carries the mitochondria and/or combined mitochondrial agent to the target organ/tissue or the injured site of a subject.

Heart IRI and Surgery

In some embodiments, mitochondria and/or combined mitochondrial agents can be administered to the heart prior to surgery or ischemia (pre-ischemic) to decrease stunning, allow for weaning of the heart from a surgical procedure (e.g., cardioplegia), improve recovery speed, decrease necrosis and/or tissue damage, improve global function, and improve regional function of the heart. In some embodiments, the method comprises administration of isolated mitochondria and/or combined mitochondrial agents to the heart prior to ischemia. In some embodiments, the method prevents, alleviates, or treats IRI-associated damage to the heart.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to surgery in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after the surgery.

Lung IRI and Surgery

In some embodiments, mitochondria and/or combined mitochondrial agents can be administered to a lung prior to surgery or ischemia (pre-ischemic) to decrease stunning, allow for weaning of the lung from a surgical procedure, improve recovery speed, decrease necrosis and/or tissue damage, improve global function, and improve regional function of the lung. In some embodiments, the method comprises administration of isolated mitochondria and/or combined mitochondrial agents to the lung prior to ischemia. In some embodiments, the method prevents, alleviates, or treats IRI-associated damage to the lung.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to surgery in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after the surgery.

Kidney IRI and Surgery

In some embodiments, mitochondria and/or combined mitochondrial agents can be administered to the kidney prior to surgery or ischemia (pre-ischemic) to decrease stunning, allow for weaning of the kidney from a surgical procedure, improve recovery speed, decrease necrosis and/or tissue damage, improve global function, and improve regional function of the kidney. In some embodiments, the method comprises administration of isolated mitochondria and/or combined mitochondrial agents to the kidney prior to ischemia. In some embodiments, the method prevents, alleviates, or treats IRI-associated damage to the kidney.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to surgery in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after the surgery.

Pancreas IRI and Surgery

In some embodiments, mitochondria and/or combined mitochondrial agents can be administered to the pancreas prior to surgery or ischemia (pre-ischemic) to decrease stunning, allow for weaning of the pancreas from a surgical procedure, improve recovery speed, decrease necrosis and/or tissue damage, improve global function, and improve regional function of the pancreas. In some embodiments, the method comprises administration of isolated mitochondria and/or combined mitochondrial agents to the pancreas prior to ischemia. In some embodiments, the method prevents, alleviates, or treats IRI-associated damage to the pancreas.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to surgery in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after the surgery.

Brain IRI and Surgery

In some embodiments, mitochondria and/or combined mitochondrial agents can be administered to the brain prior to surgery or ischemia (pre-ischemic) to decrease stunning, allow for weaning of the brain from a surgical procedure, improve recovery speed, decrease necrosis and/or tissue damage, improve global function, and improve regional function of the brain. In some embodiments, the method comprises administration of isolated mitochondria and/or combined mitochondrial agents to the brain prior to ischemia. In some embodiments, the method prevents, alleviates, or treats IRI-associated damage to the brain.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to surgery in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after the surgery.

Liver IRI and Surgery

In some embodiments, mitochondria and/or combined mitochondrial agents can be administered to the liver prior to surgery or ischemia (pre-ischemic) to decrease stunning, allow for weaning of the liver from a surgical procedure, improve recovery speed, decrease necrosis and/or tissue damage, improve global function, and improve regional function of the liver. In some embodiments, the method comprises administration of isolated mitochondria and/or combined mitochondrial agents to the liver prior to ischemia. In some embodiments, the method prevents, alleviates, or treats IRI-associated damage to the liver.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to surgery in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after the surgery.

Other IRI and Surgery

In some embodiments, mitochondria and/or combined mitochondrial agents can be administered to a subject prior to surgery or ischemia (pre-ischemic) to decrease stunning, allow for weaning of the organ or tissue from a surgical procedure, improve recovery speed, decrease necrosis and/or tissue damage, improve global function, and improve regional function of the organ or tissue. In some embodiments, the method comprises administration of isolated mitochondria and/or combined mitochondrial agents to an organ or tissue prior to ischemia. In some embodiments, the method prevents, alleviates, or treats IRI-associated damage to the organ or tissue. In some embodiments, the organ or tissue is selected from the group consisting of brain, thyroid, thymus, heart, lung, liver, pancreas, kidney, bladder, pharynx, esophagus, stomach, gallbladder, pharynx, larynx, ovaries, uterus, placenta, testes, prostate, spleen, spinal cord, pancreas, small intestine, large intestine, colon, eye, skin, skin tissue, skeletal muscle, adipose tissue, facial muscle, bone marrow tissue, eye tissue, heart valves, veins, tendons, and combinations thereof.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to surgery in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after the surgery.

Treating Diabetes and IRI Associated with Diabetes

In patients with type 1 (T1D) and type 2 diabetes mellitus (T2D), cardiovascular disease is the most common cause of death, 45% and 52%, respectively. In particular, diabetes mellitus is associated with micro- and macrovascular complications resulting in coronary heart disease and increased morbidity and mortality. Similarly, patients with diabetes mellitus are at high risk for peripheral arterial disease characterized by symptoms of intermittent claudication or critical limb ischemia (CLI). Diabetes is one of the major controllable risk factors for cardiovascular disease and is associated with long-term impairment of myocardial function and increases risk and susceptibility of the heart to ischemia-reperfusion injury (IRI). Both diabetes and IRI induce mitochondrial damage and dysfunction which lead to decreased functional recovery and cellular viability of the myocardium.

In some embodiments, the methods described herein provide a treatment of diabetes (T1D and/or T2D). In some embodiments, the methods described herein provide a way to prevent, alleviate at least one symptom of, and/or treat diabetes, T1D, and/or T2D. In some embodiments, the methods described herein provide a way to prevent, alleviate at least one symptom of, and/or treat IRI, ischemia, silent ischemia, and/or reperfusion associated with diabetes. In some embodiments, the methods described herein provide a way to minimize the risk of IRI, ischemia, silent ischemia, and/or reperfusion associated with diabetes. In some embodiments, the methods described herein provide a way to improve (e.g., shorten) recovery time following IRI, ischemia, silent ischemia, and/or reperfusion associated with diabetes.

"Silent ischemia" refers to the presence of objective findings suggestive of myocardial ischemia that is not associated with angina or anginal equivalent symptoms. Such objective evidence includes exercise testing or ambulatory monitoring demonstrating electrocardiographic changes, nuclear imaging studies demonstrating myocardial perfusion defects, or regional wall motion abnormalities illustrated by echocardiography.

In some embodiments, the methods comprise administering a composition comprising mitochondria and/or combined mitochondrial agents. In some embodiments, the composition can be administered to a subject having or at risk of having diabetes by e.g., injection intravenously, intra-arterially, intraperitoneally, intra-muscularly, intradermally, subcutaneously, and/or through intraosseous infusion.

Vasodilation and Blood Flow

It has been demonstrated that mitochondrial delivery by vascular infusion significantly increases coronary blood flow without altering mean blood pressure or heart rate. The ability to increase blood flow with no increase in heart rate allows for clinical usage in angina type injury and in ischemia/reperfusion related injury and in tissue damage areas where increased blood flow and oxygen delivery would be needed. Thus, the methods described herein can be used in coronary artery interventions to remove clots or obstructions in blood vessels.

Methods described herein can also be used to increase blood flow and/or oxygen delivery for various organs or tissues (e.g., heart, lung, kidney, brain, skeletal muscle). In some instances, methods described herein can be used to treat peripheral vascular disease. Peripheral vascular disease (PVD) is a blood circulation disorder that causes the blood vessels outside of the heart and brain to narrow, block, or spasm. This can happen in the arteries or veins. PVD typically causes pain and fatigue, often in the legs, and especially during exercise. Isolated mitochondria and/or combined mitochondrial agents can be injected to a blood vessel. Blood flow may carry isolated mitochondria or combined mitochondrial agents to the target site. In some instances, methods described herein can also be used to enhance smooth muscle function.

Methods described herein can also be used for vascular dilatation in various organs. In some instances, the isolated mitochondria or combined mitochondrial agents can be used to decrease vascular resistance in an organ (e.g., heart, kidney, liver, or lung). Isolated mitochondria or combined mitochondrial agents can be used to increased blood flow for angiography. The isolated mitochondria and/or combined mitochondrial agents can be added to a contrast agent, and can be used in the identification and removal of blockages.

Methods described herein can be used to treat a blocked blood vessel. The methods involve, e.g., the steps of localizing blood clots, positioning a first catheter with cage distal to clot, positioning a second catheter proximal to clot, injecting mitochondria and/or combined mitochondrial agents via the proximal catheter to cause vasodilatation, collecting the clot in a basket, and removing the clot.

It is noted that the effects of vascular infusion of mitochondria are dependent on time from isolation to time of use. The vasodilatory effects decreases as time from isolation is extended. While not intending to be bound by any theory, it is hypothesized that freshly isolated mitochondria have certain chemicals, which can increase blood flow. Therefore, in some methods, the mitochondria are freshly isolated and viable. For example, the mitochondria or combined mitochondrial agents are administered to a subject within about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes after the time point when the mitochondria isolation process starts or after the mitochondria are isolated. In some cases, the mitochondria or combined mitochondrial agents are administered to a subject within about 20 minutes to about 60 minutes (e.g., about 20 minutes, about 30 minutes, about 40 minutes, about 50 minutes, about 60 minutes) after the time point when the mitochondria isolation process starts or after the mitochondria are isolated.

In some cases, increasing blood flow is not desirable (e.g., treating ischemia/reperfusion in lungs). In these cases, mitochondria or combined mitochondrial agents can be stored for a short period of time (e.g., from about 30 to about 60 minutes) before usage. This method can be used to increase tissue viability (e.g., treating ischemia/reperfusion injury) without causing an increase in blood flow. In these cases, the mitochondria or combined mitochondrial agents are administered to a subject at least 60 about minutes (e.g., about 65 minutes, about 70 minutes, about 80 minutes, about 90 minutes, about 100 minutes, about 110 minutes, about 120 minutes) after the time point when the mitochondria isolation process starts or after the mitochondria are isolated.

Imaging

Imaging agents can be attached to mitochondria, often by co-incubation of the mitochondria with the imaging agents. Such imaging agents and methods of using agents for imaging purpose are well-known in the art and described in, for example, Bartholomä et al., Biological characterization of F18-labeled Rhodamine B, a potential positron emission tomography perfusion tracer, Nucl Med Biol 40, 1043-1048, PMC3820364 (2013); Bartholomä et al., $^{18}$F-labeled rhodamines as potential myocardial perfusion agents: comparison of pharmacokinetic properties of several rhodamines, Nucl Med Biol 42, 796-803, PMC4567415 (2015); and Pacak et al., Superparamagnetic iron oxide nanoparticles function as a long-term, multi-modal imaging label for non-invasive tracking of implanted progenitor cells, PLoS ONE 9, e108695, PMC4177390 (2014); and US20180057610A1. Each of the foregoing can be useful in methods described herein and is incorporated herein by reference its entirety.

Drug Delivery

The present specification provides methods to deliver pharmaceutic agents, e.g., to cells and/or tissues and/or organs of a subject. Without being bound by theory, mitochondria are taken up by tissue cells through an actin-dependent internalization process, thereby providing a way to deliver pharmaceutic agents directly into the cells. Moreover, because mitochondria and combined mitochondrial agents are more likely to cross the endothelium of the blood vessels near the injection site, in some instances, mitochondria and combined mitochondrial agents can be injected into a blood vessel that carries blood to the target site. In some instances, mitochondria and combined mitochondrial agents enter into tissue through the endothelium of capillaries.

In some embodiments, an antibody or an antigen-binding fragment can be linked or attached to mitochondria. Skilled practitioners will appreciate that linking the antibody or antigen binding fragment to mitochondria or combined mitochondrial agent can allow the mitochondria or combined mitochondrial agent to be targeted to specific sites, e.g., to target cells and/or tissues. In some instances, the antibody or the antigen-binding fragment are designed to target specific cell types, for example, smooth muscle cells in lung, immune cells, macrophages, etc. In some embodiments, mitochondria and/or mitochondrial agents are administered systemically.

Gene Therapy

Gene therapy is the therapeutic delivery of nucleic acid polymers into a patient's cells as a drug to treat disease. Isolated mitochondria can be used as a carrier to deliver nucleic acid polymers into a cell. In some instances, combined mitochondrial agents that include nucleic acid polymers can be administered to a subject to replace a mutated gene in the subject that causes disease, to inactivate, or "knock out," a mutated gene, or to introduce a new gene into the subject. Exemplary nucleic acid polymers include, but are not limited to, double-stranded DNA, single-stranded DNA, double-stranded RNA, single-stranded RNA, or triple helix nucleic acid molecules. In certain instances, the nucleic acid polymers are DNA, interfering RNAs (siRNA), and micro RNAs. In the case of mitochondrial myopathies related to mitochondrial DNA dysfunction, gene therapy can be performed by direct infusion of the mitochondria to a skeletal muscle or muscles. In the case of nuclear DNA related mitochondrial myopathies, multiple infusions over time might be beneficial or required.

Minimizing Cardiotoxicity

Chemotherapy is a common treatment for various cancers, however, it also causes several serious complications. Chemotherapy-induced cardiotoxicity is one complication that limits the clinical use of chemotherapeutic agents. Certain chemotherapeutic agents, such as anthracyclines, are highly effective against acute lymphoblastic and myeloblastic leukemias, but are particularly harmful to the heart due to its effects on mitochondria. The damage to mitochondria further leads to chemotherapy-induced cardiotoxicity. Angsutararux P, Luanpitpong S, Issaragrisil S. Chemotherapy-Induced Cardiotoxicity: Overview of the Roles of Oxidative Stress. Oxid Med Cell Longev. 2015; 2015:795602. doi: 10.1155/2015/795602 (2015); Guo S, Wong S. Cardiovascular toxicities from systemic breast cancer therapy, Front Oncol. 4:346. doi: 10.3389/fonc.2014.00346. eCollection (2014).

One useful method to minimize chemotherapy-induced cardiotoxicity is to administer an effective amount of isolated mitochondria and/or a combined mitochondrial agent to a patient who is currently under a chemotherapy treatment regimen. If the patient needs to be treated with chemotherapy (e.g., because prescribed by a physician or veterinarian), the patient can be treated with mitochondria and/or combined mitochondrial agent, before, during, and/or after administration of the chemotherapy. For example, patients can be treated with mitochondria and/or combined mitochondrial agent starting immediately after administration, as a singular treatment or continuing intermittently or continuously for about 1, 2, 5, 8, 10, 20, 30, 50, or 60 days, one year, indefinitely, or until a physician determines that administration of the mitochondria and/or combined mitochondrial agent is no longer necessary.

Organ/Tissue Transplantation

The present disclosure also features methods of transplanting an organ(s), tissues, masses of cells and/or isolated cells. The methods can include a step of exposing the organ(s), tissues, mass of cells and/or isolated cells to mitochondria or combined mitochondrial agents prior to transplantation. Such exposures can occur in situ and/or ex vivo. The organ(s), tissues and/or isolated cells may be exposed to a composition comprising mitochondria or combined mitochondrial agents.

Exposure of an organ or tissue to compositions comprising mitochondria or combined mitochondrial agents can be performed ex vivo and/or in situ by any method known in the art. For example, the exposure may be performed ex vivo in any chamber or space having sufficient volume for submerging the organ or tissue, completely or partially, in the composition. As another example, the organ may be exposed to compositions comprising mitochondria or combined mitochondrial agents by placing the organ in any suitable container, and causing the compositions comprising mitochondria or combined mitochondrial agents to "wash over" the organ, such that the organ is exposed to a continuous flow of the composition.

In some embodiments, the organ may be perfused with a composition comprising mitochondria or combined mitochondrial agents. The term "perfusion" is an art recognized term, and relates to the passage of a liquid, e.g., a composition comprising mitochondria or combined mitochondrial agents, through the blood vessels of an organ or tissue. Methods for perfusing organs ex vivo and in situ are well known in the art. An organ can be perfused with a composition ex vivo, for example, by continuous hypothermic machine perfusion (see *Oxford Textbook of Surgery*, Morris and Malt, Eds., Oxford University Press, 1994). Optionally, in in situ or ex vivo perfusions, the organ can be perfused with a wash solution, e.g., UW solution, prior to perfusion with a composition comprising mitochondria or combined mitochondrial agents, to remove the donor's blood from the organ. As another option, the UW solution can include mitochondria or combined mitochondrial agents.

The organ or tissue may be placed, e.g., submerged, in a medium or solution that includes mitochondria or combined mitochondrial agents. Alternatively, or in addition, mitochondria or combined mitochondrial agents can be added into the medium or solution. In situ exposures can be performed by any method known in the art, e.g., by in situ flushing or perfusion of the organ with a composition comprising mitochondria or combined mitochondrial agents (see *Oxford Textbook of Surgery*, Morris and Malt, Eds., Oxford University Press, 1994).

The present disclosure contemplates that any or all of the above methods for exposing an organ or tissue to a composition comprising mitochondria or combined mitochondrial agents, e.g., washing, submerging, or perfusing, can be used in a given transplantation procedure.

The present disclosure further contemplates that a solid or semi-solid composition can be created. For example, a liquid that is a composition comprising mitochondria or combined mitochondrial agents, as described above, can be made into a solid or semi-solid composition, in which an organ or tissue may be overlaid or embedded. Alternatively, a semi-solid composition can be infused into the organ. Solid or semi-solid compositions can be made, for example, by adding a solidifying agent such as a gelling agent (e.g., collagen or alginate) to the liquid.

Methods described herein can be used to control, prevent, reduce, and/or treat IRI damage for transplanted organs. Ischemia-reperfusion injury is a very important problem during organ transplantation. Much damage in organ transplantation appears to be induced by IRI. Organs used for transplantation often undergoe lengthy periods of cold ischemic storage after devascularization and cold perfusion, resulting in an increased susceptibility to damage upon reperfusion. Evidence shows that ischemia/reperfusion injury often leads to mitochondrial oxidative damage, which may cause delayed graft function. Dare A J, Logan A, Prime T A, Rogatti S, Goddard M, Bolton E M, Bradley J A, Pettigrew G J, Murphy M P, Saeb-Parsy K. The mitochondria-targeted anti-oxidant MitoQ decreases ischemia-reperfusion injury in a murine syngeneic heart transplant model, J Heart Lung Transplant, 34(11):1471-80. doi: 10.1016/j.healun.2015.05.007 (2015); Liu Q, Krishnasamy Y, Rehman H, Lemasters J J, Schnellmann R G, Zhong Z. Disrupted Renal Mitochondrial Homeostasis after Liver Transplantation in Rats. PLoS One 10(10):e0140906. doi: 10.1371/journal.pone.0140906 (2015). In some embodiments, the transplanted organ can be, e.g., a heart, a lung, a kidney, a pancreas, or a liver. In one embodiment, an effective amount (e.g., $1\times10^7$, $1\times10^8$, $1\times10^9$, $1\times10^{10}$) of mitochondria or combined mitochondria agents are injected into the blood vessels (e.g., arteries) of the transplanted organ. In another embodiment, an effective amount (e.g., $1\times10^7$, $1\times10^8$, $1\times10^9$, $1\times10^{10}$) of mitochondria or combined mitochondria agents are directly injected into the organ tissue.

An effective amount or therapeutically effective amount of mitochondria or combined mitochondria agents is an amount that is effective for enhancing survival and/or improving function of organs, or cells in vivo and/or in vitro. Within the context of transplantation of individual cells or masses of cells, e.g., transplant donors and/or recipients, an effective amount of mitochondria or combined mitochondria agents is an amount that is administered to the transplant donor and/or recipient sufficient to enhance survival of the cell or mass of cells, e.g. to reduce loss of the cell, or mass of cells, and/or to improve functional performance of a transplanted cell or a mass of cells. Within the context of treating cells outside a body, e.g., islet cells to be cultured and/or used for transplantation, an effective amount is an amount with which the cells are incubated or stored in order to enhance preservation of the cells and/or to reduce cell loss, e.g., loss via apoptosis, and/or to enhance function. Within the context of transplantation of organs and tissues, e.g., transplant donors and/or recipients, an effective amount of mitochondria or combined mitochondria agents is an amount that is administered to the transplant donor and/or recipient sufficient to enhance survival of the organ, tissue or cells of interest, e.g., to reduce loss of cells from which the organ or tissue is composed, and/or to improve functional performance of an organ.

In some instances, the injection is performed before the organ is retrieved from the donor. In some instances, the injection is performed at some time point after organ is retrieved, but before it is transplanted. In some instances, the injection is performed after the organ is transplanted into the recipient. In some instances, injections are performed before organ retrieval, after harvesting of the organ, and then again after implantation into the recipient. In some instances, the injection is performed during the transplantation surgery. In some embodiments, the transplanted organ is preserved in a solution containing an effective amount of isolated mitochondria or combined mitochondrial agents. In some cases, the solution is University of Wisconsin cold storage solution.

A major limitation for organ transplantation is the availability of donor organs. In order to expand the number of donor organs, centers may use organs from donors with extended criteria or donors from cardiac death. In these cases, the described methods can improve the quality of the organs, thus increasing the availability of donor organs.

The disclosure also provides methods of improving transplanted tissue and/or cell integration. In some embodiments, the tissue is skin tissue or bone marrow. In some embodiments, the cells are stem cells. In these cases, mitochondria or combined mitochondrial agents can improve the integration of the transplanted tissue and cells in the recipient's body.

In some embodiments, these methods can be used to control, prevent, reduce, and/or treat IRI damage for transplanted organs and tissues, including but not limited to heart, brain, liver, kidney, lung, pancreas, eye, skeletal muscle, and skin. In some embodiments, the organ or tissue is selected from the group consisting of brain, thyroid, thymus, heart, lung, liver, pancreas, kidney, bladder, pharynx, esophagus, stomach, gallbladder, pharynx, larynx, ovaries, uterus, placenta, testes, prostate, spleen, spinal cord, pancreas, small intestine, large intestine, colon, eye, skin, skin tissue, skeletal muscle, adipose tissue, facial muscle, bone marrow tissue, eye tissue, heart valves, veins, tendons, and combinations thereof.

Treating Mitochondrial Dysfunction Disorder

Due to mitochondria's primary function in cell metabolism, damage and dysfunction in mitochondria can cause a range of human diseases. Diseases caused by mutation in the mtDNA include Kearns-Sayre syndrome, MELAS syndrome and Leber's hereditary optic neuropathy, Pearson syndrome, and progressive external ophthalmoplegia. Other diseases that involve mitochondrial dysfunction include, but are not limited to, mitochondrial myopathy, diabetes mellitus and deafness (DAD), Leigh syndrome, "Neuropathy, ataxia, retinitis pigmentosa, and ptosis" (NARP), myoneurogenic gastrointestinal encephalopathy (MNGIE), Myoclonic Epilepsy with Ragged Red Fibers (MERRF syndrome), encephalomyopathy, lactic acidosis, Parkinson's disease, and stroke-like symptoms (MELAS syndrome), etc.

Furthermore, damage and dysfunction in mitochondria can also be caused by injury, toxicity, chemotherapy, and age-related changes. The mitochondrial dysfunction may further interfere with the proper function of the tissue or the organ of a subject.

The disclosure indicates that mitochondrial transplantation has potential to rescue cell function and replace damaged or dysfunctional mitochondria. As mitochondria can be effectively delivered to tissues through blood vessel infusion, methods described here relate to a novel method to treat mitochondrial dysfunction disorder.

The mitochondria for the treatment can be isolated from cells of an autogenous source, an allogeneic source, and a xenogeneic source. The goal is to administer enough functional mitochondria to the subject to obtain the desired therapeutic effect. In one embodiment, isolated mitochondria or combined mitochondrial agents are administered to a patient in an amount sufficient to treat the mitochondrial dysfunction disorder. Because the symptoms for mitochondrial dysfunction disorder is more likely to manifest at an organ that requires a continuous supply of energy, the administration can specifically target these affected organs, such as the heart, the brain and the liver. In one embodiment, the injection site is the blood vessel which carries the blood to the target organ. In another embodiment, the treatment involves systemic administration.

The methods described herein provide a way to treat diabetes mellitus. Some forms of diabetes are caused by mitochondrial dysfunction in beta cells. At the islet β-cell level, acute insulin release is regulated by mitochondrial ATP production and mitochondrial ROS may contribute to the long-term deterioration of insulin secretory capacity seen in type 2 diabetes. Mitochondrial function also appears a critical determinant of insulin sensitivity within muscle, liver, and adipose tissue. Sivitz, William I., and Mark A. Yorek. "Mitochondrial dysfunction in diabetes: from molecular mechanisms to functional significance and therapeutic opportunities." Antioxidants & redox signaling 12.4 (2010): 537-577. Treating these patients with isolated mitochondria or combined mitochondrial agents can restore the normal function of beta cells, thereby improving insulin production. In some embodiments, the methods involve administering an effective amount of a composition comprising isolated mitochondria or combined mitochondrial agents to patients. The composition can be administered to the patient by various routes, e.g., the composition can be directly injected into the pancreases tissue, alternatively, the composition can be injected into a blood vessel that carries the blood the pancreas. In some cases, the blood vessel is a pancreatic artery, e.g., greater pancreatic artery. In some embodiments, islet β-cells are treated with isolated mitochondria or combined mitochondrial agents, and then are transferred to a subject. These islet β-cells can come from the same subject, or from a different subject.

In addition, the methods described herein provide a way to treat Parkinson's disease. Parkinson's disease results from the dysfunction or the death of dopamine-generating cells in the substantia nigra. The causes of the cell dysfunction or the cell death are poorly understood. Evidence suggests that reduced mitochondrial activity or mitochondrial dysfunction may be part of the causes. Therefore, administering an effective amount of isolated mitochondria or combined mitochondrial agents to patients with Parkinson's disease can restore the normal function of dopamine-generating cells in these patients, thereby improving dopamine production.

Furthermore, mitochondrial dysfunctions are increasingly recognized as key components in stress-related mental disorders (e.g., post-traumatic stress disorder (PTSD)). The relationship between stress-related mental disorders and mitochondrial dysfunctions is described, e.g., in Flaquer, A., et al. "Mitochondrial genetic variants identified to be associated with posttraumatic stress disorder." Translational psychiatry 5.3 (2015): e524. Thus, in some cases, a stress-related mental disorder is also a mitochondrial dysfunction disorder. Thus, the methods described herein can also be used to treat a stress-related mental disorder, e.g., PTSD.

Treating Metabolic Disorders

White adipose tissue or white fat is one of the two types of adipose tissue found in mammals. It is often used by the body as a store of energy, and includes many white adipocytes. The other kind of adipose tissue is brown adipose tissue. The function of brown adipose tissue is to transfer energy from food into heat.

White adipocytes often contain a single lipid droplet. In contrast, brown adipocytes contain numerous smaller droplets and a much higher number of mitochondria. With the recognition that adult humans have in brown adipose tissue an organ with substantial capacity to dissipate energy, targeting brown adipose tissue thermogenesis is now viewed as a way to treat or prevent metabolic disorders, such as obesity and its associated metabolic diseases (e.g., type II diabetes). The use of brown adipose tissue to treat obesity and diabetes is described, e.g., in Cypess, Aaron M., and C. Ronald Kahn. "Brown fat as a therapy for obesity and diabetes." Current opinion in endocrinology, diabetes, and obesity 17.2 (2010): 143, which is incorporated by reference in its entirety.

As one major difference between brown adipocytes and white adipocytes is the number of mitochondria in the cell, the present disclosure provides methods of treating and preventing metabolic disorders. These metabolic disorders include, but are not limited to, obesity and its associated metabolic diseases (e.g., type II diabetes). In some embodiments, isolated mitochondria and/or combined mitochondrial agents can be directed injected into white adipose tissue in the subject. In some embodiments, the methods involving identifying a subject having or being at risk of a metabolic disorder, and delivering mitochondria or combined mitochondrial agents to the white adipose tissue by various routes (e.g., direct injection, or inject mitochondria or combined mitochondrial agents into a blood vessel, which carries blood to the white adipose tissue). In some embodiments, the methods described herein can convert white adipocytes to brown adipocytes, thus converting white adipose tissue to brown adipose tissue.

Isolated mitochondria and/or combined mitochondrial agents can be administered to a subject by focal delivery. In some embodiments, the methods involve locating the target site (e.g., fat tissue under the chin, and abdomen fat tissue), and injecting a composition comprising isolated mitochondria and/or combined mitochondrial agents to the target site. In some cases, a small amount of the composition is delivered in each injection, but the injection is repeated several times until the amount is sufficient to bring a desired effect.

In Vitro Fertilization

The mitochondrial genes are not inherited by the same mechanism as nuclear genes. They are typically inherited from one parent only. In humans, the mitochondria come from the egg, thus the mother. Mitochondrial donation is a specialized form of in vitro fertilization to prevent the mother's mutated mitochondrial genes from being passed to the baby. Usually, the future baby's mitochondrial DNA comes from an egg of a third party. One prominent problem of such procedure is that it results in a human offspring with three genetic parents. It leads to considerable controversy in the field of bioethics.

The described method provides a method to solve this issue. In one embodiment, the future father's cells are collected and cultured. Mitochondria are then isolated from the cultured cells. These mitochondria are then co-incubated with a mitochondria-depleted egg, which is prepared for in vitro fertilization. In another embodiment, the father's mitochondria are co-incubated with the egg, and in some instances, the embryo. In these cases, even though the mother's mutated mitochondria have not been removed, as long as there is a sufficient amount of functional and viable mitochondria in the egg or in the embryo, the baby may be treated for mitochondrial disease.

Combined Mitochondrial Agents

Combined mitochondrial agents include mitochondria that are physically associated with an agent, such as a therapeutic agent, a diagnostic agent, and/or an imaging agent.

A therapeutic agent can be any agent that has a therapeutic or prophylactic use. Exemplary therapeutic agents include, e.g., therapeutic agents for ischemia-related disorders, cytotoxic agents for treating cancer, among many others. In some instances, mitochondria can deliver therapeutic agents to specific cells, for example, tumor cells. The therapeutic agent may be, e.g., an intracellular inhibitor, deactivator, toxin, arresting substance and/or cytostatic/cytotoxic substance that, once inside a cell, inhibits, destroys, arrests, modifies and/or alters the cell such that it can no longer function normally and/or survive. The therapeutic agent can be an agent to restore a cell's proper function, for example, a DNA vector for gene therapy. A therapeutic agent can be, e.g., an inorganic or organic compound; a small molecule (less than 500 daltons) or a large molecule; a proteinaceous molecule, such as a peptide, polypeptide, protein, post-translationally modified protein, or antibody; or a nucleic acid molecule, such as a double-stranded DNA, single-stranded DNA, double-stranded RNA, single-stranded RNA, or a triple helix nucleic acid molecule. In some embodiments, a therapeutic agent can be a natural product derived from any known organism (e.g., from an animal, plant, bacterium, fungus, protist, or virus) or from a library of synthetic molecules. In some embodiments, a therapeutic agent can be a monomeric or a polymeric compound. Some exemplary therapeutic agents include cytotoxic agents, DNA vectors, small interfering RNAs (siRNA), micro RNAs (miRNA), reactive peptides, nanoparticles, microspheres, and fluorescent molecules.

Additional mitochondrial agents, and variants and combinations thereof, and methods of making them, are disclosed in US Publication US20180057610-A, which is herein incorporated by reference in its entirety for any and all purposes.

Methods of Making Compositions Comprising Mitochondria and/or Combined Mitochondrial Agents Isolating Mitochondria Mitochondria for use in the presently described methods can be isolated or provided from any source, e.g., isolated from cultured cells or tissues. Exemplary cells include, but are not limited to, muscle tissue cells, cardiac fibroblasts, cultured cells, HeLa cells, prostate cancer cells, yeast, among others, and any mixture thereof. Exemplary tissues include, but are not limited to, liver tissue, skeletal muscle, heart, brain, kidney, and adipose tissue. Mitochondria can be isolated from cells of an autogenous source, an allogeneic source, and/or a xenogeneic source. In some instances, mitochondria are isolated from cells with a genetic modification, e.g., cells with modified mtDNA or modified nuclear DNA.

Mitochondria can be isolated from cells or tissues by any means known to those of skill in the art. In one embodiment, tissue samples or cell samples are collected and then homogenized. Following homogenization, mitochondria are isolated by repetitive centrifugation. Alternatively, the cell homogenate can be filtered through nylon mesh filters. Additional methods of isolating mitochondria are described, for example, in McCully J D, Cowan D B, Pacak C A, Toumpoulis I K, Dayalan H and Levitsky S, Injection of isolated mitochondria during early reperfusion for cardioprotection, Am J Physiol 296, H94-H105. PMC2637784 (2009); Frezza, C., Cipolat, S., & Scorrano, L, Organelle isolation: functional mitochondria from mouse liver, muscle and cultured filroblasts. Nature protocols, 2(2), 287-295 (2007); and a PCT application entitled "Products and Methods to Isolate Mitochondria" (PCT/US2015/035584; WO 2015192020); each of which is incorporated by reference in their entirety for any and all purposes.

Methods of Preparing Compositions Comprising Mitochondria and/or Combined Mitochondrial Agents Isolated mitochondria and combined mitochondrial agents can be mixed with a pharmaceutically acceptable carrier to make a pharmaceutic composition. A pharmaceutically acceptable carrier includes any compound or composition useful in facilitating storage, stability, administration, cell targeting and/or delivery of the mitochondria and/or combined mitochondrial agent, including, without limitation, suitable vehicles, diluents, solvents, excipients, pH modifiers, salts, colorants, rheology modifiers, lubricants, coatings, fillers, antifoaming agents, polymers, hydrogels, surfactants, emulsifiers, adjuvants, preservatives, phospholipids, fatty acids, mono-, di- and tri-glycerides and derivatives thereof, waxes, oils and water. In some embodiments, isolated mitochondria and/or the combined mitochondrial agents are suspended in water, saline, buffer, respiration buffer, or sterile mitochondria buffer for delivery in vivo. Pharmaceutically acceptable salts, buffers or buffer systems, including, without limitation, saline, phosphate buffer, phosphate buffered saline (PBS) or respiration buffer can be included in a composition described herein. Vehicles having the ability to facilitate delivery to a cell in vivo, such as liposomes, may be utilized to facilitate delivery of the combined mitochondrial agents to the target cells.

Methods of making compositions, e.g., liquid, semi-solid, and solid compositions (e.g., liquids, creams, lotions, ointments, oils, among others), are well-known in the art. Skilled practitioners will appreciate that such known methods can be modified to add one or more steps to add mitochondria and/or combined mitochondrial agents and form a composition described herein. Skilled practitioners will appreciate that in some instances a composition described herein may include more than one type of combined mitochondrial agent. For example, included are compositions comprising mitochondria wherein essentially each mitochondrion is associated with multiple types of agents. Also included are compositions comprising mitochondria wherein each mitochondrion is paired with only one type of agent but wherein the composition comprises a mixture of mitochondria/agent pairings.

Pharmaceutical and Other Compositions

The disclosure provides compositions that comprise isolated mitochondria, compositions that comprise combined mitochondrial agents, compositions that comprise both isolated mitochondria and combined mitochondrial agents, and methods of using such compositions.

A pharmaceutical composition described herein may include mitochondria and/or combined mitochondria agents and a pharmaceutically acceptable carrier. As used herein, the language "pharmaceutically acceptable carrier" includes saline, solvents, dispersion media, coatings, antibacterial and antifungal agents, isotonic and absorption delaying agents, and the like, compatible with pharmaceutical administration. In some embodiments, the pharmaceutically acceptable carrier is phosphate buffered saline, saline, Krebs buffer, Tyrode's solution, contrast media, or omnipaque, or a mixture thereof. In some embodiments, the pharmaceutically acceptable carrier is sterile mitochondria buffer (300 mM sucrose; 10 mM K+-HEPES (potassium buffered (4-(2-hydroxyethyl)-1-piperazineethanesulfonic acid, pH 7.2);

1 mM K+-EGTA, (potassium buffered ethylene glycol tetraacetic acid, pH 8.0)). In some embodiments, the pharmaceutically acceptable carrier is respiration buffer (250 mM sucrose, 2 mM $KH_2PO_4$, 10 mM $MgCl_2$, 20 mM K-HEPES Buffer (pH 7.2), and 0.5 mM K-EGTA (pH 8.0)).

Pharmaceutical compositions are typically formulated to be compatible with its intended route of administration. Examples of routes of administration include parenteral, intravenous, intradermal, intramuscular, intraarticular, intracardiac, subcutaneous, oral (e.g., inhalation), sublingual, transdermal (e.g., topical), transmucosal, rectal administration, and the like.

A pharmaceutical composition can be formulated for various clinical uses, e.g., imaging, treating wounds, treating injuries, preserving organs, improving mitochondrial functions in organs or tissues, and skin care. In some cases, the pharmaceutically acceptable carrier is a contrast agent for imaging purpose. In some embodiments, the pharmaceutical composition may include antiseptic agents, antibacterial agents (e.g., antibiotics), antifungal agents, disinfectants, analgesic agents, anesthetic agents, steroids, nutritional supplements, ethereal oils, etc. An anesthetic agent is a drug that can prevent pain during surgery or treatment. Exemplary analgesic agents include, without limitation, paracetamol, nonsteroid anti-inflammatory drugs, salicylates, ibuprofen and lidocaine. Exemplary antibacterial agents include, without limitation, dichlorobenzyl alcohol, amylmetacresol and antibiotics. Exemplary antibiotics include penicillins carbapenems, cephalosporins aminoglycosides, bacitracin, gramicidin, mupirocin, chloramphenicol, thiamphenicol, lincomycin, clindamycin, macrolides, novobiocin, polymyxins, rifamycins, spectinomycin, tetracyclines, vancomycin, teicoplanin, streptogramins, anti-folate agents, sulfonamides, trimethoprim, pyrimethamine, nitrofurans, methenamine mandelate, methenamine hippurate, nitroimidazoles, quinolones, fluoroquinolones, isoniazid, ethambutol, pyrazinamide, para-aminosalicylic acid, cycloserine, capreomycin, ethionamide, prothionamide, thiacetazone and viomycin. Antiseptic agents are antimicrobial substances that can be applied to living tissue/skin to reduce the possibility of infection, sepsis, or putrefaction. Exemplary antiseptics include, without limitation, chlorhexidine and salts thereof, benzalkonium and salts thereof, triclosan and cetylpyridium chloride. Exemplary antifungal agents include, without limitation, tolnaftate, miconazole, fluconazole, clotrimazole, econazole, ketoconazole, itraconazole, terbinafine, amphotericin, nystatin and natamycin. Exemplary steroids include, without limitation, prednisone acetate, prednisone valerate, prednisolone, alclometasone dipropionate, fluocinolone acetonide, dexamethasone, methylprednisolone, desonide, pivolate, clocortolone pivolate, triamcinolone acetonide, prednicarbate, fluticasone propionate, flurandrenolide, mometasone furoate, desoximetasone, betamethasone, betamethasone dipropionate, betamethasone valerate, betamethasone propionate, betamethasone benzoate, diflorasone diacetate, fluocinonide, halcinonide, amcinonide, halobetasol propionate, and clobetasol propionate. Exemplary nutritional supplements include, without limitation, vitamins, minerals, herbal products and amino acids. Vitamins include without limitation, vitamin A, those in the vitamin B family, vitamin C, those in the vitamin D family, vitamin E and vitamin K. Ethereal oils include without limitation, those derived from mint, sage, fir, lavender, basil, lemon, juniper, rosemary, eucalyptus, marigold, chamomile, orange and the like. Many of these agents are described, e.g., in WO 2008152626, which is incorporated by reference in its entirety for any and all purposes.

Compositions comprising mitochondria and/or combined mitochondrial agents can be formulated in any form, e.g., liquids, semi-solids, or solids. Exemplary compositions include liquids, creams, ointments, salves, oils, emulsions, liposome formulations, among others.

Compositions for Transplantation

Isolated mitochondria or combined mitochondrial agents can be included in compositions that are designed for use in organ, tissue, or cell transplantation. The composition may include isolated mitochondria and/or combined mitochondrial agents and a liquid that is suitable for administration to patients and/or organs in situ or ex vivo, e.g., for maintaining organs, tissues or cells ex vivo. In general, the liquid will be an aqueous solution. Examples of solutions include Phosphate Buffered Saline (PBS), Celsior™ solution, Perfadex™ solution, Collins solution, citrate solution, tissue culture media (e.g., Dulbecco's Modified Eagle's Medium (DMEM)), the Histidine-tryptophan-ketoglutarate (HTK) solution, and the University of Wisconsin (UW) solution (Oxford Textbook of Surgery, Morris and Malt, Eds., Oxford University Press, 1994).

The University of Wisconsin cold storage solution is considered a standard solution for organ transplantation. It includes the following: 100 mM potassium lactobionate, 25 mM $KH_2PO_4$, 5 mM $MgSO_4$, 30 mM raffinose, 5 mM adenosine, 3 mM glutathione, 1 mM allopurinol, and 50 g/L hydroxyethyl starch. Isolated mitochondria or combined mitochondrial agents can be added to these liquids for organ, tissue and cell preservation.

Blood Products

Mitochondria and/or combined mitochondrial agents can be included in compositions that include blood and/or or products derived from blood. In some embodiments, the composition can include mitochondria and/or mitochondrial agents and blood, e.g., whole blood, serum, one or more individual blood components, and/or an artificial blood substitute. In some cases, these blood products can be administered to a subject, and the mitochondria in the blood products can improve the mitochondrial function in the subject. For example, such blood products can be administered to a patient as a part of a blood transfusion procedure. As is art-known, blood or blood products can be stored in any number of vessels, e.g., in blood bags, ampules, and/or vials. In some embodiments, the mitochondria and/or mitochondrial agents can be isolated from blood cells.

Administration

Isolated mitochondria, and/or isolated mitochondria linked to a therapeutic agent, diagnostic agent and/or imaging agent, can be delivered to a patient's tissue by injecting them into the patient's blood vessels. Skilled practitioners can locally and/or generally distribute mitochondria to tissues and/or cells of a patient for a variety of purposes, using relatively simple medical procedures. Further, mitochondria can be used as carrier agents, e.g., to deliver therapeutic, diagnostic, and/or imaging agents, to a patient's tissues. Compared to some traditional therapeutic regimens that involve nanoparticles, it is further noted that mitochondria are not toxic and do not cause any substantial adverse immune or auto-immune response. Without being bound by any theory, it is believed that infused mitochondria extravasate through the capillary wall by first adhering to the endothelium. After they are injected or infused into an artery, mitochondria can cross the endothelium of the blood vessels and be taken up by tissue cells through an endosomal actin-dependent internalization process.

Isolated mitochondria and combined mitochondrial agents can be administered to a patient by injection intravenously, intra-arterially, intraperitoneally, intra-muscularly, intradermally, subcutaneously, and/or through intraosseous infusion. In some embodiments, isolated mitochondria and combined mitochondrial agents can be delivered by direct injection or by vascular infusion. In some embodiments, administration can be parenteral, intravenous, intradermal, intramuscular, intraarticular, intracardiac, subcutaneous, oral, inhalation, sublingual, transdermal (e.g., topical), transmucosal, or rectal. In some embodiments, isolated mitochondria or the combined mitochondrial agents are in an aerosol form and can be administered to a patient by a nebulizer, a vaporizer, a nasal sprayer, an inhaler, a soft mist inhaler, a jet nebulizer, an ultrasonic wave nebulizer, a pressurized metered dose inhaler, a breath activated pressurized metered dose inhaler, or a vibrating mesh device.

Once mitochondria are injected into a tissue, mitochondria will be taken up by cells around the site of injection. Therefore, in some embodiments, the site of injection is the target site. In some other embodiments, mitochondria are injected to a blood vessel which carries the blood to the target site, for example, an organ, a tissue, a cell, or an injured site. While not intending to be bound by any theory, evidence suggests that mitochondria delivered by direct injection are internalized by cells through actin-dependent endocytosis. However, mitochondrial uptake by vascular delivery appears to be more complicated. The rapid and widespread uptake of mitochondria when delivered by vascular infusion would suggest that mechanisms allowing for the rapid passage of mitochondria through the vascular wall may be involved. Some studies support the concept that cells can routinely escape from the circulation. It has been shown that certain cardiac and mesenchymal stem cells appear to be actively expelled from the vasculature in a process different from diapedesis (Cheng, K., Shen, D., Xie, Y., Cingolani, E., Malliaras, K., Marbán, E., 2012, Brief report: Mechanism of extravasation of infused stem cells. Stem Cells. 30, 2835-2842.; Allen, T. A., Gracieux, D., Talib, M., Tokarz, D. A., Hensley, M. T., Cores, J., Vandergriff, A., Tang, J., de Andrade, J. B., Dinh, P. U., Yoder, J. A., Cheng, K., 2017. Angiopellosis as an Alternative Mechanism of Cell Extravasation. Stem Cells. 35, 170-180). Transmigration of stem cells through the vascular wall requires extensive remodeling of the endothelium. Mitochondria may use a similar remodeling mechanism to pass through the vascular wall. Another possible mechanism for mitochondrial uptake may be diapedesis-like. Some cells routinely escape from the circulation. For example, leukocyte extravasation (i.e. diapedesis) between venous endothelial cells is a well-understood process that involves cell adhesion proteins. Further, it may also be possible that infused mitochondria extravasate through the capillary wall through the space between the endothelium cells. After mitochondria cross the endothelium of the blood vessels, mitochondria may be taken up by tissue cells through an endosomal actin-dependent internalization process.

Mitochondria or combined mitochondrial agents can be administered to a subject as a singular, one-time treatment, or alternatively, multiple treatments, e.g., a treatment course that continues intermittently or continuously for about 1, 2, 5, 8, 10, 20, 30, 50, or 60 days, one year, indefinitely, or until a physician determines that administration of the mitochondria or combined mitochondrial agent is no longer necessary.

In one method of administration, mitochondria or combined mitochondrial agents are injected into organ tissue directly. The injection is repeated several times at different sites of the organ. In such a method, a sterile 1-ml insulin syringe with a small needle (e.g., 28-gauge) can be used for the injection and each injection site can receive, e.g., about or at least $1.2\times10^6$ of mitochondria.

Skilled practitioners will appreciate that the amount of mitochondria and/or combined mitochondrial agents, e.g., compositions comprising mitochondria and/or combined mitochondrial agents, that should be administered to a patient will vary depending upon, e.g., the type of disorder being treated, the route of administration, the duration of the treatment, the size of an area to be treated, and/or the location of the treatment site in the patent, among others. Skilled practitioners will be able to determine dosages to be administered depending on these and other variables.

In some embodiments, a composition comprising about or at least $1\times10^6$, $1\times10^7$, $1\times10^8$, $1\times10^9$, $1\times10^{10}$, or $1\times10^{11}$ of mitochondria can be administered to a subject, e.g., to treat localized ischemia in the myocardium. In other embodiments, e.g., in the case of larger organs or affected areas, a composition comprising about or at least $1\times10^{10}$, $1\times10^{11}$, $1\times10^{12}$, $1\times10^{13}$, $1\times10^{14}$, or $1\times10^{15}$ mitochondria can be administered to a subject. In other embodiments, e.g. in the case of small regional or focal lesions, a composition comprising about or at least $1\times10^3$, $1\times10^4$, $1\times10^5$, $1\times10^6$, $1\times10^7$, or $1\times10^8$ mitochondria can be administered a subject. In some embodiments, an effective amount or therapeutically effective amount of mitochondria or combined mitochondrial agents (or compositions comprising same) is the total amount of mitochondria or combined mitochondrial agents sufficient to bring about a desired therapeutic effect or ameliorate at least one symptom of a disease, disorder, injury, or dysfunction. An effective amount can be, e.g., at least or about $1\times10^2$ mitochondria or combined mitochondrial agents e.g., from about $1\times10^3$ to about $1\times10^{14}$, about $1\times10^4$ to about $1\times10^{13}$, about $1\times10^5$ to about $1\times10^{12}$, about $1\times10^6$ to about $1\times10^{11}$, about $1\times10^7$ to about $1\times10^{10}$, about $1\times10^3$ to about $1\times10^7$, about $1\times10^4$ to about $1\times10^6$, about $1\times10^7$ to about $1\times10^{14}$, or about $1\times10^8$ to about $1\times10^{13}$, about $1\times10^9$ to about $1\times10^{12}$, about $1\times10^5$ to about $1\times10^8$ or at least or about $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, or at least or about $1\times10^{14}$, or e.g., an amount more than $1\times10^{14}$. As used herein, the term "total amount" in the context of administration to a patient can refer to the total amount of mitochondria or combined mitochondrial agents in a single administration (e.g., one injection, one dose administered in an infusion) or in multiple administrations (e.g., multiple injections), depending on the dosing regimen being performed.

Isolated mitochondria and/or combined mitochondrial agents can be administered to a subject every 12-24 hours by various routes, e.g., direct injection, vascular delivery. In some embodiments, isolated mitochondria or combined mitochondrial agents can be administered to a subject every 5-10 minutes (e.g., every 5 minutes, every 10 minutes, every 15 minutes, every 30 minutes, every hour, etc.) by various routes, e.g., direct injection, vascular infusion.

In some embodiments, isolated mitochondria or combined mitochondrial agents can be directly injected into tissues or organs by Gauge 24, 25, 26, 27, 28, 29, 30, 31, 32, 33, and 34 needles. In some other cases, isolated mitochondria, or combined mitochondrial agents can be delivered to a target site by a catheter.

It is noted that in some cases, the effects of mitochondria depend on the length of the time period between the time of isolation and the time of use. Thus, in some embodiments, the mitochondria are freshly isolated and viable. The mitochondria or combined mitochondrial agents can be administered to a subject within about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes after the mitochondria are isolated. In some instances, the mitochondria or combined mitochondrial agents are administered to a subject within about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes after starting the mitochondria isolating process. Mitochondria and/or combined mitochondrial agents may in some instances be stored for a short period of time (e.g., about 10 minutes, about 20 minutes, about 30 minutes, about 40 minutes, about 50 minutes, about 60 minutes, about 90 minutes, about 120 minutes, etc.) before use.

In some embodiments, mitochondria and/or combined mitochondrial agents can be administered at least or about 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min, 180 min, 6 hours, 12 hours, 1 day, 2 days, or 3 days prior to ischemia-reperfusion injury in a single dose or in multiple doses, each comprising a therapeutically effective amount of mitochondria and/or combined mitochondrial agents. In some embodiments, a series of recurring doses may be administered about every 1 min, 2 min, 3 min, 4 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min prior to, during, or after ischemia-reperfusion injury.

In some embodiments, the administration can reduce the damage caused by ischemia-reperfusion injury by at least 10%, 20%, 30%, 40%, 50%, 60%, 70%, or 80%. In some embodiments, the administration can increase the organ function, the tissue function, or the cellular function after the ischemia-reperfusion injury by at least 10%, 20%, 30%, 40%, 50%, 60%, 70%, or 80%.

It is also noted that, in some cases, frozen-thawed mitochondria are not viable and not effective for certain treatments described herein, e.g., treatment of ischemia/reperfusion injuries. Thus, in some embodiments, the mitochondria are not frozen and thawed after isolation from tissues and/or cells. In some embodiments, the mitochondria or combined mitochondrial agents are placed on ice or at 4° C. prior to use.

The mitochondria for the treatment can be isolated from cells or tissues of an autogenous source, an allogeneic source, and a xenogeneic source. In some instances, mitochondria are collected from cultured cells or tissues of a subject, and these mitochondria are administered back to the same subject. In some other cases, mitochondria are collected from cultured cells or tissues of a second subject, and these mitochondria are administered to a first subject. In some cases, mitochondria are collected from cultured cells or tissues from the same species. In some cases, mitochondria are collected from cultured cells or tissues from a different species (e.g., mice, swine, yeast).

EXAMPLES

The invention is further described in the following examples, which do not limit the scope of the invention described in the claims.

Example 1: Methods and Materials

Animal Care and Bio Safety

This investigation was conducted in accordance with the National Institutes of Health's guidelines on animal care and use and was approved by the Boston Children's Hospital's Animal Care and Use Committee (Protocol 16-04-3169). All animals received humane care in compliance with the Guide for the Care and Use of Laboratory Animals (nap.edu/catalog/12910/guide-for-the-care-and-use-of-laboratory-animals-eighth website).

Representative Experimental Model

Figure 1B:
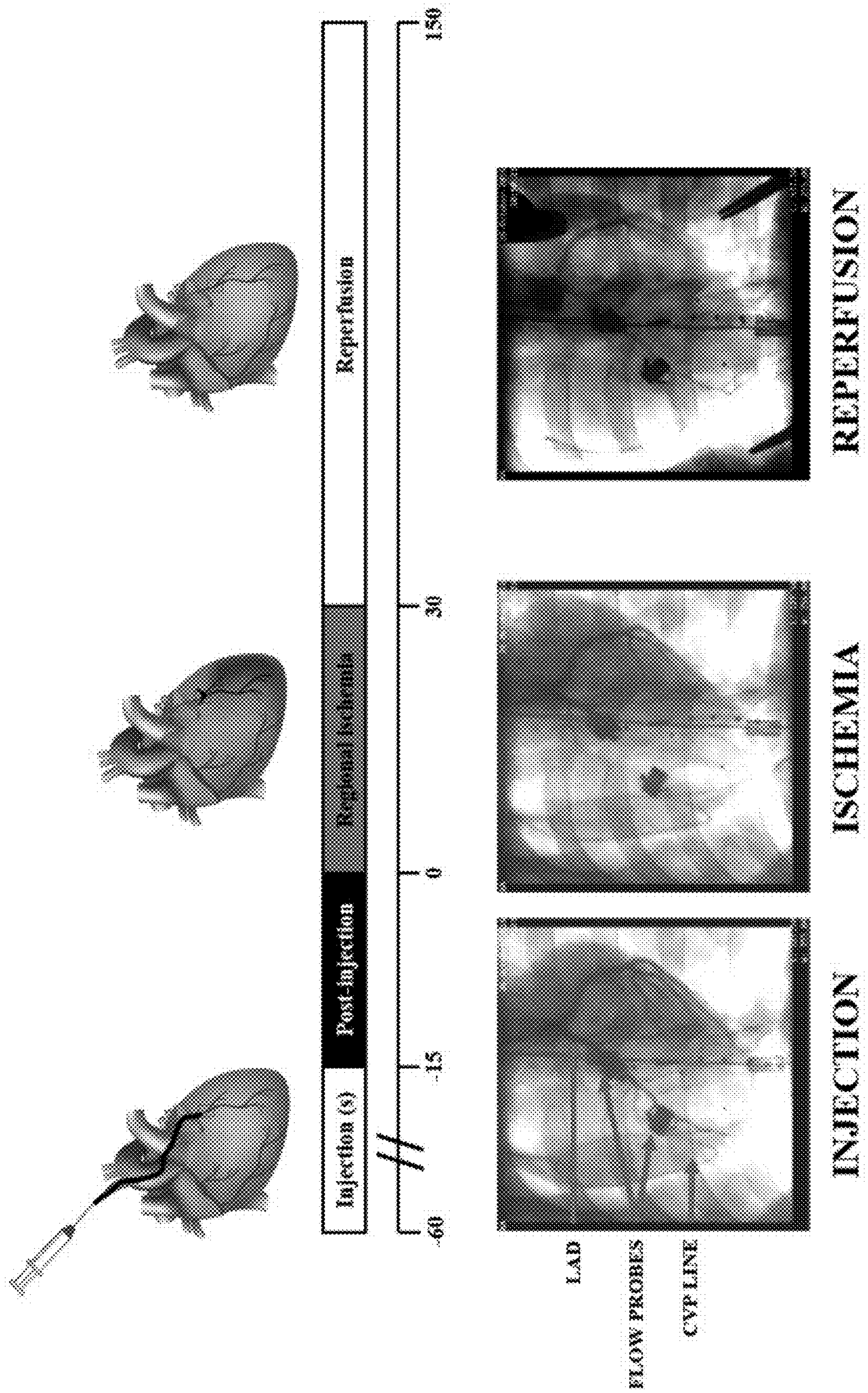
FIG. 1B shows a schematic of an experimental timeline wherein one or more injections were administered between 60 and 15 minutes prior to ischemia, and an organ was reperfused for 120 minutes following 30 minutes of ischemia. Representative images of angiography of injection, ischemia, and reperfusion are also shown in the figures.

FIGS. 1A-1B show a schematic diagram of one experimental model. A figure depicting a representative experimental model is shown in FIGS. 1A-1B. Female Yorkshire pigs, (26 pigs, 40-60 kg) were randomly selected for vehicle (VEH, n=10) or single ($MT_S$, n=10) or serial MT ($MT_{SS}$, n=6).

Animals were sedated with intramuscular Telazol (2.2-4.4 mg/kg,) and Xylazine (1-2 mg/kg). Endotracheal intubation was performed, and general anesthesia was induced with isoflurane (3% induction, 0.5%-2.0% maintenance). Ventilatory frequency and volumes were adjusted to maintain physiological arterial blood gas values. Normothermia was maintained using a water perfused heater pad. Femoral lines were placed in a sterile fashion for continuous mean arterial pressure (MAP) and central venous pressure (CVP) monitoring. Intravenous Heparin 100 unit/kg and 2% Lidocaine 2 mg/kg were injected at the start of the procedure.

Following verification of deep anesthesia, a stemotomy was performed. The pericardium was opened, the left anterior descending artery (LAD) was dissected and a flow probe attached. A suture was passed around the LAD, and both ends were passed through a small vinyl tourniquet to form a snare.

The right carotid artery was then cannulated with a 6F angiography sheath using a direct cut with exposure of the vessels. Selective catheterization of the left coronary artery was performed using a 5F multipurpose guide-catheter (Merit Medical Systems, South Jordan, UT) followed by injection of iodinated contrast medium (Optiray 350 Ioversol 74%, Guerbet, Villepinte, France) (FIGS. 1A-1B).

Mitochondrial Isolation

The pectoralis major was located and dissected, and a small piece was surgically extracted using a 6 mm biopsy punch (approximately 0.01 g) (Miltex, York, Pa) and used for mitochondrial isolation, as previously described (Preble J M, Pacak C A, Kondo H, MacKay A A, Cowan D B, McCully J D. Rapid Isolation and Purification of Mitochondria For Transplantation By Tissue Dissociation And Differential Filtration. J Vis Exp. 2014; (91):2-8). The isolated mitochondria were suspended in vehicle solution (250 mM sucrose; 10 mM K+-HEPES pH 7.2; 0.5 mM K+-EGTA, pH 8.0) (Emani S M, Piekarski B L, Harrild D, del Nido P J, McCully J D. Autologous mitochondrial transplantation for dysfunction after ischemia-reperfusion injury. J Thorac Cardiovasc Surg. 2017; 154(1):286-289).

Experimental Groups

Figure 2:
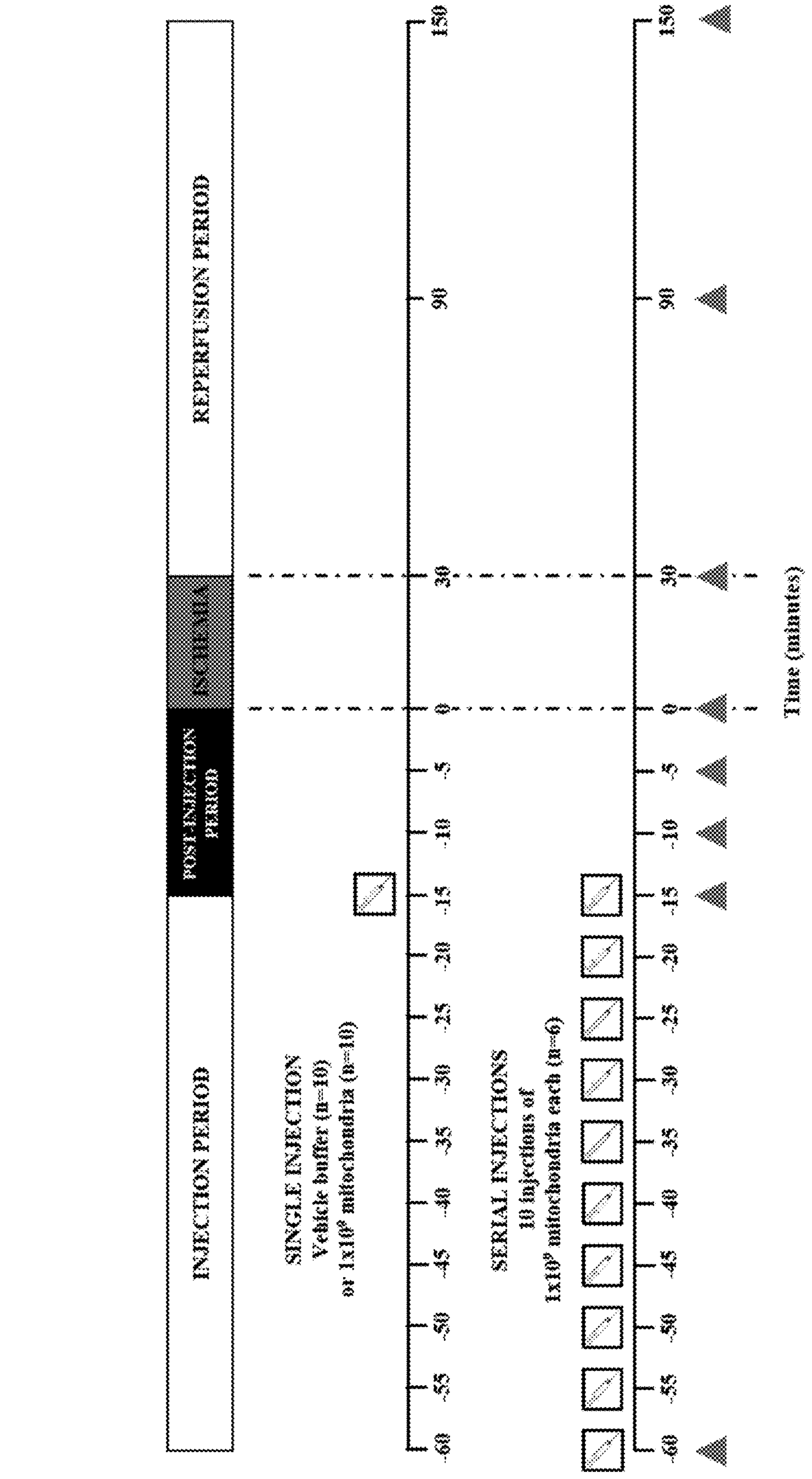
FIG. 2 is a diagram of experimental timelines, wherein groups received either a single injection 15 min prior to ischemia or a series of injections every five minutes from 60 to 15 minutes prior to ischemia. Groups that received a single injection comprising mitochondria are designated $MT_S$, and groups that received a series of injections comprising mitochondria are designated $MT_{SS}$. Measurement time points used in some of the regional and global measurements are indicated by the red arrowheads on the bottom.

Animals treated by intracoronary injection, were divided into three groups. Animals received either vehicle solution alone (VEH, 6 mL) or vehicle solution containing mitochondria. Single and serial MT injections were performed. Single injections were delivered as a bolus antegrade into the left main coronary artery ($1\times10^9$ in 6 mL, MTS, n=10). Serial injections of respiration buffer containing mitochondria (10 injections of $1\times10^9$ in 6 mL of respiration buffer, each injection, MTSS, n=6) were delivered every 5 min (FIG. 2).

The hearts were allowed to recover for fifteen minutes after the final injection. Temporary regional ischemia (RI) was induced by snaring the LAD. Following 30 minutes of RI, the snare was released, and the heart was reperfused for 120 minutes. Angiography was performed to confirm LAD patency (FIG. 1B).

Left Ventricular Global and Regional Function

Global left ventricular (LV) function was evaluated with a 7F pressure-volume conductance catheter (Transonic Systems Inc, Ithaca, NY) inserted through the apex. Data were continuously recorded using LabChart 7 Acquisition Software (AD Instruments, Sidney, Australia). LV peak developed pressure (Pdev, mmHg), LV end diastolic pressure (Ped, mmHg) and maximal change of LV pressure over time (dP/dt max, mmHg/s) were obtained. Echocardiography was performed using a Philips iE33™ machine with a 5-MHz transducer (Philips Healthcare, Amsterdam, Netherlands). Two-dimensional echocardiography, M-mode echocardiography with 2D guidance, and Doppler echocardiography were used to measure the size and volume of the LV cavity. Images and data were obtained as recommended by the American Society of Echocardiography Standards for assessment of LV function (Lang R M, Badano L P, Mor-Avi V, et al. Recommendations for cardiac chamber quantification by echocardiography in adults: An update from the American society of echocardiography and the European association of cardiovascular imaging. Eur Heart J Cardiovasc Imaging. 2015; 16(3):233-271). Regional myocardial function was assessed by sonomicrometry (Sonometrics Digital Ultrasonic Measurement System, Sonometrics Corp., London, ON, Canada), echocardiography, and endocardial global circumferential strain (GCS). Four digital piezoelectric ultrasonic probes (2.0 mm) were put in the sub-endocardium in the area of RI. Digital data were inspected using post-processing software (SonoView, Sonometrics Corp., London, ON, Canada). Regional echocardiographic measurements were obtained on epicardial short-axis images, aligning the cursor just below the mitral leaflets, in the area of RI. Strain analysis was performed offline with TomTec 2D Cardiac Performance Analysis (TomTec Imaging Systems, Munich, Germany). As GCS represents fiber shortening, this was expressed as a negative numeric value, with a more negative value representing greater shortening (Risum N, Ali S, Olsen N T, et al. Variability of global left ventricular deformation analysis using vendor dependent and independent two-dimensional speckle-tracking software in adults. J Am Soc Echocardiogr. 2012; 25(11):1195-1203).

Coronary Blood Flow

The LAD was dissected distal to the second diagonal branch and a perivascular flow probe (Transonic Systems Inc, Ithaca, NY) was placed circumferentially. Coronary blood flow (CBF) was continuously recorded through a T403 Multi-Channel Research Console (Transonic Systems Inc, Ithaca, NY) and analyzed using LabChart 7 Acquisition Software.

Euthanasia

Following 120 minutes of reperfusion the heart was removed and the animal euthanized by exsanguination in accordance with the "guiding principles in the Care and Use of Animals" of the American Physiological Society's protocol. After euthanasia, all hearts were harvested for histological analysis, imaging and wet/dry weight.

Area at Risk and Infarct Size

Ischemic area at risk (AAR) was delineated by LAD ligation, cross-clamping of the aorta and subsequent injection of blue monocrystalline pigment (diluted 1:5 in PBS) into the aortic root (Suzuki Y, Lyons J K, Yeung A C, Ikeno F. In vivo porcine model of reperfused myocardial infarction: In situ double staining to measure precise infarct area/area at risk. Catheter Cardiovasc Interv. 2008; 71(1): 100-107). The heart was then removed, and the LV partitioned along the long axis, from apex to base, into 1-cm thick transverse sections. Infarct size was determined with triphenyl tetrazolium chloride (TTC) as previously described (McCully J D, Cowan D B, Pacak C A, Toumpoulis I K, Dayalan H, Levitsky S. Injection of isolated mitochondria during early reperfusion for cardioprotection. Am J Physiol Circ Physiol. 2009; 296(1):H94-H105; Masuzawa A, Black K M, Pacak C A, et al. Transplantation of autologously derived mitochondria protects the heart from ischemia-reperfusion injury. AJP Hear Circ Physiol. 2013; 304(7):H966-H982). Infarct size was determined by a blinded observer. Wet/dry weight was determined as previously described (McCully J D, Cowan D B, Pacak C A, Toumpoulis I K, Dayalan H, Levitsky S. Injection of isolated mitochondria during early reperfusion for cardioprotection. Am J Physiol Circ Physiol. 2009; 296(1):H94-H105; Masuzawa A, Black K M, Pacak C A, et al. Transplantation of autologously derived mitochondria protects the heart from ischemia-reperfusion injury. AJP Hear Circ Physiol. 2013; 304(7):H966-H982).

Histology and transmission electron microscopy LV samples from the area at risk were collected for histology and transmission electron microscopy as previously described ((McCully J D, Cowan D B, Pacak C A, Toumpoulis I K, Dayalan H, Levitsky S. Injection of isolated mitochondria during early reperfusion for cardioprotection. Am J Physiol Circ Physiol. 2009; 296(1):H94-H105; Masuzawa A, Black K M, Pacak C A, et al. Transplantation of autologously derived mitochondria protects the heart from ischemia-reperfusion injury. AJP Hear Circ Physiol. 2013; 304(7):H966-H982; Cowan D B, Yao R, Akurathi V, et al. Intracoronary delivery of mitochondria to the ischemic heart for cardioprotection. PLoS One. 2016; 11(8):1-19). Hematoxylin-and-eosin (H&E) stained slides were evaluated for necrosis and inflammatory cells infiltration. All histological and electron microscopy was performed by a blinded observer.

Statistical Analysis

Continuous variables are expressed as mean±standard error. Normality of all continuous variables was tested using the Shapiro-Wilk test and graphically assessed by histograms and Q-Q plots. Longitudinal analysis for between-group comparisons was performed using two-way repeated-measures-analysis-of-variance (ANOVA) and by fitting mixed-effects linear regression models. When a significant F-test was obtained upon overall two-way repeated-measures ANOVA, a Bonferroni-adjusted post-hoc analysis was used to assess pairwise differences between groups. One-way ANOVA was utilized for between group comparisons in the case of histopathological indices. In order to reduce the probability of false positive results (Type I error) due to the multiple comparisons, the Benjamini & Hochberg's False Discovery Rate (FDR) was utilized in order to assess differences between multiple groups and to control family-wise error to $\alpha<0.05$. All tests were two-tailed and statistical significance was set at the $P<0.05$ level. All statistical analyses were performed using STATA version 15.1 (Stata Corp LLC, College Station, Texas) and GraphPad Prism® version 7.00 for Mac OS X (GraphPad Software, La Jolla California USA).

Additional Experimental Model and Methods

A total of 57 adult female Yorkshire swine (45.0±5.5 kg) were used. This study was conducted in 3 phases. In the first phase, the safety profile and biodistribution of mitochondria by intracoronary delivery was determined in the nonischemic swine. In the second phase, based on the first-phase finding of the increase in coronary blood flow (CBF) from intracoronary infusion of mitochondria, the mechanism of mitochondria-induced increase in CBF was investigated. Finally, in the third phase, the efficacy of intracoronary mitochondrial transplantation in providing cardioprotection after regional myocardial ischemia was evaluated.

SURGICAL PREPARATION AND MITOCHONDRIAL Q5 ISOLATION. Animals were sedated with Telazol (2.2-4.4 mg/kg)/xylazine (1-2 mg/kg) and intubated. General anesthesia was maintained with a 0.5% to 2% isoflurane-oxygen mixture. Ventilation was adjusted to maintain pH 7.35 to 7.45, $P_{CO2}$ 30 to 40 mm Hg, and $P_{O2}$ 85 to 100 mm Hg. Core temperatures were maintained at >36° C. Median sternotomy was performed, and the heart was suspended in a pericardial cradle. Then, angiographic access to the left coronary artery (LCA) was established by floating a 5-F JR angiography catheter (Merit Medical Systems, Inc., South Jordan, Utah) through the right carotid artery (5-F sheath) to the left coronary ostium under fluoroscopy. The coronary tree was visualized by injection of 5 ml of contrast solution (74% Ioversol Optiray-350, Mallinckrodt, Inc., St. Louis, Missouri) during 5 s, followed by a 5-ml saline flush. Two pieces of muscle were harvested from the pectoralis major muscle of each animal with a 6-mm biopsy punch and immediately used for mitochondrial isolation. Autologous mitochondria were isolated and mitochondrial ATP content was measured as previously described (McCully J D, Cowan D B, Pacak C A, Toumpoulis I K, Dayalan H, Levitsky S. Injection of isolated mitochondria during early reperfusion for cardioprotection. Am J Physiol Heart Circ Physiol 2009; 296:H94-105; Masuzawa A, Black K M, Pacak C A, et al. Transplantation of autologously derived mitochondria protects the heart from ischemia-reperfusion injury. Am J Physiol Heart Circ Physiol 2013; 304:H966-82; Preble J M, Pacak C A, Kondo H, MacKay A A, Cowan D B, McCully J D. Rapid isolation and purification of mitochondria for transplantation by tissue dissociation and differential filtration. J Vis Exp 2014; 91:e51682).

PHASE I: SAFETY OF INTRACORONARY DELIVERY OF MITOCHONDRIA AND BIODISTRIBUTION IN THE NONISCHEMIC HEART. A total of 20 animals were used in phase 1. There were no animal losses in phase 1 studies. Myocardial uptake and biodistribution of mitochondria by intracoronary delivery were evaluated in 3 animals. Next, 6 animals were used to evaluate the concentration tolerance of intracoronary injection of mitochondria by angiographic injection of 5 mitochondrial concentrations into the LCA. Intracoronary injection of 1 optimum mitochondrial concentration was then tested under normal conditions and in the presence of myocardial stressors, including coronary vasoconstriction, tachycardia, and increased afterload (n=6). The safety of repeated injections of mitochondria was evaluated (n=5). Coronary patency, CBF, hemodynamics, and regional and global left ventricular (LV) functions were evaluated.

Mitochondrial biodistribution and cellular uptake. To evaluate myocardial uptake and biodistribution of mitochondria, autologous mitochondria were labeled with $^{18}$F-rhodamine-6G (Cowan D B, Yao R, Akurathi V, et al. Intracoronary delivery of mitochondria to the ischemic heart for cardioprotection. PLoS One 2016; 11: e0160889; Bartholomä M D, Zhang S, Akurathi V, et al. (18) F-labeled rhodamines as potential myocardial perfusion agents: comparison of pharmacokinetic properties of several rhodamines. Nucl Med Biol 2015; 42:796-803). To increase detection sensitivity, mitochondria were delivered at a concentration 6-fold greater ($6\times10^9$) than the therapeutic dosage used in previous studies ($1\times10^9$). Mitochondria were injected serially in six 5-second boluses, each bolus containing $1\times10^9$ mitochondria in 5 ml of vehicle (300 mM sucrose, 10 mM $K^+$ 4-(2-hydroxyethyl)-1-piperazineethanesulfonic acid pH 7.2, and 1 mM $K^+$ ethylene glycol-bis(b-aminoethyl ether)-N,N,N'N'-tetraacetic acid, pH 8.0). After 10 min of circulation, a timeframe long enough for the blood to circulate through the entire body approximately 10 times (Hannon J P, Bossone C A, Wade C E. Normal physiological values for conscious pigs used in biomedical research. Lab Anim Sci 1990; 40:293-8), the animal was euthanized and imaged by whole-body positron emission tomography (Siemens, Munich, Germany) (n=2). In a separate animal, cellular uptake of mitochondria was evaluated by intracoronary injection of xenogeneic mitochondria isolated from human cardiac fibroblasts and labeled with iron (II, III) oxide nanoparticles. The use of human mitochondria allows differentiation of the transplanted mitochondria from the native swine cardiac mitochondria by immunohistochemistry. Transplanted mitochondria were detected by Prussian blue staining for iron-labeled mitochondria and immunohistochemistry as previously described (n=1).

Safety of intracoronary injection of mitochondria. Five concentrations of mitochondria ($1\times10^3$, $1\times10^5$, $1\times10^7$, $1\times10^9$, and $1\times10^{11}$) were each suspended in 5 ml of vehicle. Each concentration was injected into the LCA as a 5-s bolus followed by a 5-ml saline flush in the order of increasing concentration (n=6).

To evaluate the safety of intracoronary injection of mitochondria in the presence of increased myocardial demand, coronary vasoconstriction or tachycardia with increased afterload was individually induced in 6 animals. Coronary vasoconstriction was induced by intracoronary injection of antidiuretic hormone (ADH) (1.75 nmol in 5 ml of saline). Tachycardia with increased afterload was induced with epinephrine (0.5 mmol in 5 ml of saline). On confirmation of the intended effects, $1\times10^9$ mitochondria were provided as boluses into the LCA (n=6). Then, in 5 animals, the safety of repeated injection of mitochondria was assessed by 10 serial intracoronary injections of $1\times10^9$ mitochondria in 5 ml of vehicle into the LCA in 5-s boluses every 5 min.

Assessment of coronary patency, coronary blood flow, and cardiac function. Coronary patency was evaluated by angiography immediately after and 5 min after intracoronary mitochondrial injections. Angiographic analysis was performed by the Cardiology Department of Boston Children's Hospital. CBF was continuously measured by placing an ultrasonic flow probe (3R1334, Transonic Systems Inc, Ithaca, New York) circumferentially around a 5-mm to 7-mm segment of the left anterior descending artery distal to the first diagonal branch and recorded via a Transonic T206 blood-flowmeter. Global LV function was evaluated by a 7F-VSL transonic pressure-volume conductance catheter inserted into the LV cavity through the LV apex. Measurements were analyzed with LabChart 7 acquisition software (AD Instruments, Sydney, Australia). Regional myocardial function was evaluated by sonomicrometry of the LV free wall and analyzed with SonoView post-processing software (Sonometrics Corp., London, United Kingdom).

PHASE 2: EVALUATION OF MITOCHONDRIA-INDUCED INCREASE IN CORONARY BLOOD FLOW. A total of 21 animals were used in phase 2. There were no animal losses in phase 2 studies. We first evaluated whether the increase in CBF resulting from intracoronary injection of mitochondria was the result of increased myocardial oxygen consumption by the introduction of large amounts of mitochondria into the vasculature. This was done by 2 methods: first, by measuring the CBF in response to direct myocardial injection of mitochondria at 10 locations ($1\times10^8$ each in 0.1 mL of vehicle) in close proximity to the left anterior descending artery, using a tuberculin syringe (n=3); and second, by the measurement of coronary sinus proportion venous oxygen saturation at baseline, immediately after (at peak of increase in CBF) and 10 min after intracoronary injection of mitochondria (n=4).

Intracoronary injection of devitalized mitochondria, HeLa and HeLa $p^0$ cell mitochondria. To investigate the role of mitochondrial viability and respiration competence in mitochondria-induced increase in CBF, mitochondria were devitalized (Masuzawa A, Black K M, Pacak C A, et al. Transplantation of autologously derived mitochondria protects the heart from ischemia-reperfusion injury. Am J Physiol Heart Circ Physiol 2013; 304: H966-82) and injected into the LCA (n=4). Next, mitochondria ($1\times10^9$) isolated from HeLa- and HeLa-$p^0$ cells, which differ in their ability to perform oxidative phosphorylation (Pacak A C, Preble J M, Kondo H, et al. Actin-dependent mitochondrial internalization in cardiomyocytes: evidence for rescue of mitochondrial function. Biol Open 2015; 4:622-6), were injected separately into the left anterior descending artery (n=6). CBF was compared. HeLa cells (CRMCCL-2, American Type Culture Collection, Manassas, Virginia) and HeLa-$p^0$ cells were cultured as previously described (Masuzawa A, Black K M, Pacak C A, et al. Transplantation of autologously derived mitochondria protects the heart from ischemia-reperfusion injury. Am J Physiol Heart Circ Physiol 2013; 304: H966-82; Pacak A C, Preble J M, Kondo H, et al. Actin-dependent mitochondrial internalization in cardiomyocytes: evidence for rescue of mitochondrial function. Biol Open 2015; 4:622-6).

Inhibition of coronary vasodilatory pathways. To determine the biochemical pathway(s) involved in mitochondria-induced increase in CBF, potential key mediators of coronary vasodilation were investigated in vivo, including endothelium-mediated nitric oxide synthase, cyclooxygenase- and vascular SM mediated adenosine receptors, ATP-sensitive potassium ($K_{ATP}$) channels, and inwardly rectifying potassium ($K_{IR}$) channels. CBF in response to intracoronary injection of $1\times10^9$ mitochondria was compared in the presence and absence of each pathway inhibition. Activators of each pathway were used as positive controls. Animals were pre-treated separately by slow intracoronary infusion of increasing concentrations of the pedigreed blocker of each vasodilatory pathway (n=4): nitromonomethyl L-arginine (0-100 mM; nitric oxide synthase blocker), indomethacin (0-100 mM; cyclooxygenase blocker), 8-p-sulfophenyl theophylline (0-1 mM; adenosinereceptor blocker), glibenclamide (0-2 mM; $K_{ATP}$ channel blocker), and barium chloride (0 to 100 mM; KR channel blocker). Nitromonomethyl L-arginine, 8-p-sulfophenyl theophylline, and barium chloride were dissolved separately in 60 ml of saline. Stock solutions of glibenclamide and indomethacin were made in 1 ml of dimethyl sulfoxide and slowly dissolved in 60 ml of warmed saline. A blocker was infused into the LCA during 20 min. Five min after completion of blocker treatment, pathway inhibition was confirmed by intracoronary injection of a known activator of the tested pathway. Bradykinin (0.01 nmol) was used as cyclooxygenase and nitromonomethyl L-arginine pathway activator, nicorandil (50 mmol) was used as $K_{ATP}$-channel activator, and ATP (30 mM) was used as KR-channel pathway activator. After confirmation of inhibition of the pathway in question, $1\times10^9$ mitochondria were injected into the LCA and CBF was measured. All blockers and activators were purchased from Sigma-Aldrich (St. Louis, Missouri).

PHASE 3: EFFICACY OF INTRACORONARY DELIVERY OF MITOCHONDRIA IN REGIONAL ISCHEMIA-REPERFUSION INJURY. A total of 16 animals were used in phase 3. There was 1 animal loss in the vehicle group. Animals were subjected to 30 min of regional myocardial ischemia by temporary snaring of the mid left anterior descending artery just distal to the second diagonal branch. The snare was released, and immediately on reperfusion, animals received either an intracoronary bolus of $1\times10^9$ mitochondria in 5 ml of vehicle (n=8) or 5 ml of vehicle alone (n=8). Hemodynamics, regional and global LV function, and CBF were continuously acquired. After 120 min of reperfusion, animals were euthanized, and the hearts were analyzed for area at risk and infarct size.

ECHOCARDIOGRAPHY. Echocardiography was acquired with a Philips iE33|M machine (Philips Medical Systems, Andover, Massachusetts) with an X7-2 (7-2 MHz) transducer at pre-ischemia, at 30 min of ischemia, and after 1 and 2 h of reperfusion. Short-axis view and M-mode tracings at the midpapillary level were analyzed with a RadiAnt DICOM™ Viewer (Medixant, Poznan, Poland) according to the American Society of Echocardiography standards (Lang R M, Badano L P, Mor-Avi V, et al. Recommendations for cardiac chamber quantification by echocardiography in adults: an update from the American Society of Echocardiography and the European Association of Cardiovascular Imaging. J Am Soc Echocardiogr 2015; 28:1-39).

EUTHANASIA. Animals were euthanized by intravenous injection of Fatal-Plus (50 mg/kg).

AREA AT RISK AND INFARCT SIZE. Area at risk and infarct size were determined with tetrazolium chloride staining and planimetry analysis (Rousou A J, Ericsson M, Federman M, Levitsky S, McCully J D. Opening of mitochondrial KATP channels enhances cardioprotection through the modulation of mitochondrial matrix volume, calcium accumulation, and respiration. Am J Physiol Heart Circ Physiol 2004; 287:H1967-76; McCully J D, Cowan D B, Pacak C A, Toumpoulis I K, Dayalan H, Levitsky S. Injection of isolated mitochondria during early reperfusion for cardioprotection. Am J Physiol Heart Circ Physiol 2009; 296:H94-105; Masuzawa A, Black K M, Pacak C A, et al. Transplantation of autologously derived mitochondria protects the heart from ischemia-reperfusion injury. Am J Physiol Heart Circ Physiol 2013; 304: H966-82).

STATISTICAL ANALYSIS. Statistical analyses were performed with Stata software (version 11.0; StataCorp, College Station, Texas). All data are expressed as mean_standard error of the mean. Blinding was not adopted for data collection and analysis of different injectates. Continuous data (CBF, hemodynamics, and regional and global LV contractility) were compared between groups with 2-way repeated-measures analysis of variance. When the overall difference across groups was significantly different, a Bonferroni-adjusted post hoc analysis was used for pairwise comparisons of interest. For CBF, comparisons were made between each point and baseline CBF at time zero within each group. Area under the curve (AUC) was compared between groups with a 1-way analysis of variance, and results are presented as mean±standard error of the mean with 95% confidence interval. A 1-way analysis of variance was also used for echocardiographic analyses, area at risk, and infarct size. Statistical significance was claimed at a 2-sided $p<0.05$.

Example 2: Myocardial Global Function and Regional Function Enhanced Following Single and Serial Injection Mitochondrial Transplantation FIGS. 3A-3D show global function measurements following intracoronary injection. FIGS. 4A-4D show global function measurements during injection (INJ), post-injection/pre-ischemia (black box), ischemia, and reperfusion. PV loop analysis, sonomicrometry and echocardiographic assessment of heart function (both global and regional) did not reveal many differences between Vehicle and $MT_S$ or $MT_{SS}$ groups at the time of injection, 0 time point ($P>0.05$ for each) (FIGS. 3A-4D, Table 1). Coronary blood flow (CBF) and myocardial function were increased temporarily during the pre-RI period in $MT_S$ and $MT_{SS}$ groups compared to VEH (FIGS. 3A-3D).

Figure 3A:
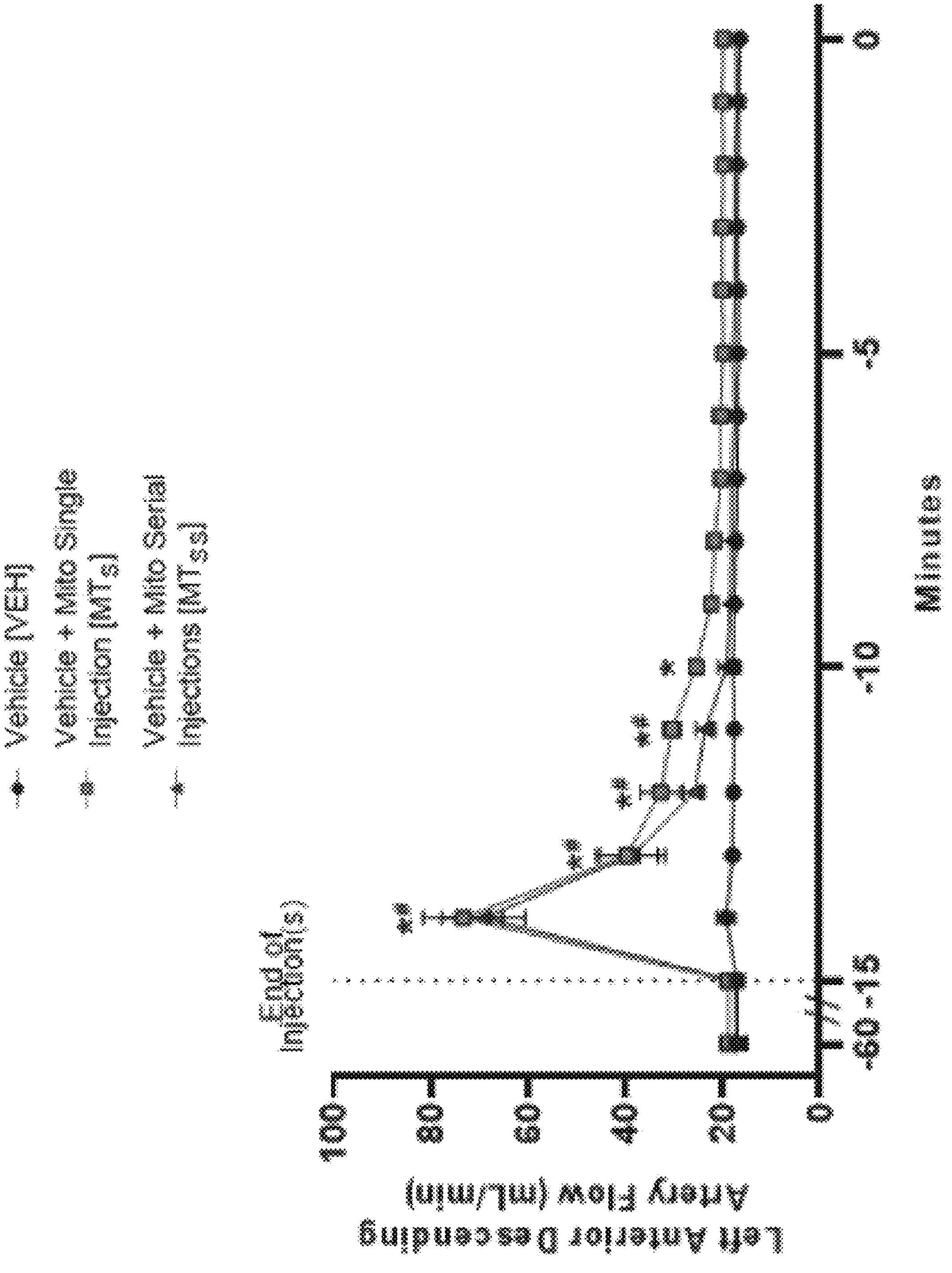
FIG. 3A is a line graph illustrating left anterior descending artery flow following intracoronary injection.
Figure 8:
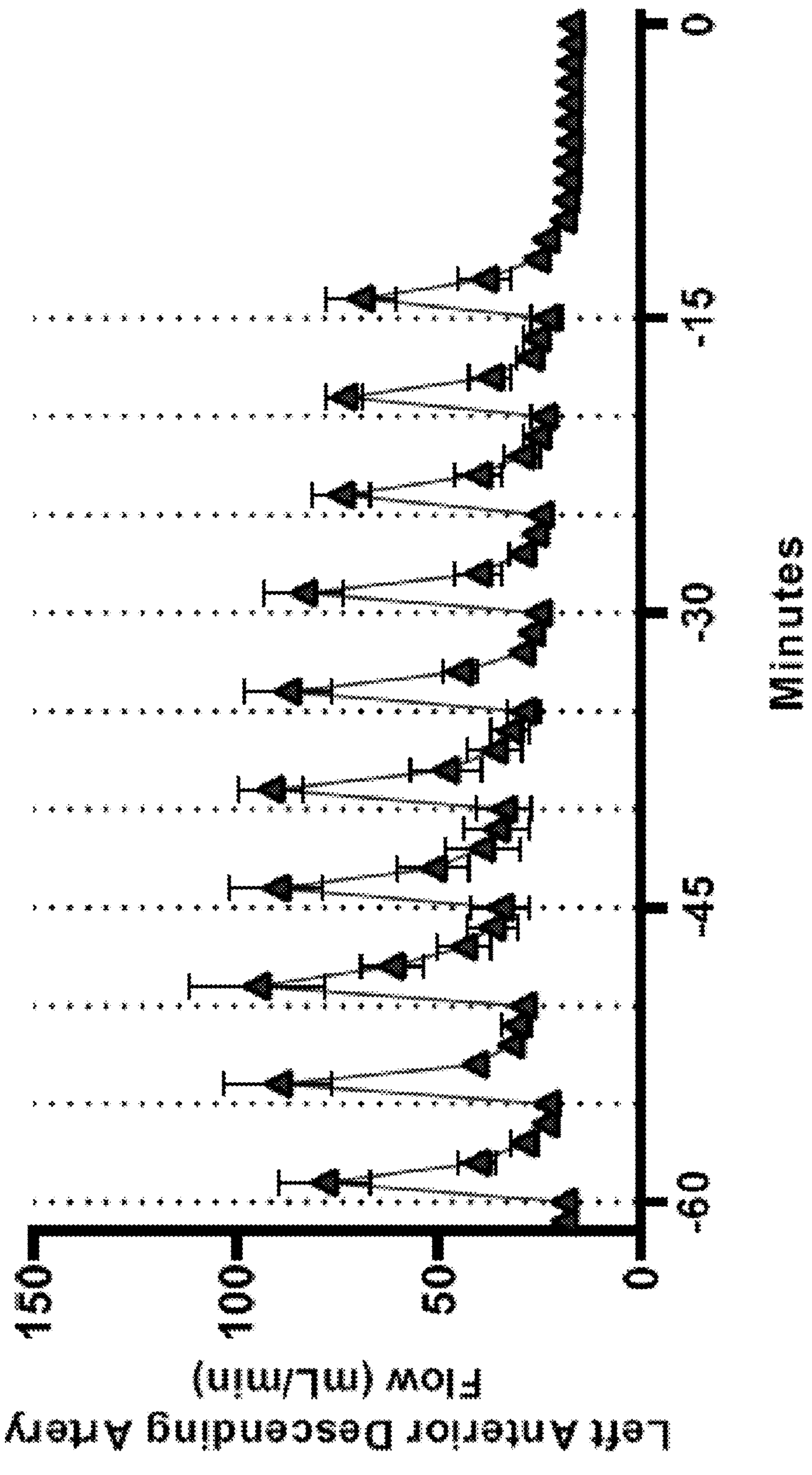
FIG. 8 is a line graph illustrating left anterior descending flow during 10 Serial Injections of $1\times10^9$ Mitochondria/each over 60 minutes in $MT_{SS}$ group. The dotted lines correspond to a single injection of mitochondria.

Both $MT_S$s and $MT_{SS}$ induced a transient increase in CBF significantly different from VEH for up to 5 minutes (FIG. 3A). This increase in CBF was consistent and reproducible for all injections in the $MT_{SS}$ group (FIG. 8). $MT_S$s and $MT_{SS}$ had no statistical effect on heart rate (HR) or mean arterial pressure (MAP) (FIG. 8).

Figure 3B:
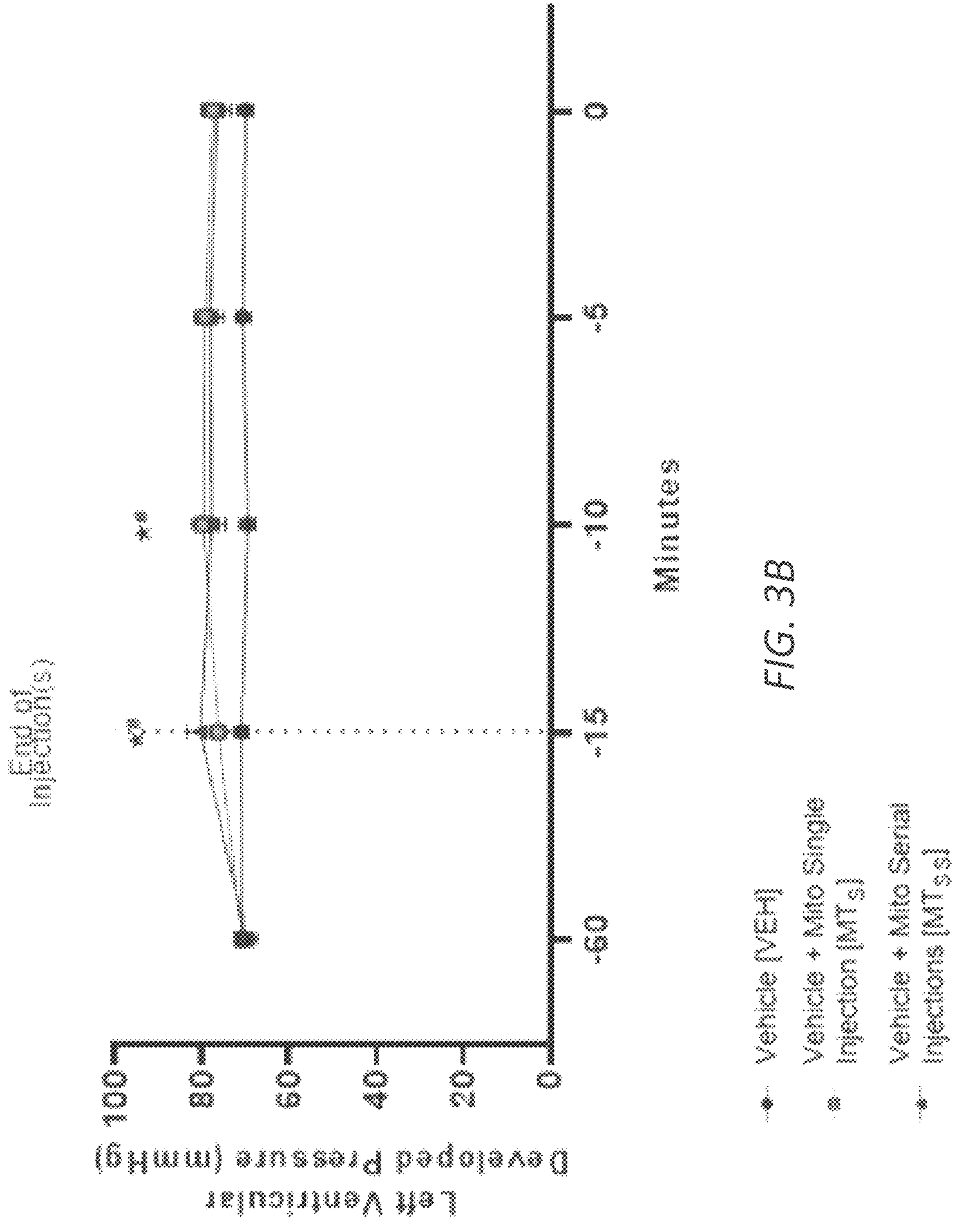
FIG. 3B is a line graph illustrating left ventricular developed blood pressure following intracoronary injection.
Figure 3C:
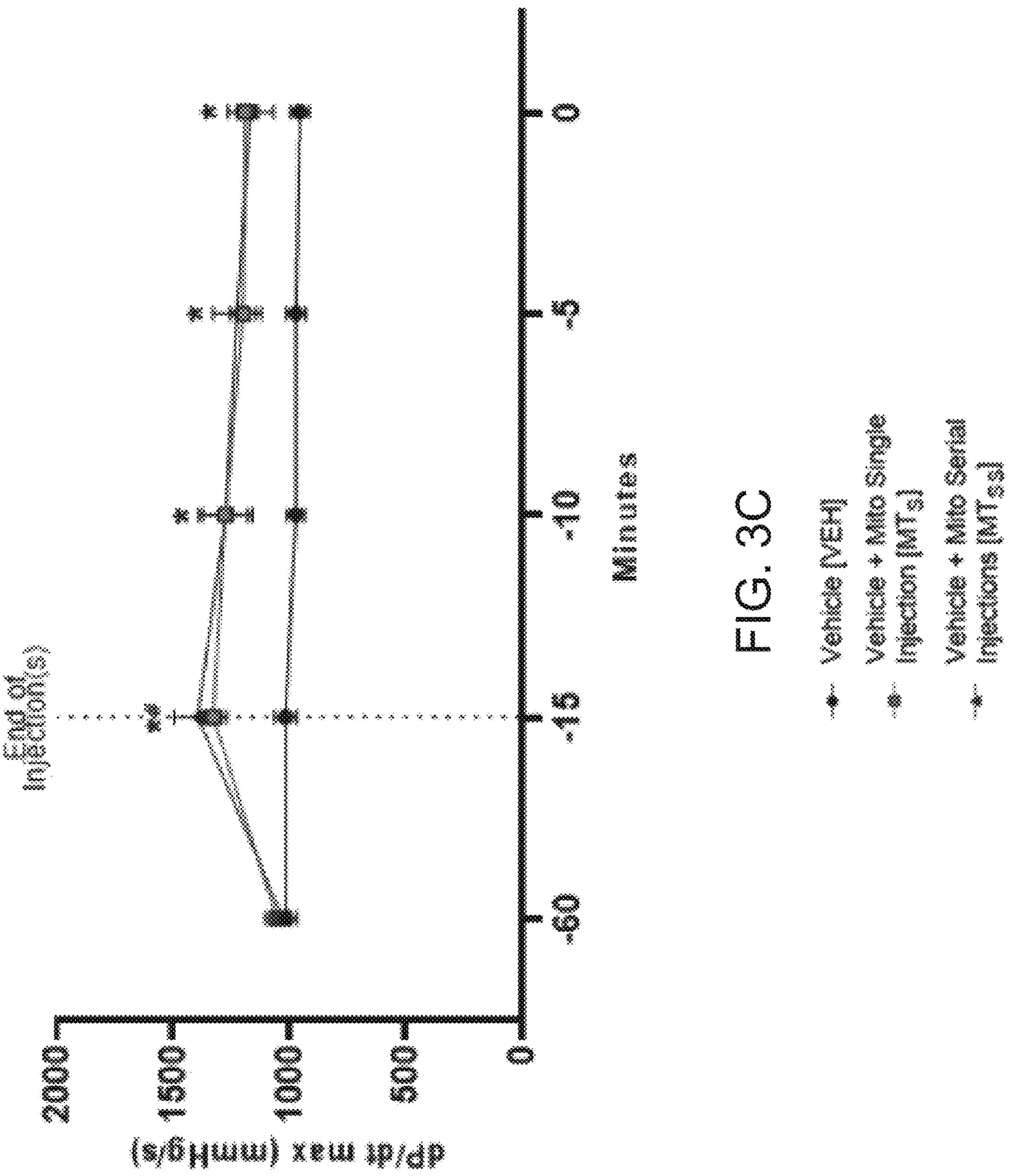
FIG. 3C is a line graph illustrating maximal rate of rise of left ventricular pressure (dP/dt max) following intracoronary injection.
Figure 4A:
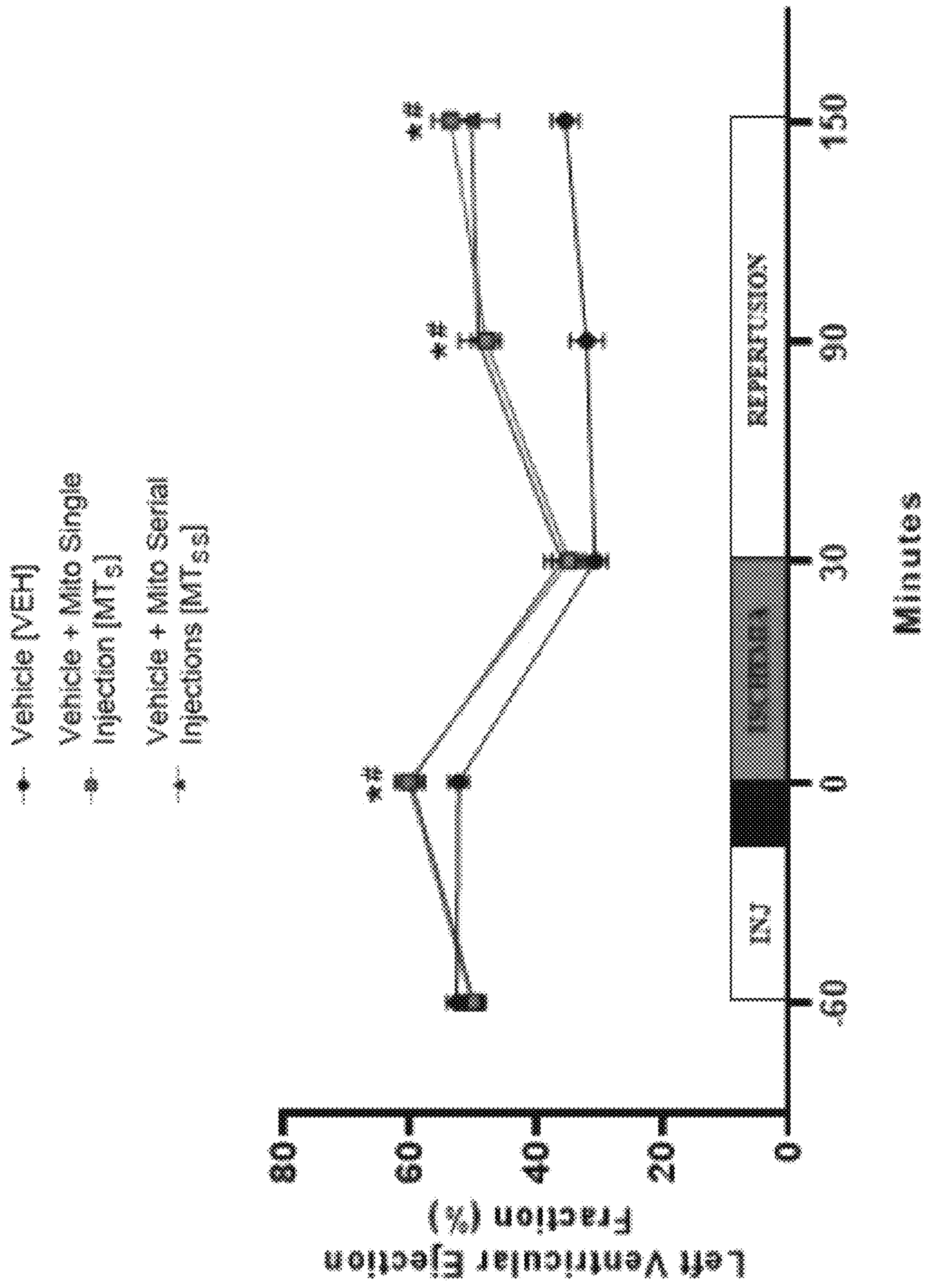
FIG. 4A is a line graph illustrating left ventricular ejection fraction during injection (INJ), post-injection/pre-ischemia (black box), ischemia, and reperfusion.
Figure 4B:
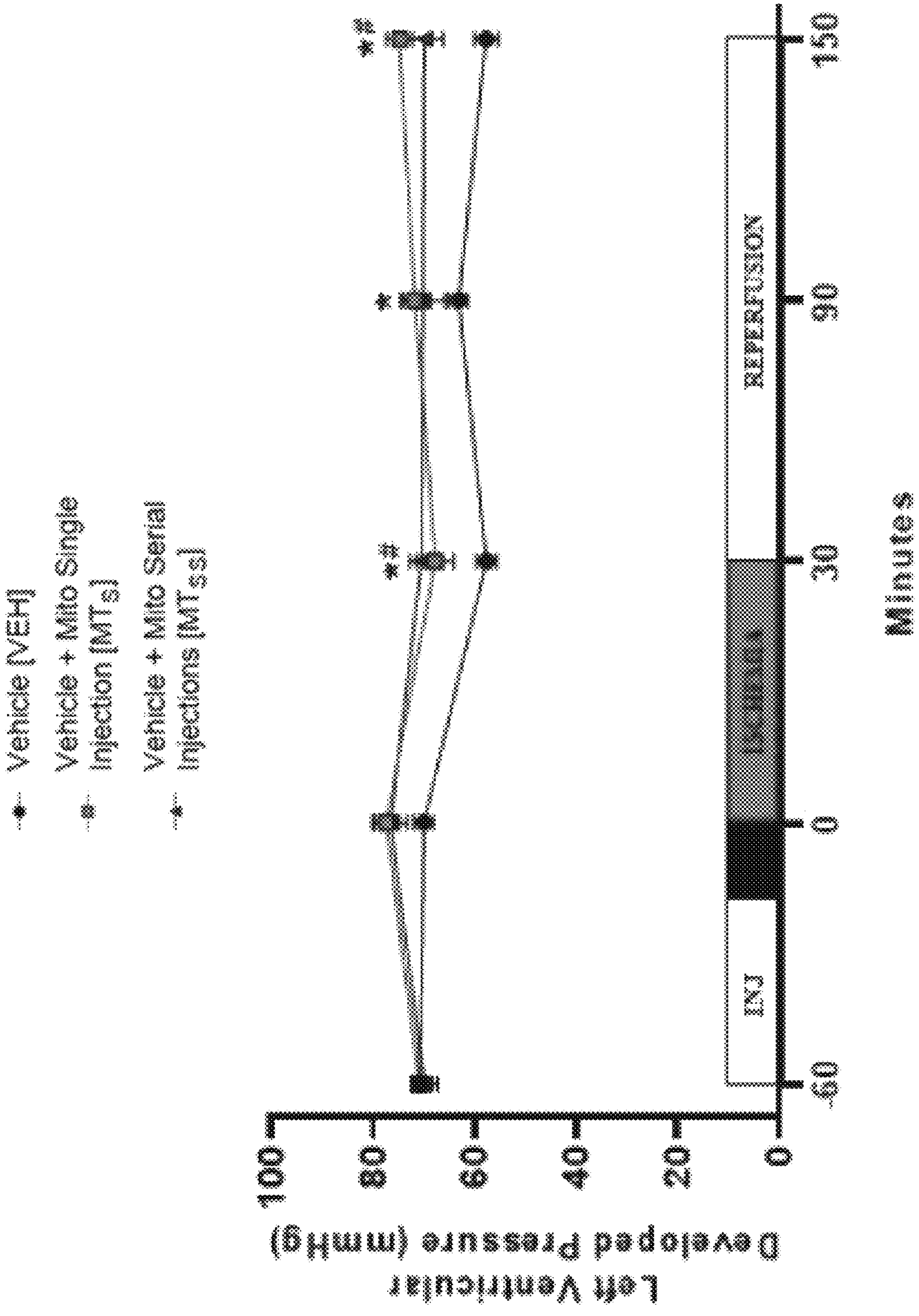
FIG. 4B is a line graph illustrating left ventricular developed blood pressure during injection (INJ), post-injection/pre-ischemia (black box), ischemia, and reperfusion.

Intracoronary delivery of mitochondria significantly increased LV function temporarily. LV Pdev increased for 5 minutes after the injection, whereas LV ejection fraction and dP/dt max were still enhanced at the end of the 15 minutes preceding ischemia (FIGS. 3B-3C). Following 30 minutes of RI, $MT_S$s and $MT_{SS}$ hearts had significantly increased CBF that persisted throughout reperfusion (VEH vs MTS and MTSS, P=0.04) (FIGS. 4A-4D). $MT_S$s and $MT_{SS}$ showed significantly enhanced ejection fraction (VEH vs $MT_S$ $P<0.001$; VEH vs $MT_{SS}$ P=0.04) (FIG. 4A) and developed pressure (VEH vs $MT_S$ $P<0.001$; VEH vs $MT_{SS}$ P=0.03) (FIG. 4B).

Figure 5A:
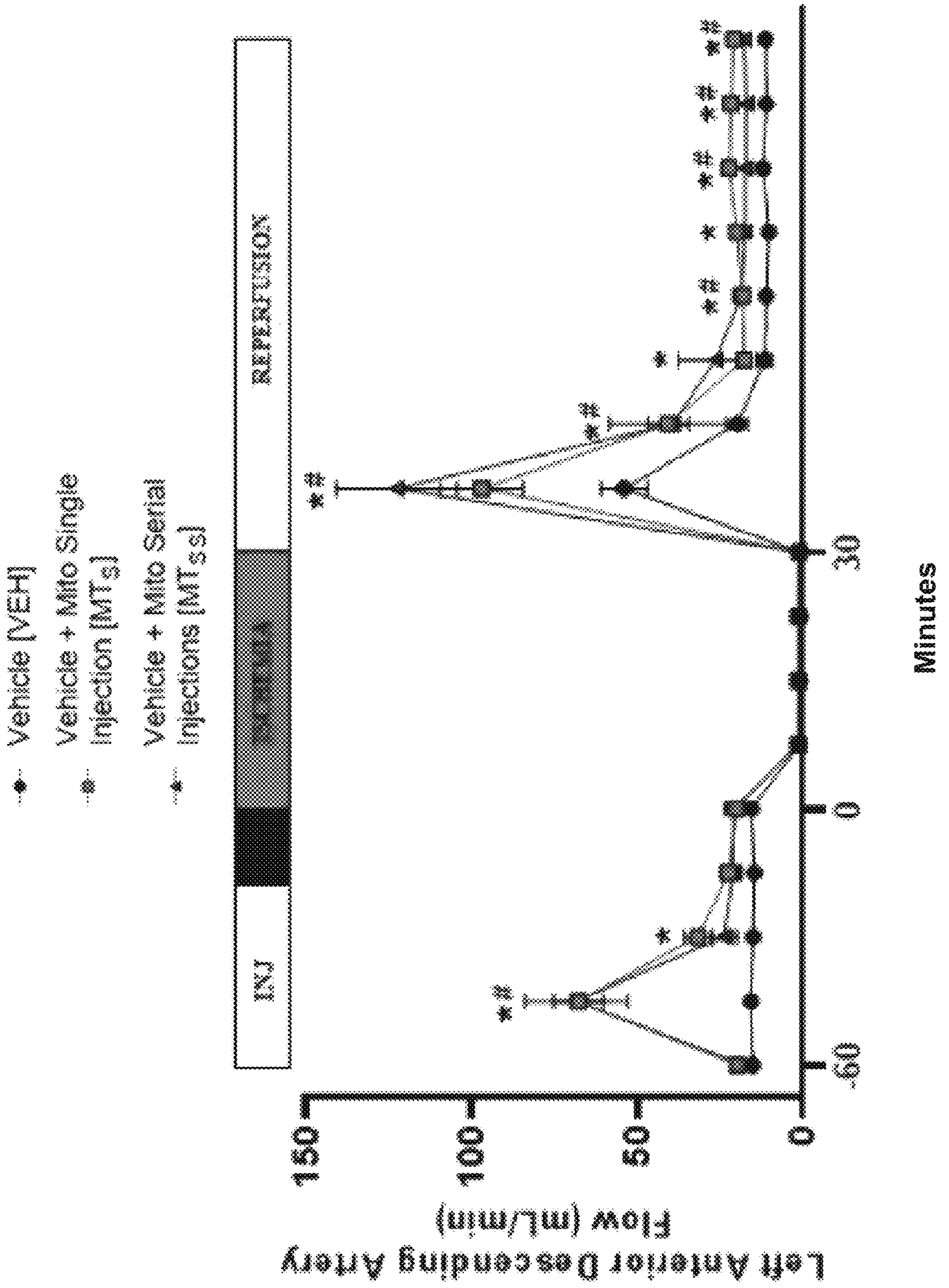
FIG. 5A is a line graph illustrating left anterior descending artery flow during injection (INJ), post-injection/pre-ischemia (black box), ischemia, and reperfusion.
Figure 5B:
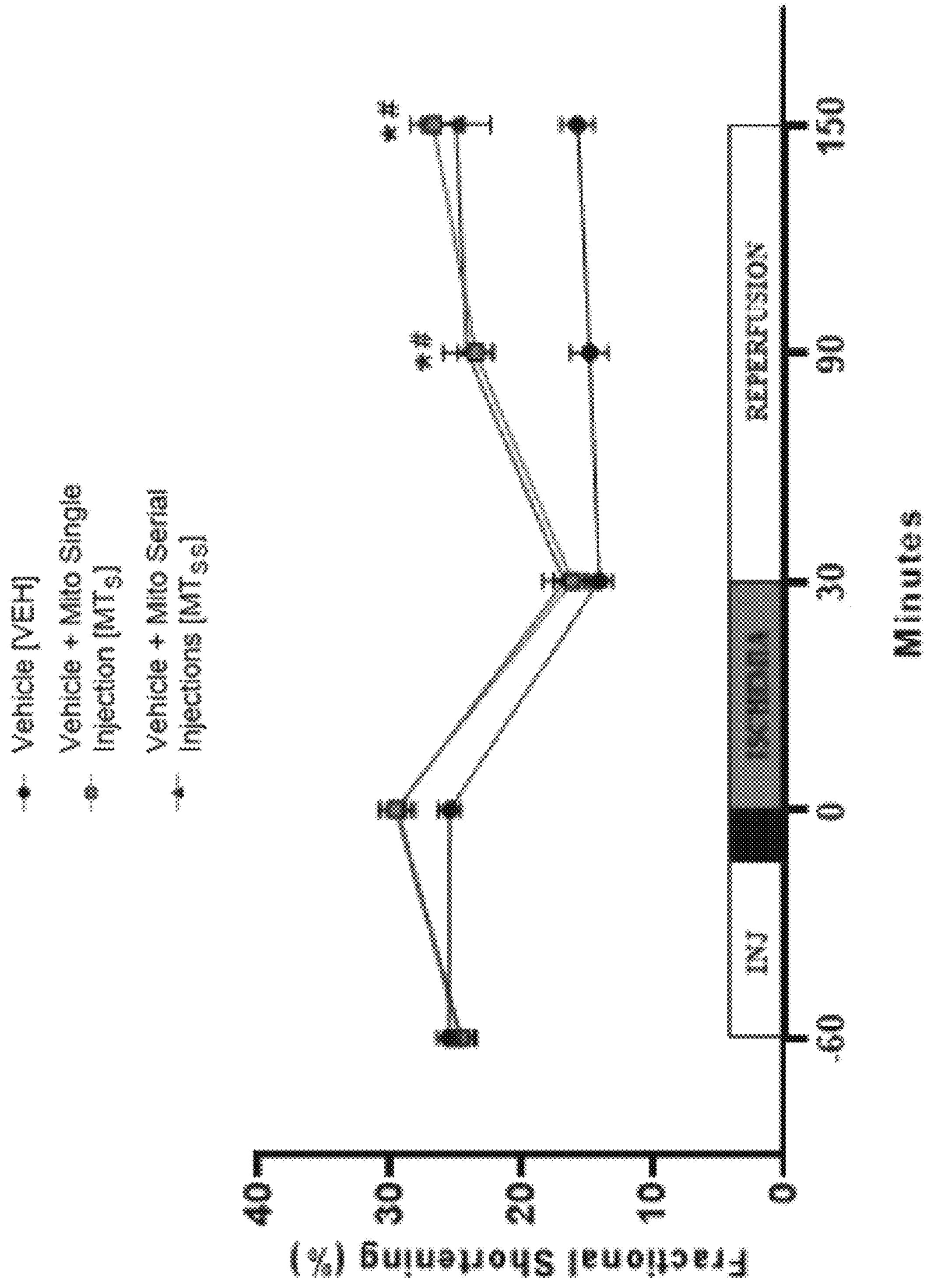
FIG. 5B is a line graph illustrating echocardiographic fractional shortening during injection (INJ), post-injection/pre-ischemia (black box), ischemia, and reperfusion.
Figure 5C:
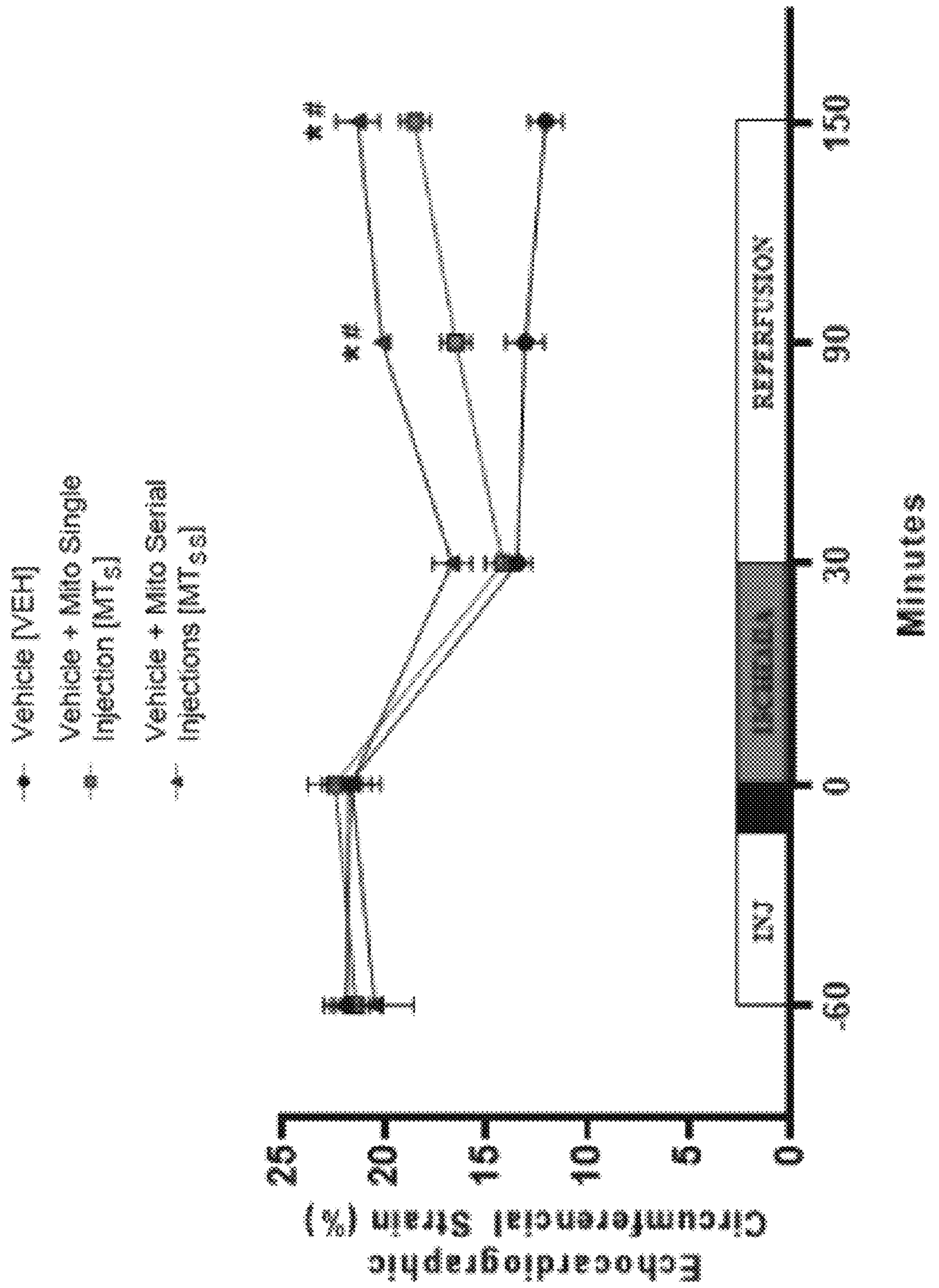
FIG. 5C is a line graph illustrating echocardiographic left ventricular endocardial global circumferential strain during injection (INJ), post-injection/pre-ischemia (black box), ischemia, and reperfusion.
Figure 5D:
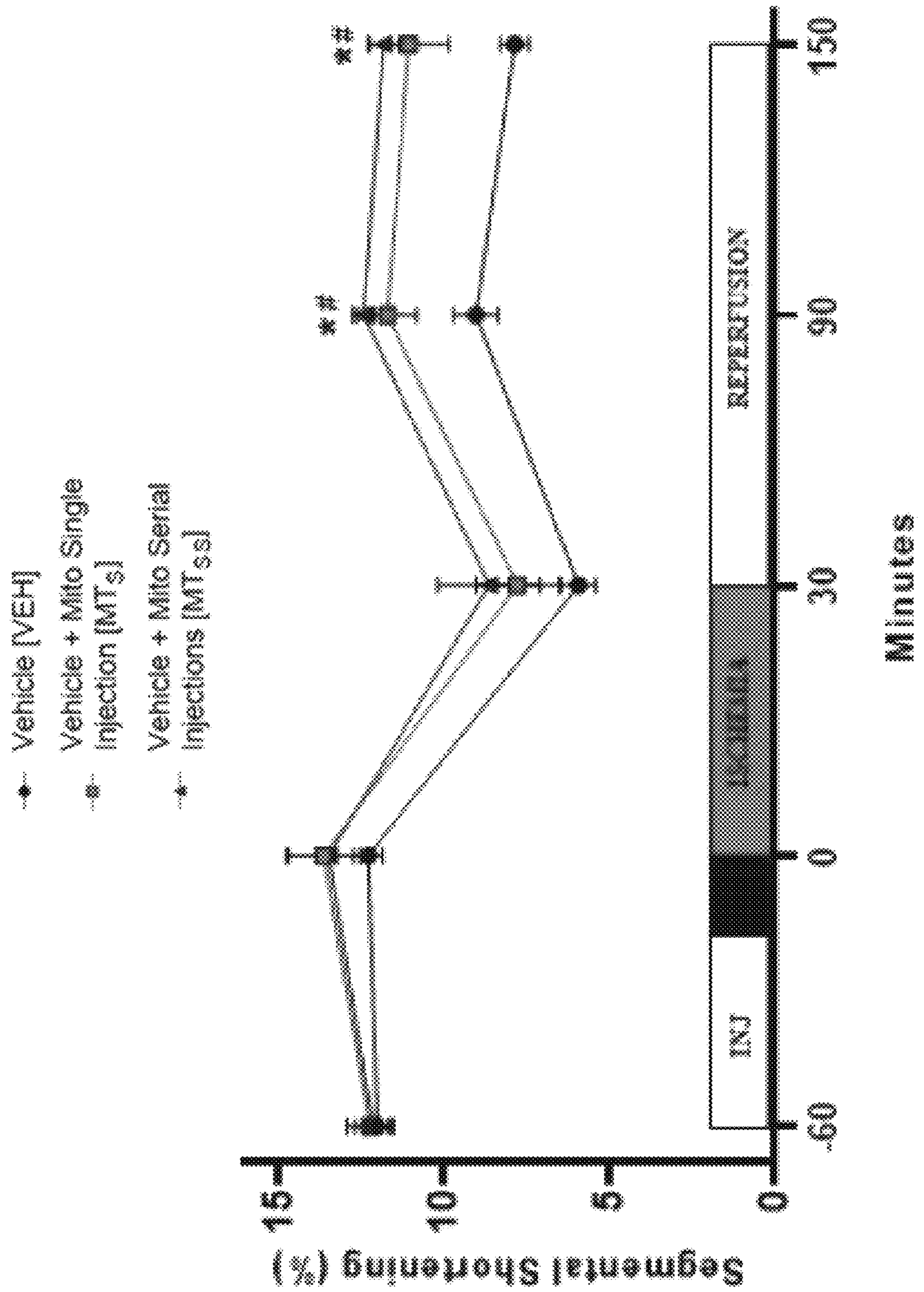
FIG. 5D is a line graph illustrating left ventricular systolic segmental shortening during injection (INJ), post-injection/pre-ischemia (black box), ischemia, and reperfusion. All results are shown as mean±SEM for each group. *P<0.05 Single Injection vs. Vehicle; #P<0.05 Serial Injections vs. Vehicle.

FIGS. 5A-5D show regional function measurements during injection (INJ), post-injection/pre-ischemia (black box), ischemia, and reperfusion. Regional function, assessed through segmental shortening (VEH vs $MT_S$ P=0.03; VEH vs $MT_{SS}$ $P<0.001$), fractional shortening (VEH vs $MT_S$ $P<0.001$; VEH vs $MT_{SS}$ P=0.04) and strain analysis (VEH vs $MT_S$ P=0.002; vs $MT_{SS}$ P=0.003), was also significantly improved by mitochondrial transplantation (FIGS. 5D, 5B, and 5C, respectively). At the end of the period prior to RI, for example at time point 0, no significant difference was observed for regional function between the groups (FIGS. 5A-5D).

Figure 6A:
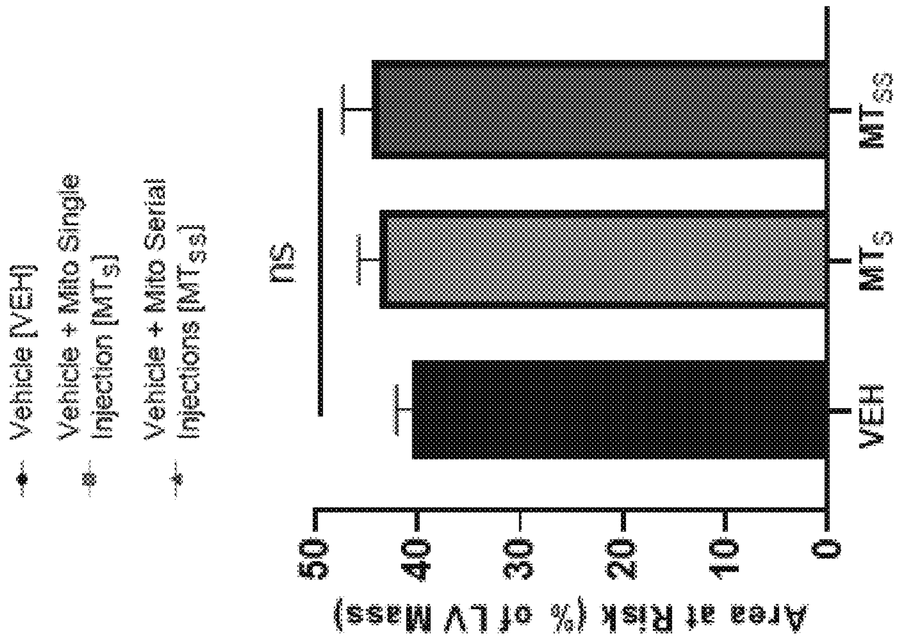
FIG. 6A is a bar graph illustrating area-at-risk (AAR) as % of left ventricular mass.
Figure 6B:
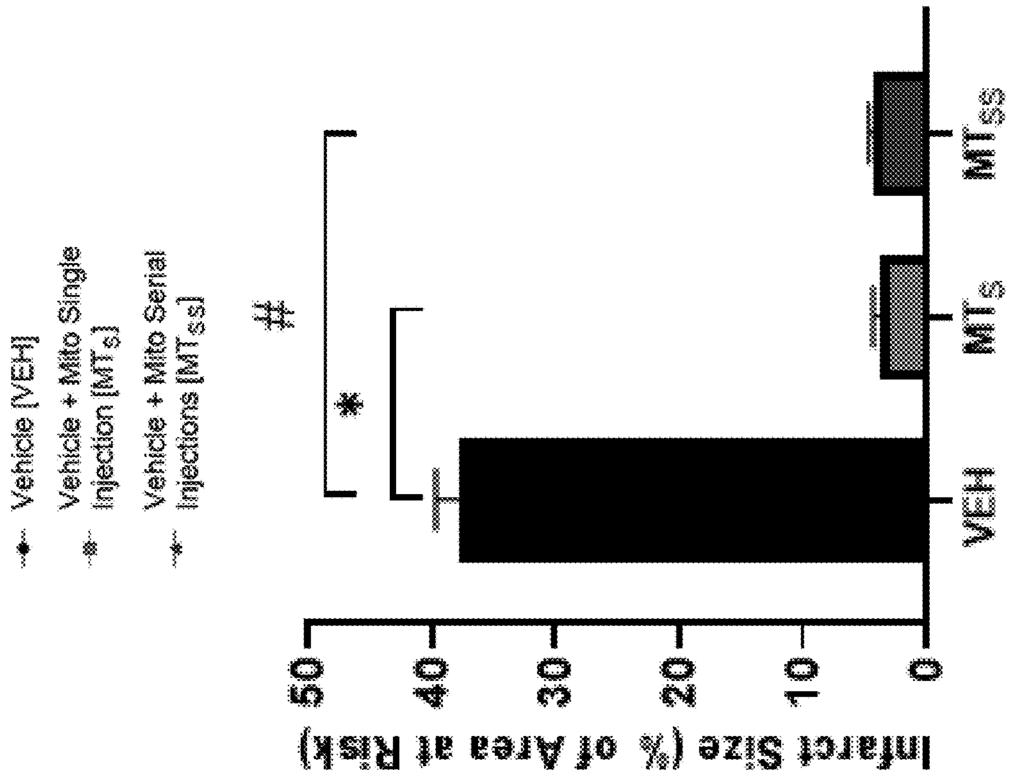
FIG. 6B is a bar graph illustrating infarct size as % of AAR.

FIGS. 6A-6E show representative area-at-risk (AAR) and infarct size. While there was no difference in the area-at-risk between treatment groups, infarct size was significantly reduced in both MT groups (VEH vs $MT_S$ and VEH vs $MT_{SS}$, $P<0.001$) (FIGS. 6A-6B). Both $MT_S$ and $MT_{SS}$ groups showed reduced infarct size and restoration of function at the end of the reperfusion period. Both $MT_S$ and $MT_{SS}$ groups showed enhanced myocardial function following IRI compared to VEH.

Regional Ischemia

CBF and LV function during RI were significantly decreased in $MT_S$, $MT_{SS}$, and Vehicle hearts as compared to the end of the intracoronary injection period (Table 2).

LV Pdev in $MT_S$s and $MT_{SS}$ was significantly higher than VEH (P=0.04 and $P<0.004$ respectively) during ischemia and continued throughout reperfusion (FIG. 4B). EKG changes related to ischemia were similar in all groups.

Post-Ischemia Comparison: Global Function after MT and a Subsequent Ischemic Event Following 120 minutes reperfusion, $MT_S$s and $MT_{SS}$ hearts showed significantly increased LV global function (Table 1). LV ejection fraction in Vehicle hearts was 36.1±2.1% and was significantly increased in $MT_S$ hearts, which had an LV ejection fraction of 53.6±2.9% ($P<0.001$ vs. VEH), and in $MT_{SS}$ hearts, which had an LV ejection fraction of 50.3±4.3% (P=0.04 vs. VEH) (FIG. 4A).

LV Pdev following 120 minutes reperfusion was significantly increased in $MT_S$ hearts (74.9±2.6 mmHg) and in $MT_{SS}$ hearts (69.9±3.7 mmHg) as compared to VEH hearts (57.8±2.4 mmHg) ($P<0.001$ and P=0.03 vs VEH, respectively) (FIG. 4B).

Figure 4C:
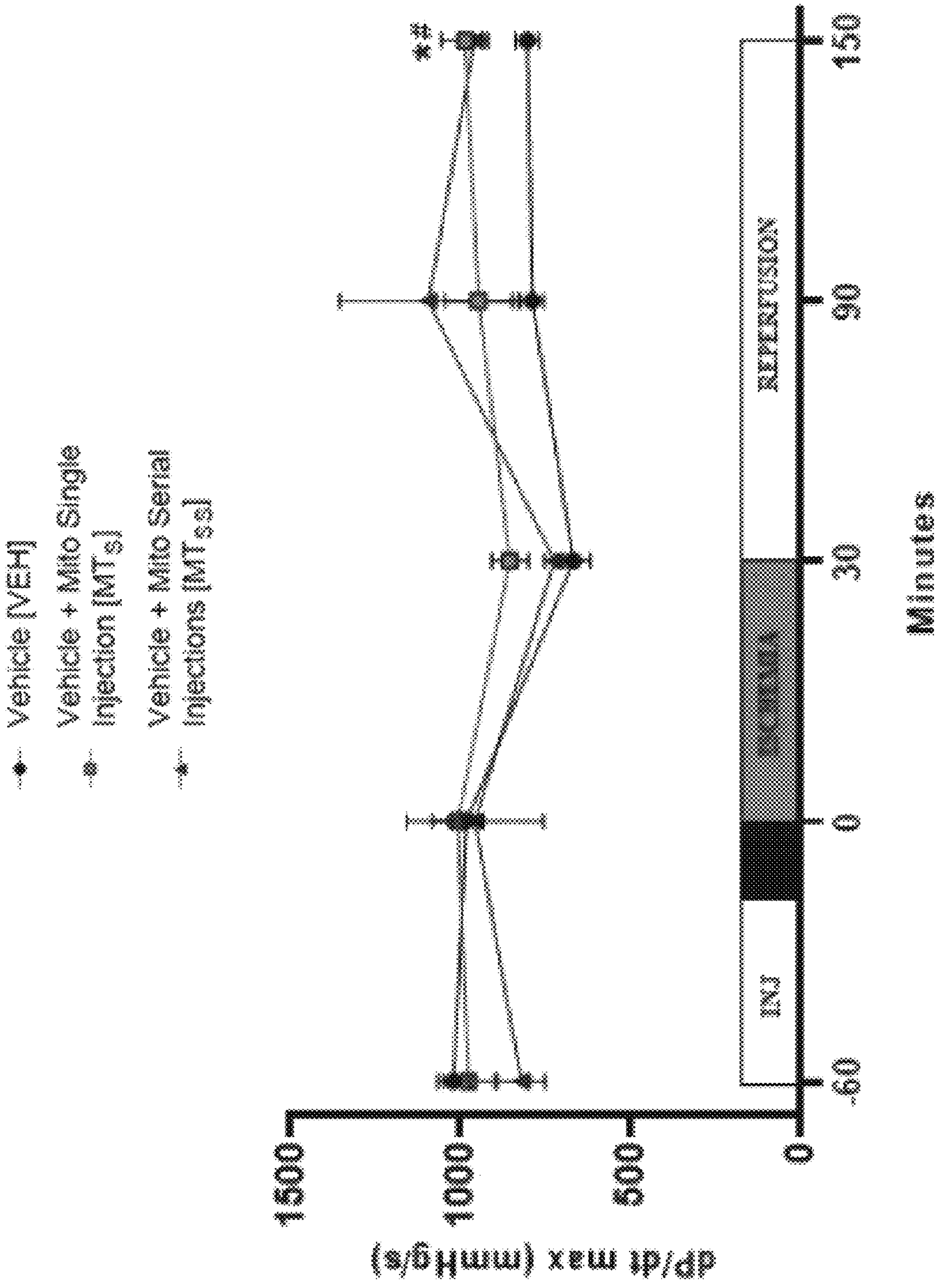
FIG. 4C is a line graph illustrating maximal rate of rise of left ventricular pressure (dP/dt max) during injection (INJ), post-injection/pre-ischemia (black box), ischemia, and reperfusion.

Similarly, LV dP/dt max following 120 minutes reperfusion was significantly increased in $MT_S$ (988±69 mmHg/s) and in $MT_{SS}$ (960±30 mmHg/s) as compared to VEH hearts (771±34 mmHg/s) (P=0.02 and P=0.004 vs VEH, respectively) (FIG. 4C).

Figure 4D:
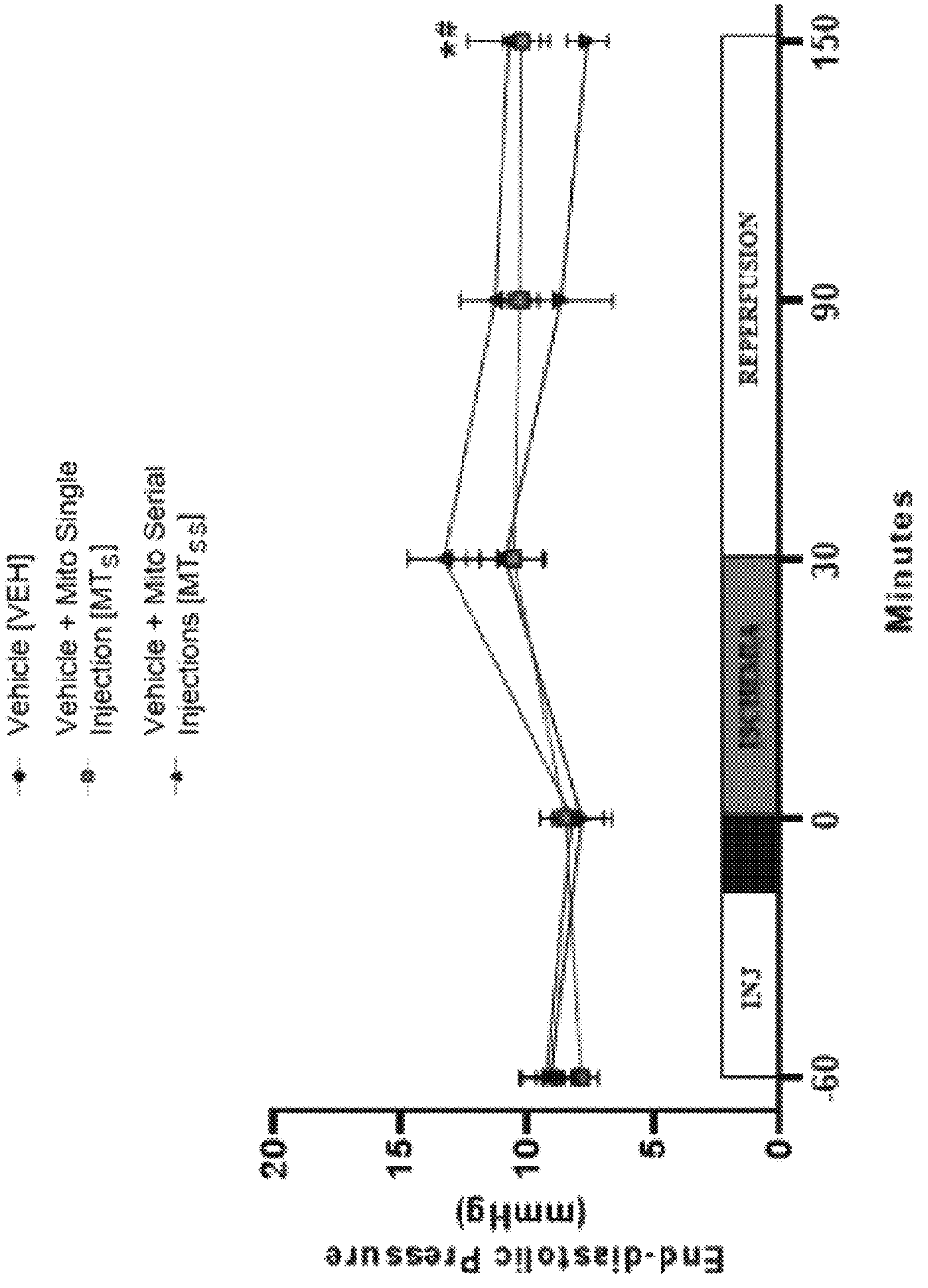
FIG. 4D is a line graph illustrating end diastolic left ventricular pressure during injection (INJ), post-injection/pre-ischemia (black box), ischemia, and reperfusion. All results are shown as mean±SEM for each group. *$P<0.05$ Single Injection vs. Vehicle; #$P<0.05$ Serial Injections vs. Vehicle.

LV Ped following 120 minutes reperfusion in $MT_S$s and $MT_{SS}$ was 8.0±0.6 mmHg and 8.2±0.1 mmHg, respectively, and was significantly decreased ($P<0.04$ for each) as compared to 11.8±1.3 mmHg in VEH hearts (FIG. 4D).

Both $MT_S$s and $MT_{SS}$ groups showed significantly enhanced global function following IRI compared to VEH.

No significant difference in LV ejection fraction, LV Pdev, LV dP/dt max or LV Ped was observed between the mitochondrial transplant groups, $MT_S$s and $MT_{SS}$, following 120 minutes reperfusion (FIGS. 4A-4D).

Post-Ischemia Comparison: Regional Function after MT and a Subsequent Ischemic Event Regional echocardiographic analysis at 120 minutes reperfusion showed significantly enhanced regional function in both $MT_S$s and $MT_{SS}$ groups (Table 2). Fractional shortening was increased in both $MT_S$ (26.7%±1.8%) and $MT_{SS}$ (25.0±2.6%) as compared to VEH (17.0±1.0%) ($P<0.001$ and P=0.04 for $MT_S$ and $MT_{SS}$ respectively vs VEH) (FIG. 5B).

2D global strain analysis at 120 minutes of reperfusion (time point 150) was −18.5±0.8% in $MT_S$ and −20.9±1.1% in $MT_{SS}$ as compared to −12.9±0.8% in VEH (P=0.002 and P=0.003 for $MT_S$ and $MT_{SS}$ respectively vs VEH) (FIG. 5C).

Segmental shortening by sonomicrometry following 120 minutes of reperfusion was significantly increased in both $MT_S$ and $MT_{SS}$ (11.1±1.2% and 11.8±0.5%, respectively) as compared to 7.9±0.5% in VEH (P=0.03 and $P<0.001$ for $MT_S$ and $MT_{SS}$ respectively vs VEH) (FIG. 5D).

Both $MT_S$ and $MT_{SS}$ groups showed significantly enhanced regional function following IRI compared to VEH.

Coronary Blood Flow

No differences in CBF were observed within or between groups during equilibrium and at the end of ischemia (time point 150) (Table 2).

Figure 9A:
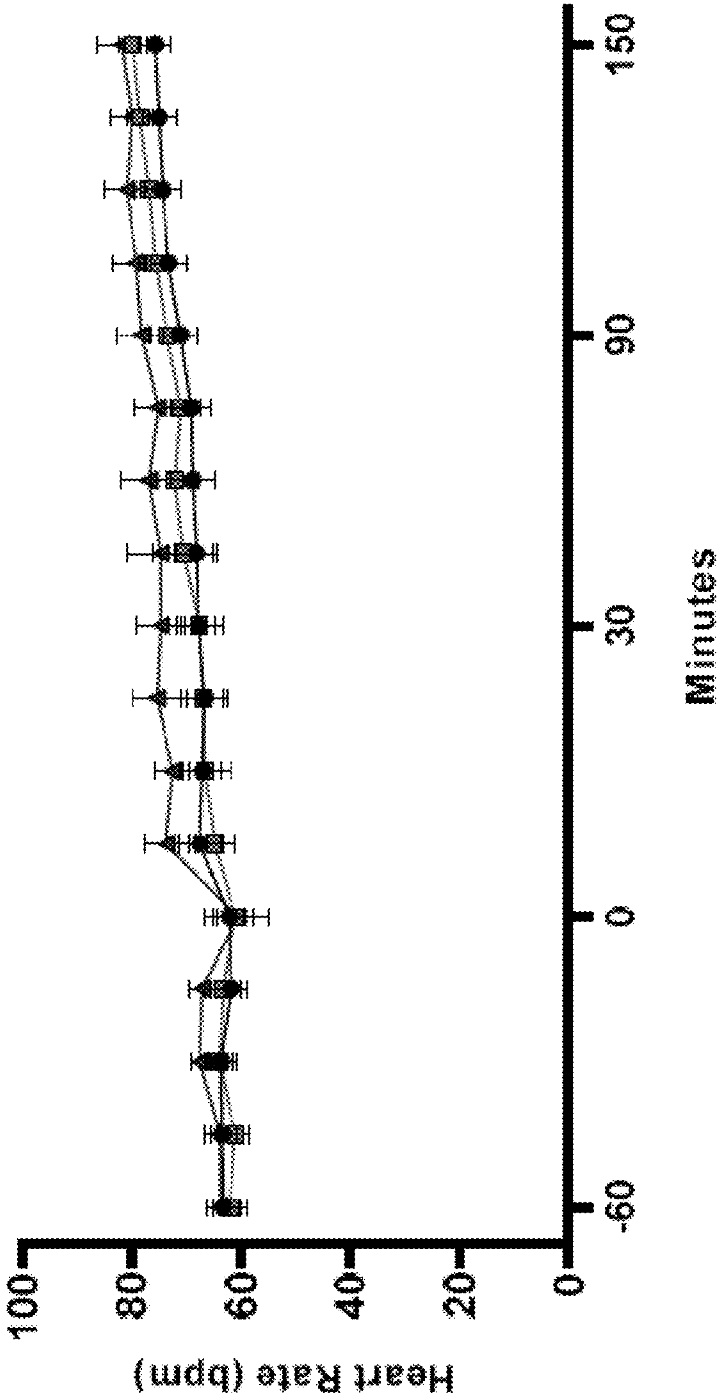
FIG. 9A is a line graph illustrating heart rate during a representative experiment.
Figure 9B:
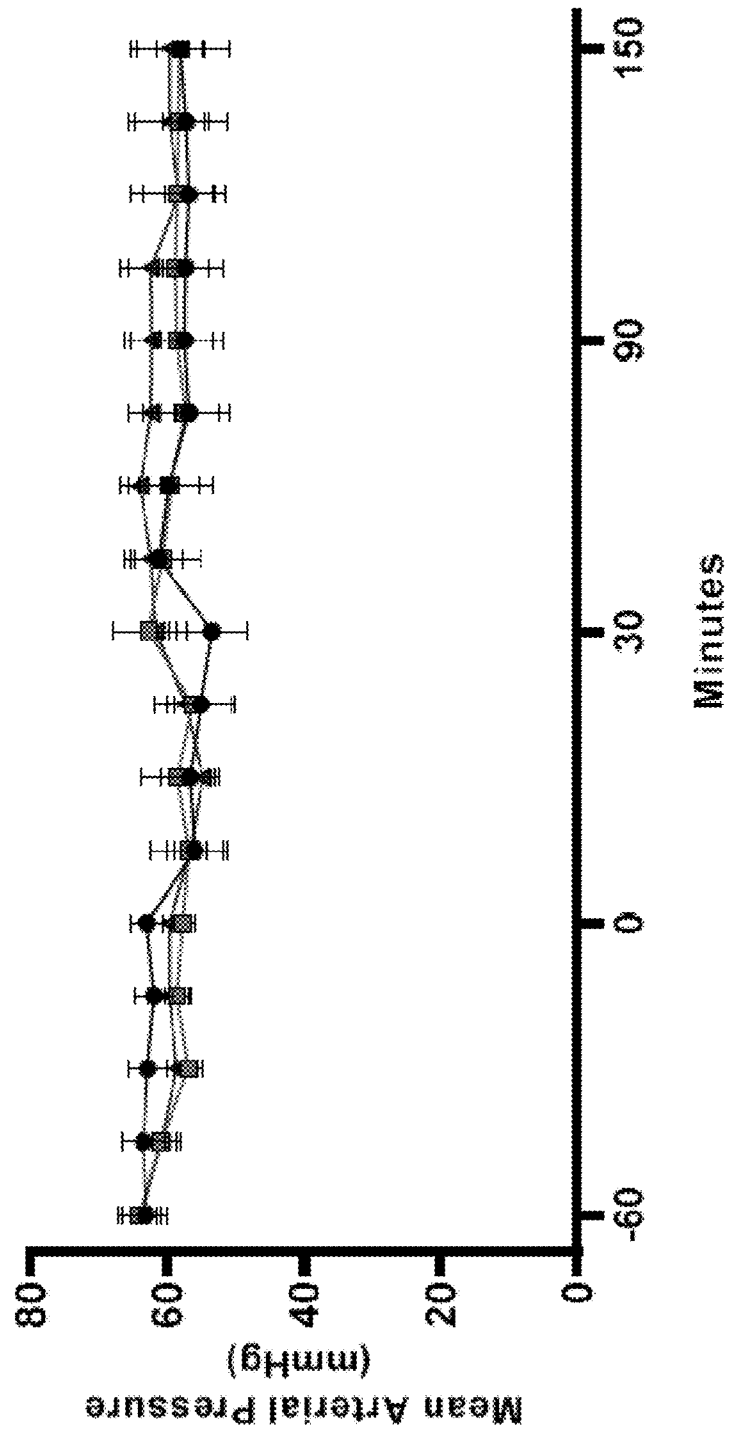
FIG. 9B is a line graph illustrating mean arterial pressure during a representative experiment.

CBF in both $MT_S$ and $MT_{SS}$ was significantly increased throughout reperfusion as compared to VEH (P=0.04 for each at 120 minutes reperfusion). FIGS. 9A-9B show heart rate and mean arterial pressure. No differences in HR and MAP related to the increased CBF were observed within or between groups (FIGS. 9A-9B).

AAR and Infarct Size

The left ventricular AAR (% of LV mass) was 43.6%±2.10% in $MT_S$, 44.6%±2.8% in $MT_{SS}$, and 40.6%±1.5% in Vehicle hearts (FIG. 6A). No significant difference was observed within or between groups for AAR.

Infarct size (% AAR) was 37.9%±1.8% in VEH and was significantly decreased in $MT_S$ (3.8%±0.5%; P<0.001 vs VEH) and in $MT_{SS}$ (4.2%±0.5%; P<0.001 vs VEH) (FIGS. 6B-6E). Both $MT_S$ and $MT_{SS}$ groups showed significantly reduced infarct size following IRI compared to VEH.

There was no significant difference observed in infarct size (% AAR) between $MT_S$ and $MT_{SS}$ hearts (P=0.55).

Figure 6C:
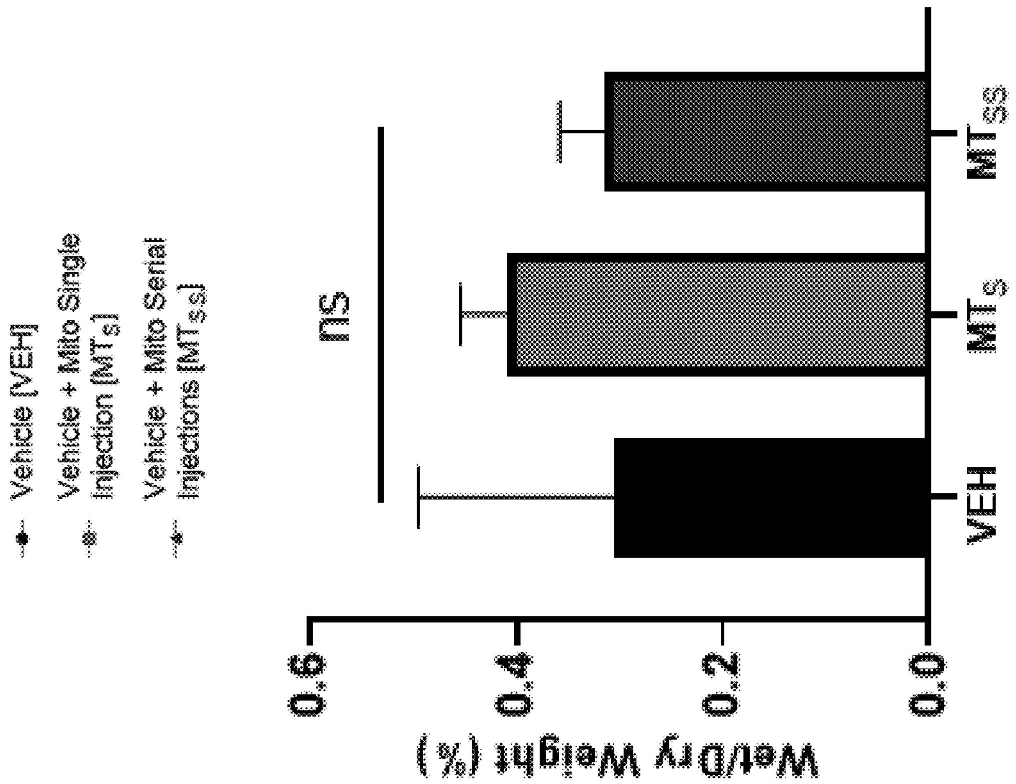
FIG. 6C is a bar graph illustrating wet weight-to-dry weight ratios.
Figure 6D:
FIG. 6D shows representative examples of the infarct size determined by triphenyl tetrazolium chloride staining in VEH (top), $MT_S$ (middle) and $MT_{SS}$ (bottom).
Figure 6E:
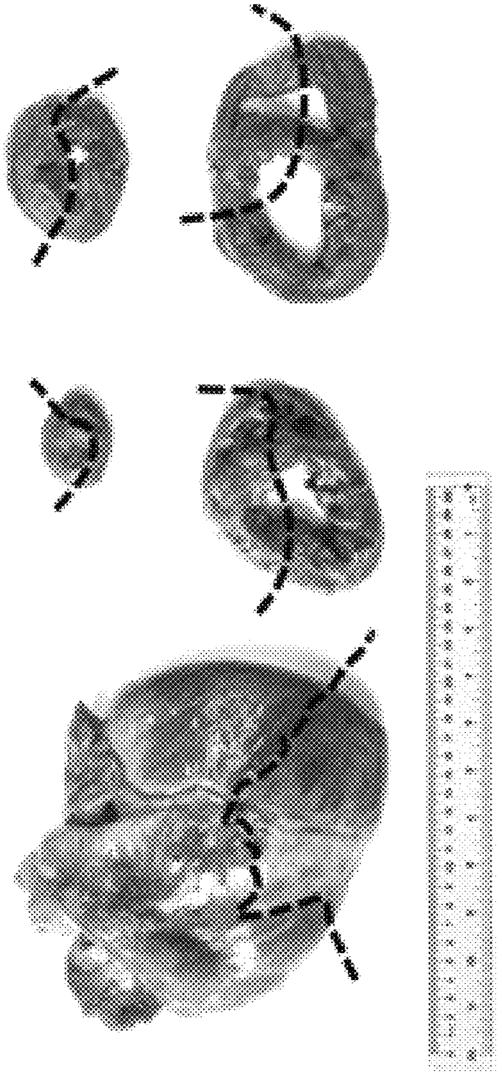
FIG. 6E shows representative images of area-at-risk (AAR) and infarct size. All results are shown as mean±SEM for each group. *P<0.05 Single Injection vs. Vehicle; #P<0.05 Serial Injections vs. Vehicle. ns, no significant difference at P<0.05 detected.

No significant difference in the wet weight-to-dry weight ratio was observed between groups ($MT_S$ 40.9%±0.1% vs VEH 30.5%±0.2%, P=0.51; $MT_{SS}$ 31.5%±0.1% vs VEH, P=0.8) (FIG. 6C).

Figure 10A:
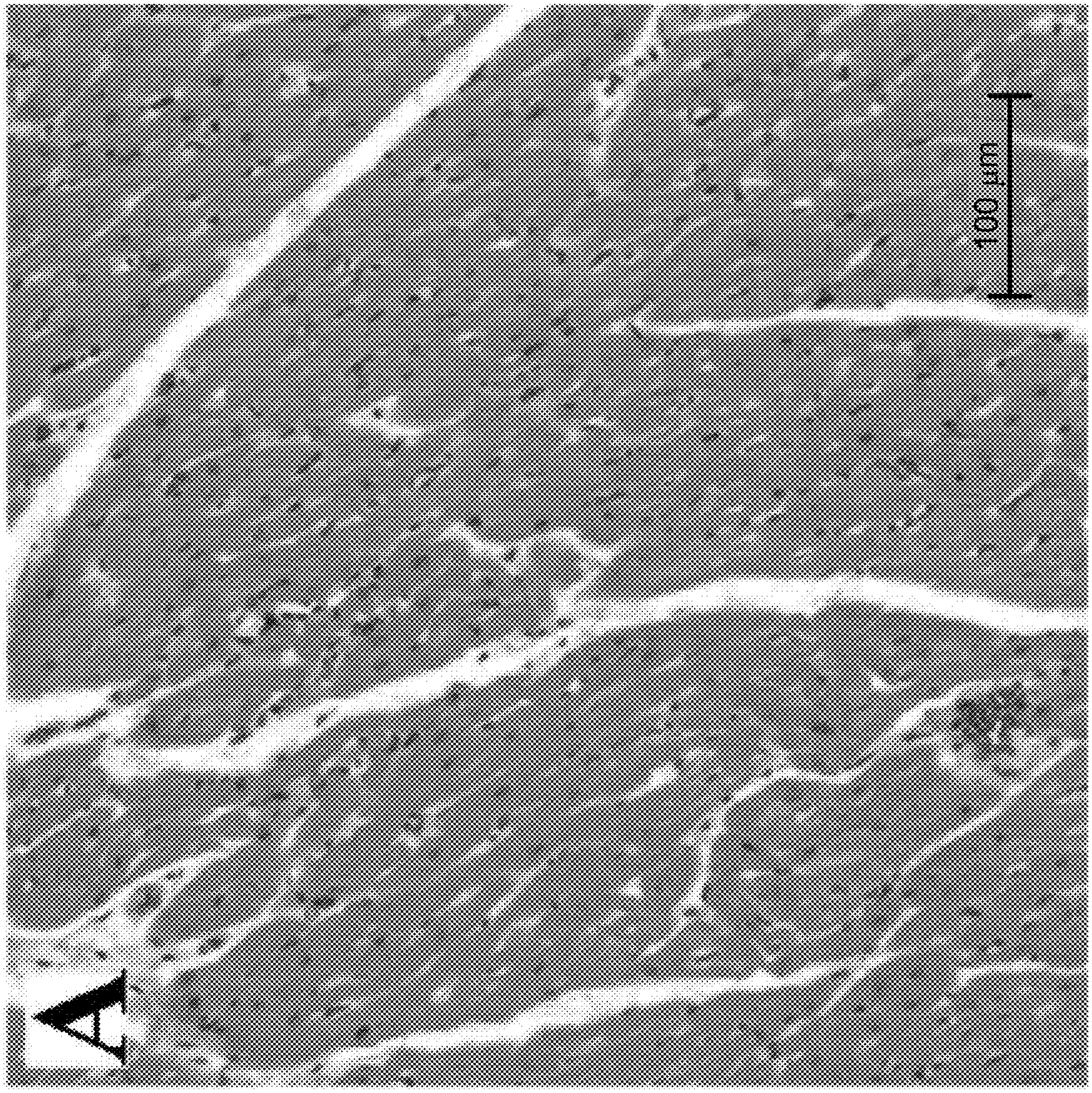
FIG. 10A shows tissue sections from representative vehicle group hearts.
Figure 10B:
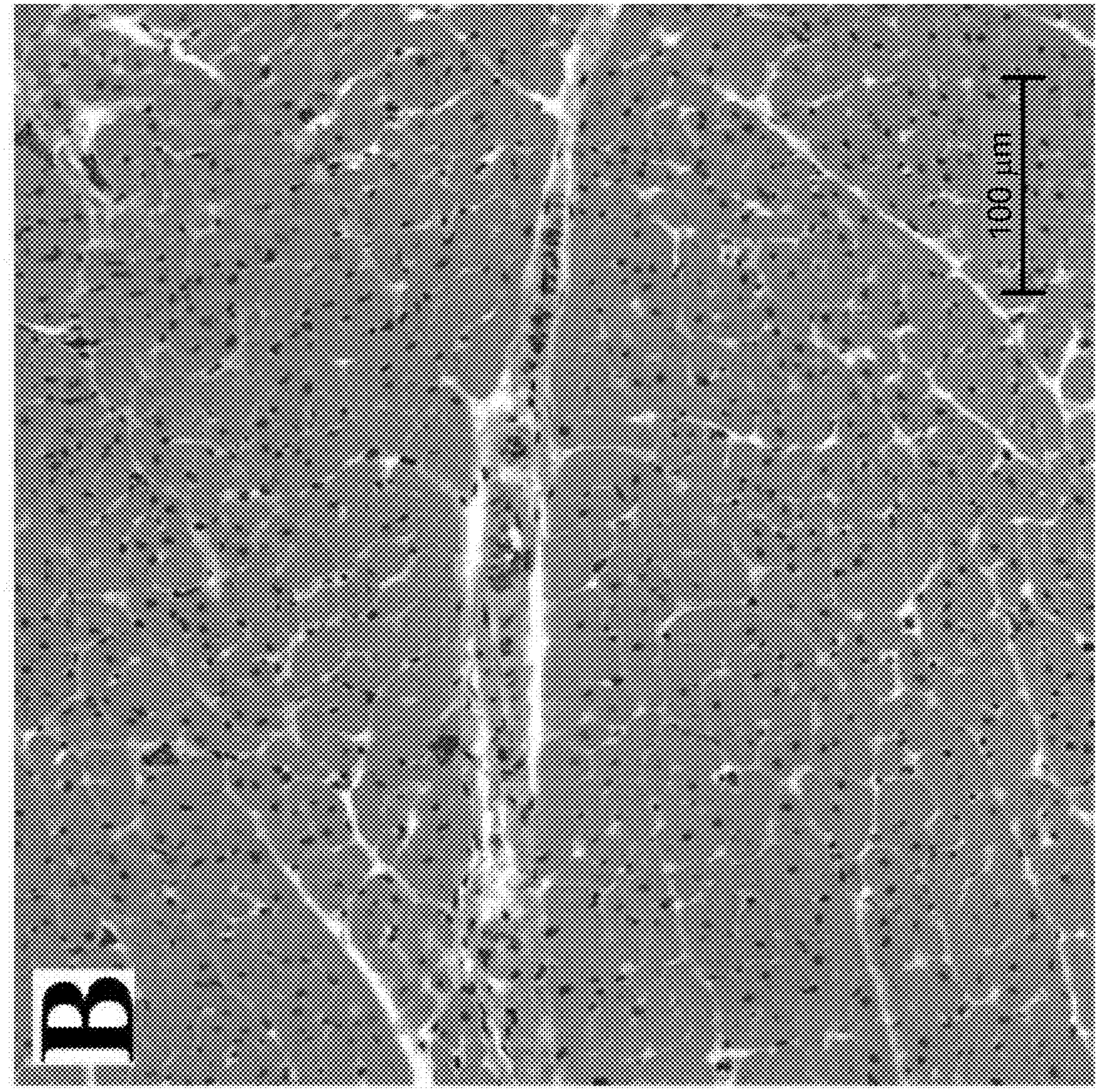
FIG. 10B shows tissue sections from representative $MT_S$ group hearts.
Figure 10C:
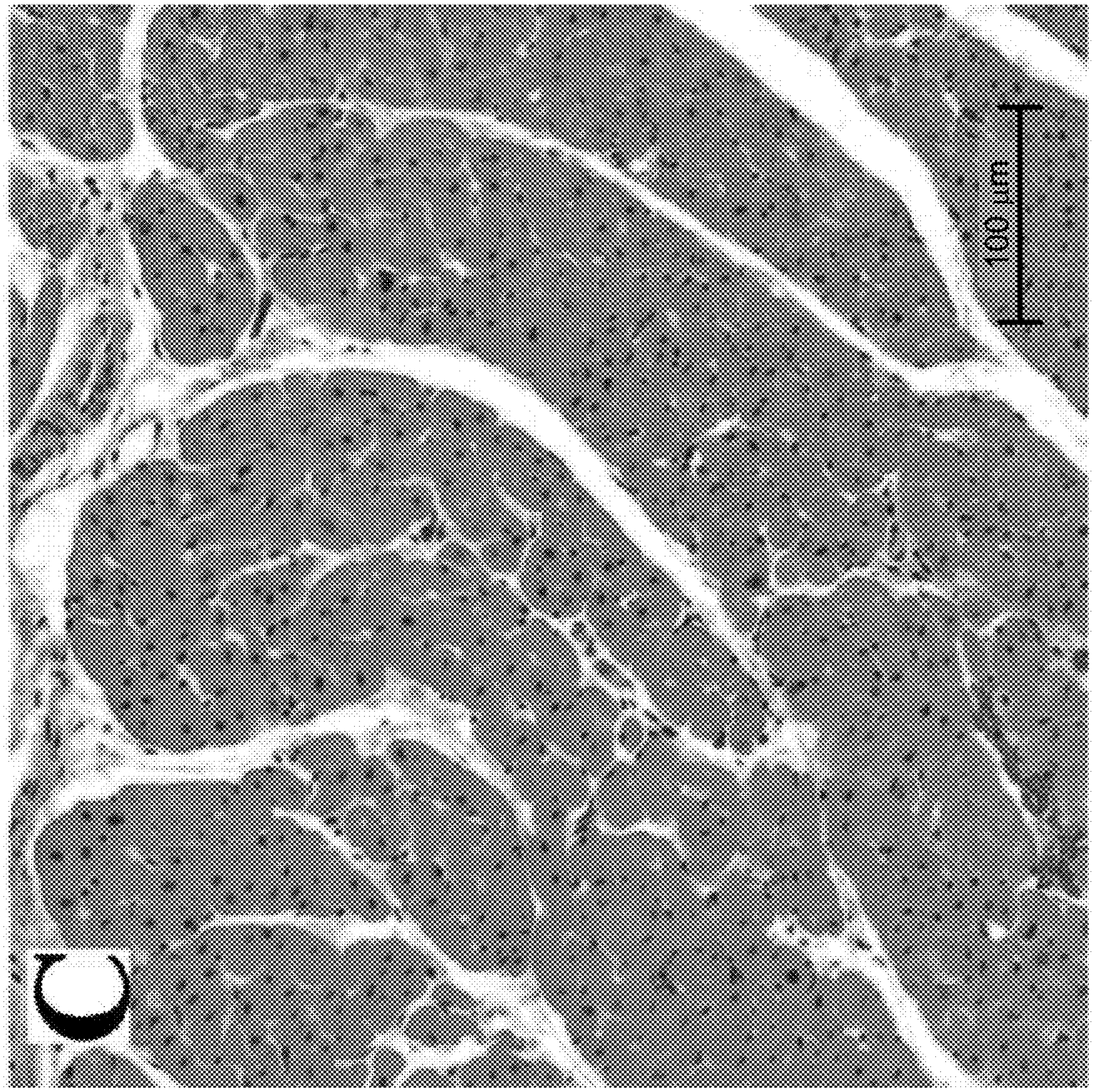
FIG. 10C shows tissue sections from representative $MT_{SS}$ group hearts.

Example 3: MT Protects Tissue and Mitochondrial Structure and Function from IRI-Related Damage Histology and Transmission Electron Microscopy FIGS. 10A-10C show representative myocardial tissue injury at the end of reperfusion. H&E analysis showed significantly less necrosis and inflammatory cell infiltration in MT hearts when compared with VEH (FIGS. 10A-10C). Tissue sections from vehicle group hearts (FIG. 10A) show significantly more severe necrosis and inflammatory cell infiltration as compared with mitochondrial transplantation groups $MT_S$ and $MT_{SS}$ hearts (FIGS. 10B and 10C, respectively). MT reduced organ, tissue, and cell damage associated with IRI.

Figure 7A:
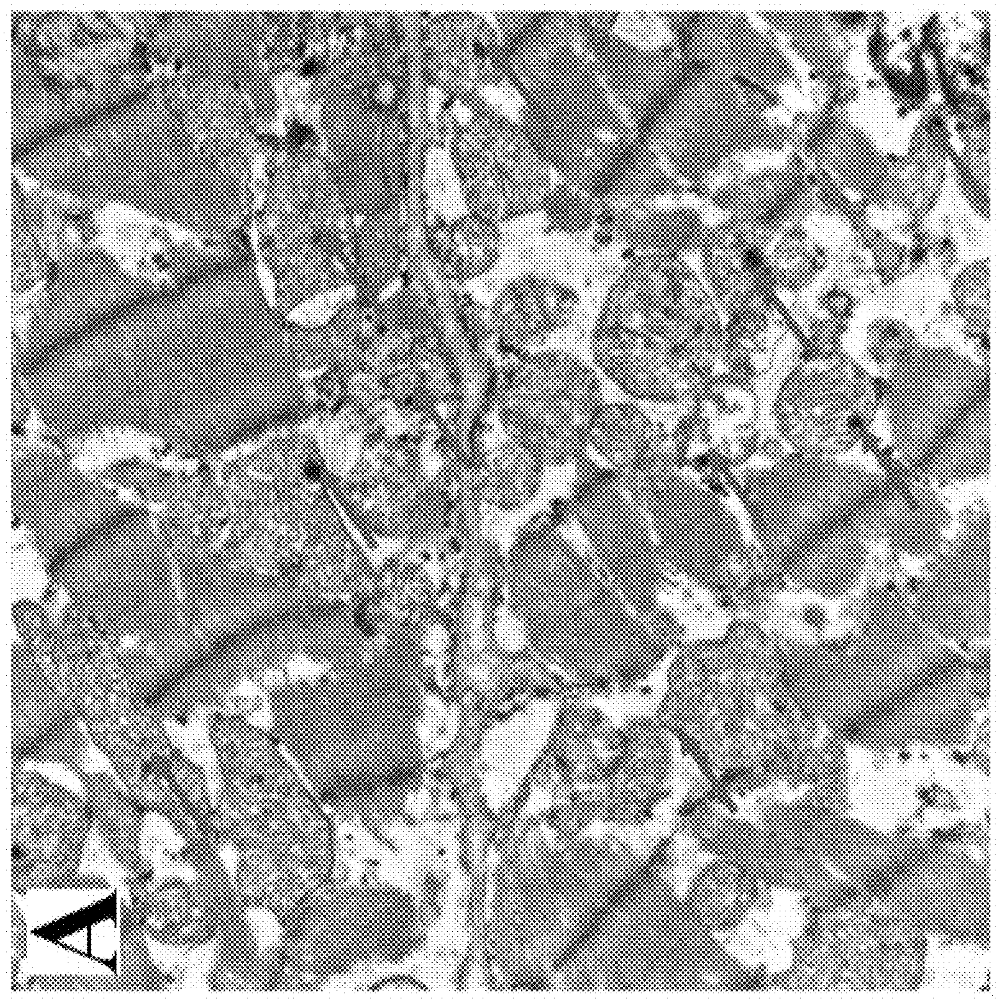
FIG. 7A shows electron microscopy to examine mitochondrial structure of representative VEH heart.
Figure 7B:
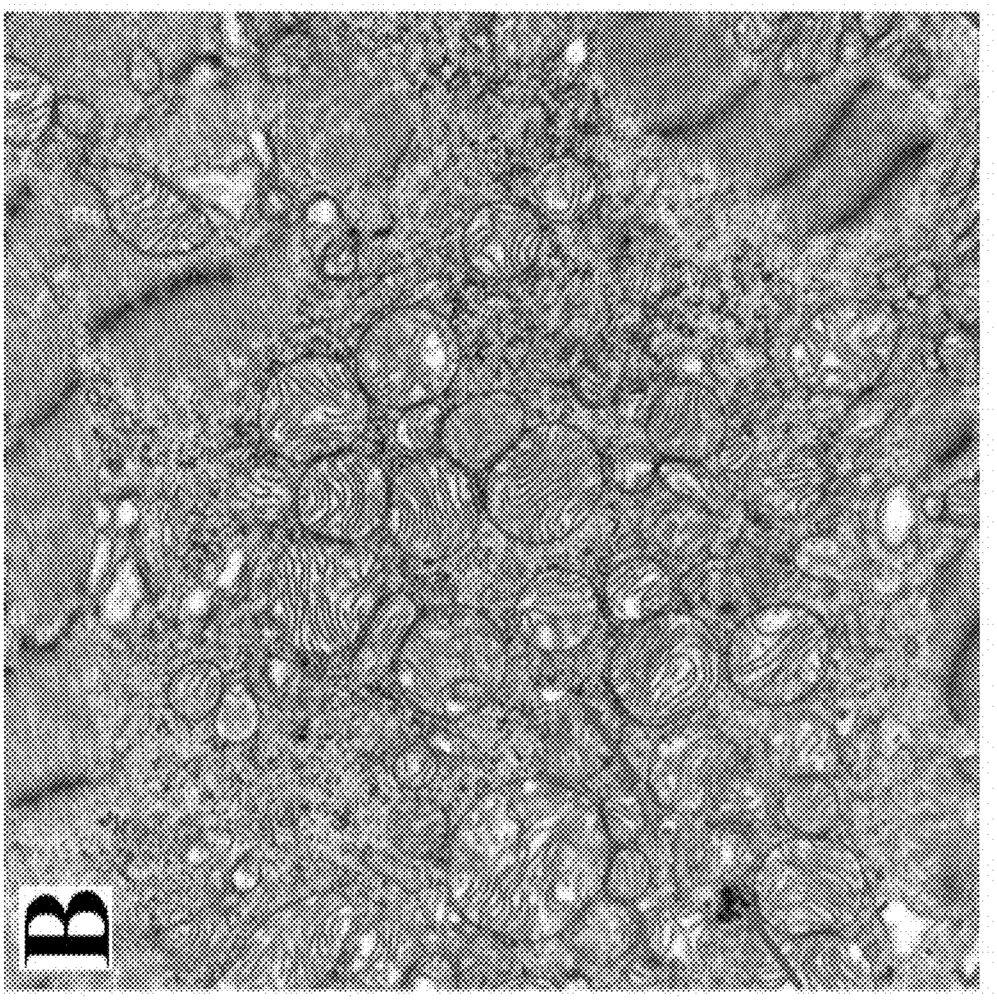
FIG. 7B shows electron microscopy to examine mitochondrial structure of representative $MT_S$ heart.
Figure 7C:
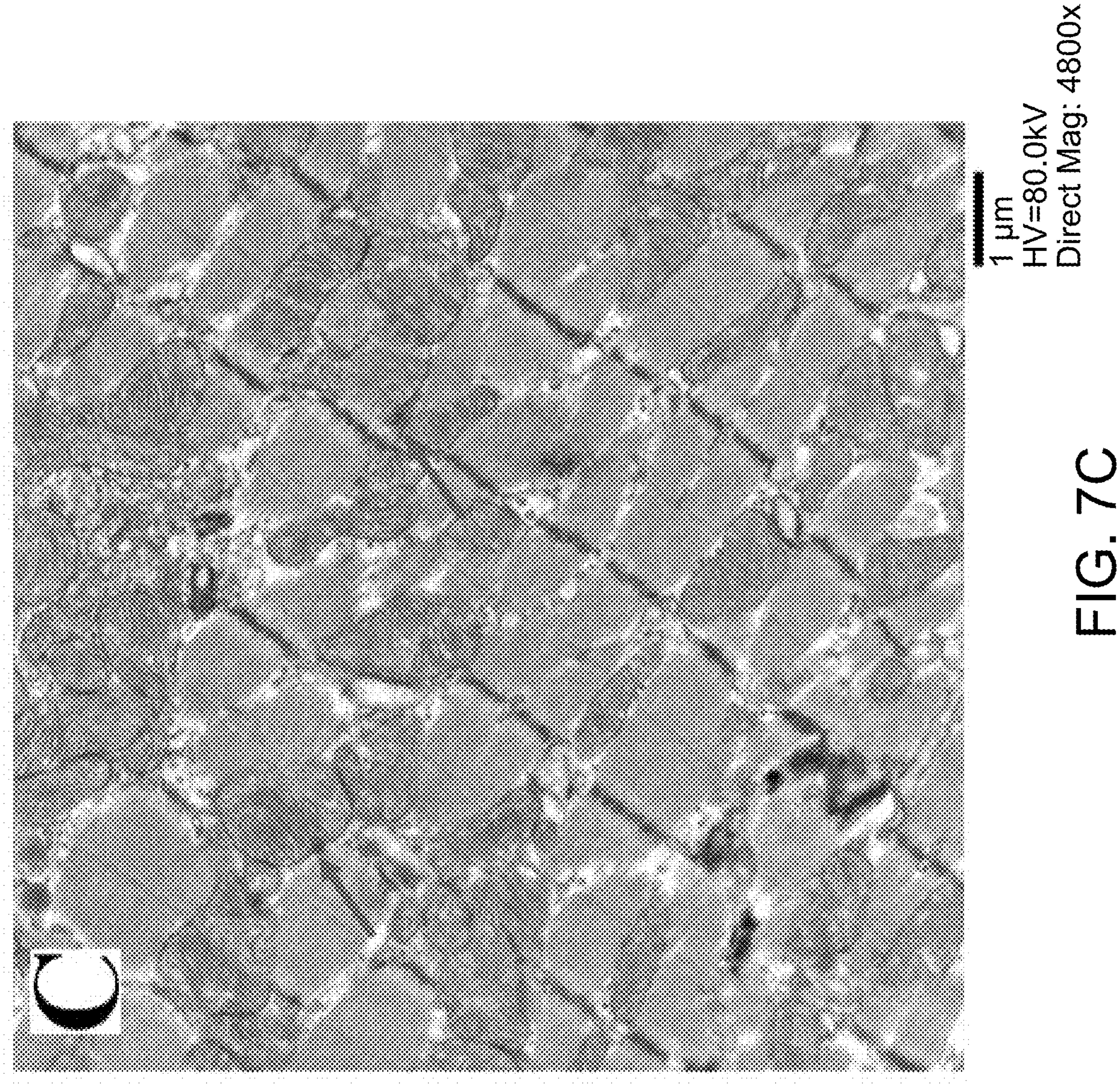
FIG. 7C shows electron microscopy to examine mitochondrial structure of representative $MT_{SS}$ heart.

Electron microscopy confirmed mitochondrial damage and contraction bands in VEH that were not present in MT hearts (FIGS. 7A-7C). Electron microscopy analysis showed contraction bands, electron translucent and swollen mitochondria, with a greater intermembrane space, enlarged ridges, disrupted matrix, and calcium accumulation (arrows) in vehicle hearts (FIG. 7A). In VEH hearts, mitochondria demonstrated a swollen shape, electron translucence, greater intermembrane space, enlarged ridges, and disrupted matrix with calcium accumulation (FIG. 7A). MT hearts showed preserved mitochondrial structure, and only traces of calcium accumulation (FIGS. 7B-7C). Both $MT_S$ and $MT_{SS}$ groups displayed significantly improved mitochondrial structure following IRI compared to VEH. Both $MT_S$ and $MT_{SS}$ groups protected mitochondrial structure and function from IRI-associated damage and dysfunction. Both $MT_S$ and $MT_{SS}$ groups reduced mitochondrial structure and function damage associated with IRI.

Pint Mag: 17500× @ 7.0 in. Camera: Hamamatsu ORCA HR Camera, Exposure (ms) 3000; Gain: 1.7, Bin: 1. Gamma: 1.00; no sharpening, normal contrast.

TABLE 1

Measurements of global function during the experiment.

| | | (Minutes) | | | | |
|---|---|---|---|---|---|---|
| | Groups | −60 | 0 | 30 | 90 | 150 |
| LV Ejection fraction (%) | V | 52.6 ± 1.6 | 52.3 ± 1.6 | 30.7 ± 2.0 | 32.1 ± 2.7 | 36.1 ± 2.1 |
| | $MT_S$ | 50.2 ± 1.8 | 60.2 ± 2.1 | 34.8 ± 2.7 | 48.0 ± 2.4 | 53.6 ± 2.9 |
| | $MT_{SS}$ | 49.9 ± 1.8 | 59.8 ± 2.1 | 35.9 ± 2.8 | 49.2 ± 3.0 | 50.3 ± 4.3 |
| p value | ($MT_S$ vs V) | .50 | **.03** | .35 | **.001** | **<.001** |
| | ($MT_{SS}$ vs V) | .50 | **.04** | .35 | **.005** | **.04** |
| LVdevP (mmHg) | V | 71.3 ± 1.6 | 71.1 ± 2.0 | 57.7 ± 2.0 | 63.2 ± 1.9 | 57.8 ± 2.4 |
| | $MT_S$ | 70.4 ± 1.6 | 73.5 ± 1.7 | 67.7 ± 3.6 | 71.8 ± 2.2 | 74.9 ± 2.6 |
| | $MT_{SS}$ | 71.6 ± 1.8 | 73.9 ± 2.4 | 70.5 ± 2.3 | 70.2 ± 4.3 | 69.9 ± 3.7 |

TABLE 1-continued

Measurements of global function during the experiment.

| | | (Minutes) | | | | |
|---|---|---|---|---|---|---|
| | Groups | −60 | 0 | 30 | 90 | 150 |
| p value | ($MT_S$ vs V) | .89 | .61 | **.04** | **.02** | **<.001** |
| | ($MT_{SS}$ vs V) | .89 | .61 | **.004** | .27 | **.03** |
| dP/dt max (mmHg/s) | V | 1019 ± 58 | 961 ± 47 | 666 ± 60 | 796 ± 34 | 771 ± 34 |
| | $MT_S$ | 1059 ± 52 | 1207 ± 50 | 855 ± 56 | 948 ± 99 | 988 ± 69 |
| | $MT_{SS}$ | 1028 ± 31 | 1325 ± 165 | 726 ± 30 | 1095 ± 261 | 960 ± 30 |
| p value | ($MT_S$ vs V) | .90 | **.003** | .10 | .48 | **.02** |
| | ($MT_{SS}$ vs V) | .90 | .26 | .39 | .48 | **.004** |
| LVPed (mmHg) | V | 7.7 ± 0.7 | 7.4 ± 0.9 | 11.4 ± 1.0 | 11.7 ± 1.0 | 11.8 ± 1.3 |
| | $MT_S$ | 8.9 ± 0.9 | 8.4 ± 0.1 | 13.0 ± 1.7 | 9.6 ± 1.5 | 8.0 ± 0.6 |
| | $MT_{SS}$ | 9.1 ± 0.3 | 7.4 ± 0.4 | 11.0 ± 2.9 | 7.5 ± 1.2 | 8.2 ± 0.1 |
| p value | ($MT_S$ vs V) | .44 | .59 | .91 | .32 | **.04** |
| | ($MT_{SS}$ vs V) | .32 | .98 | .91 | .23 | **.04** |

Minutes: −60 = Baseline; 0 = End of Pre-Ischemia; 30 = End of ischemia; 90 = 1$^{st}$ Hour of Reperfusion; 150 = 2$^{st}$ Hour of Reperfusion.

Single Injection ($MT_S$), Vehicle (V), Serial Injections ($MT_{SS}$). Left ventricle (LV). Left ventricular developed pressure (LVdevP).

Significant differences less than or equal to P < .05 are shown in bold type.

TABLE 2

Measurements of regional function during the experiment

| | | (Minutes) | | | | |
|---|---|---|---|---|---|---|
| | Groups | −60 | 0 | 30 | 90 | 150 |
| LAD flow (ml/min) | V | 18.1 ± 1.6 | 17.3 ± 1.6 | 0.8 ± 0.3 | 10.2 ± 1.5 | 11.4 ± 1.8 |
| | $MT_S$ | 19.2 ± 1.8 | 20.5 ± 1.5 | 1.0 ± 0.1 | 19.8 ± 1.6 | 19.0 ± 2.5 |
| | $MT_{SS}$ | 17.9 ± 2.2 | 17.5 ± 0.2 | 1.6 ± 0.6 | 17.4 ± 1.7 | 17.8 ± 1.4 |
| p value | ($MT_S$ vs V) | .25 | .26 | .63 | **.003** | **.04** |
| | ($MT_{SS}$ vs V) | .52 | .26 | .25 | **.01** | **.04** |
| LV Echo Fractional Shortening (%) | V | 25.5 ± 0.9 | 25.4 ± 0.9 | 14.1 ± 1.0 | 14.8 ± 1.4 | 17.0 ± 1.0 |
| | $MT_S$ | 24.7 ± 1.1 | 29.6 ± 1.3 | 16.1 ± 1.4 | 23.4 ± 1.3 | 26.7 ± 1.8 |
| | $MT_{SS}$ | 24.5 ± 1.2 | 29.4 ± 1.4 | 16.7 ± 1.6 | 24.0 ± 1.9 | 25.0 ± 2.6 |
| p value | ($MT_S$ vs V) | .81 | .05 | .37 | **.001** | **<.001** |
| | ($MT_{SS}$ vs V) | .81 | .08 | .37 | **.01** | **.04** |
| LV Echo Strain (%) | V | −21.9 ± 1.1 | −21.7 ± 1.1 | −13.5 ± 0.7 | −13.1 ± 0.9 | −12.9 ± 0.8 |
| | $MT_S$ | −21.4 ± 1.3 | −22.5 ± 1.3 | −14.2 ± 0.9 | −16.5 ± 0.7 | −18.5 ± 0.8 |
| | $MT_{SS}$ | −21.5 ± 2.9 | −22.4 ± 2.2 | −16.2 ± 1.4 | −20.0 ± 0.5 | −20.9 ± 1.1 |
| p value | ($MT_S$ vs V) | .99 | .10 | .53 | **.02** | **.002** |
| | ($MT_{SS}$ vs V) | .99 | .10 | .53 | **.001** | **.003** |
| LV Segmental shortening (%) | V | 12.0 ± 0.3 | 12.3 ± 0.4 | 6.0 ± 0.5 | 9.0 ± 0.7 | 7.9 ± 0.5 |
| | $MT_S$ | 12.3 ± 0.7 | 13.6 ± 1.1 | 7.8 ± 1.3 | 11.7 ± 0.9 | 11.1 ± 1.2 |
| | $MT_{SS}$ | 12.1 ± 0.6 | 13.5 ± 1.2 | 8.7 ± 1.6 | 12.5 ± 0.3 | 11.8 ± 0.5 |
| p value | ($MT_S$ vs V) | .93 | .61 | .31 | **.04** | **.03** |
| | ($MT_{SS}$ vs V) | .93 | .61 | .31 | **.002** | **<.001** |

Minutes: −60 = Baseline; 0 = End of Pre-Ischemia; 30 = End of ischemia; 90 = 1$^{st}$ Hour of Reperfusion; 150 = 2$^{st}$ Hour of Reperfusion.

Single Injection ($MT_S$), Vehicle (V), Serial Injections ($MT_{SS}$). Left anterior descending artery (LAD). Left ventricle (LV).

Significant differences less than or equal to P < .5 are shown in bold type.

Example 4: MT Protects Kidney Function from Renal IRI

Experiments were performed to investigate that mitochondria transplantation by intra-arterial injection in renal Ischemia-Reperfusion Injury. These experiments showed therapeutic use of autologous MT by intra-arterial injection for renal protection in a swine model of bilateral IRI.

Yorkshire pigs (n=12; female, 40-50 kg) were anesthetized. The left or right femoral artery and right carotid artery were cannulated with angiography sheaths. The abdominal aorta was angiographically inspected. Selective catheterization of the renal arteries was performed using multipurpose guide-catheters and renal arteries were injected with iodinated contrast medium. Subsequent bilateral temporary occlusion with balloon-catheters of appropriate size was achieved. After 60 minutes of ischemia, the balloons were deflated, and the animal was reperfused for 24 hours. Mitochondria ($1\times10^9$/resuspended in 5 mL respiration buffer, MT) or respiration buffer alone (Vehicle, V) were delivered as a single bolus in each of the renal arteries at the time of reperfusion. Renal function (renal output, serum creatinine, estimated glomerular filtration rate, blood urea nitrogen, and serum potassium) was compared between the two groups using two-way repeated measures analysis of variance (ANOVA) with Bonferroni adjustment. Markers of systemic inflammatory response and organs function, before and after autologous mitochondrial transplantation, were also measured.

No differences were observed between the MT and V groups before inducing ischemia in terms of renal function. Following 60 minutes of ischemia, both groups had significant decrease in renal function. Localized MT injection into the kidneys had no effect on heart rate or mean arterial pressure compared to vehicle treated animals. Additionally, no detectable difference in markers of systemic inflammatory response and organ function were observed in the MT group.

At the end of 24 hours of reperfusion, animals treated with mitochondrial transplantation showed significantly improved renal function in terms of renal output (2.8±0.8 mL/kg/h vs 0.6±0.3 mL/kg/h, p=0.02), serum creatinine (2.8±0.5 mg/dL vs 6.9±0.6 mg/dL, p<0.01), estimated glomerular filtration rate (1.6±0.2 ml/min/kg vs 0.9±0.05 ml/min/kg, p=0.03), blood urea nitrogen (19.6±4.5 mg/dL vs 36.7±5.2 mg/dL, p<0.01) and serum potassium (4.8±0.5 mmoL/L vs 6.6±0.1 mmoL/L, p=0.01).

Mitochondrial transplantation by intra-arterial injection provides renal protection from ischemia-reperfusion injury, significantly enhancing renal function. These results suggest that this strategy can be used to protect kidneys from ischemia-reperfusion injury, thus reducing morbidity and mortality in several clinical scenarios such as kidney transplantation, hypotensive events, and procedures requiring bypass or mechanical circulatory support.

Example 5: Mitochondrial Transplantation for Myocardial Protection in Diabetic Following Ischemia Experiments were performed to investigate the efficacy of mitochondrial transplantation (MT) in providing for cardioprotection from warm global ischemia and reperfusion in the diabetic heart.

Ex-vivo perfused hearts from Zucker diabetic fatty (ZDF fa/fa) rats (n=6 per group) were used. Mitochondria isolated from the same diabetic donor ($MT_{ZDF}$) or from non-diabetic Zucker lean (ZL+/?) rats ($MT_{ZL}$) were injected at reperfusion after 30 min of warm global ischemia. Vehicle group (VEH) did not receive any mitochondria. Hearts were reperfused retrogradely on a Langendorff apparatus at 37° C. for 2 h. Left ventricular (LV) pressure parameters were measured using an intraventricular balloon and infarct size was assessed with the use of 2,3,5-Triphenyltetrazolium chloride (TTC) staining. Data are expressed as mean±standard error of the mean.

Left ventricular developed pressure (LVdevP) and end diastolic pressure (EDP) were similar among groups at baseline (LVdevP: MTZDF: 117.3±2.4 mmHg vs MTZL: 117.7±2.8 mmHg vs VEH: 120.4±2.4 mmHg, p>0.05; EDP: MTZDF: 6.5±0.7 mmHg vs MTZL: 7.4±0.3 mmHg vs VEH: 6.6±0.5 mmHg, p>0.05). After 2 h reperfusion, LVdevP was significantly increased in MTZDF and MTZL groups compared with VEH group (MTZDF:92.8±5.2 mmHg vs MTZL: 110.7±2.4 mmHg vs VEH: 44.3±5.9 mmHg; p<0.01 in both cases), while EDP was significantly decreased (MTZDF 12.1±1.3 mmHg vs MTZL 8.6±0.8 mmHg vs VEH: 18.6±1.5 mmHg; p=0.016 for MTZDF vs VEH and p<0.01 for MTZL vs VEH). Total tissue ATP content was significantly increased in both MT groups compared with VEH group (MTZDF: 18.9±1.5 mmol/mg protein/mg tissue vs MTZL: 28.1±2.3 mmol/mg protein/mg tissue vs VEH: 13.1±0.5 mmol/mg protein/mg tissue; p=0.018 for MTZDF vs VEH and p<0.01 for MTZL vs VEH). Infarct size was significantly decreased in the MT groups (MTZDF: 11.8±0.7% vs MTZL: 9.9±0.5% vs VEH: 52.0±1.4%; p<0.01 in both cases).

Example 6: Mitochondrial Transplantation for Myocardial Protection

PHASE 1: SAFETY AND BIODISTRIBUTION OF INTRACORONARY DELIVERY OF MITOCHONDRIA. Myocardial uptake and biodistribution of mitochondria. Myocardial uptake and biodistribution of mitochondria were evaluated by intracoronary injection of $^{18}$F-rhodamine-6G-labeled mitochondria ($6\times10^9$) in the LCA (n=2). FIGS. 11A-11G show biodistribution and myocardial uptake of autologous mitochondria by intracoronary delivery. Whole-body positron emission tomographic scan images showed that the transplanted mitochondria were located specifically in the left ventricle (FIGS. 11A-11C). $^{18}$F-tracer signals were also present in the arterial sheath and in the right carotid artery where the coronary catheter was placed, and a small amount of tracer was detected in the descending aorta (FIGS. 11A-11C). There was no evidence of significant tracer accumulation in any other organs. Myocardial cellular uptake of mitochondria was demonstrated in a separate animal by intracoronary injection of iron (II, III) oxide-labeled human cardiac fibroblast mitochondria into the swine LCA (n=1). Serial section immunohistochemistry and Prussian blue co-staining of the swine heart confirmed the presence of human mitochondria in the heart tissue within cardiomyocytes, interstitial spaces, and the vascular walls (FIGS. 11D-11G).

Intracoronary injection of mitochondria and myocardial function. There were no statistical differences between intracoronary injection of vehicle and baseline values for any of the hemodynamic parameters. Intracoronary injection of mitochondria did not affect heart rate, mean arterial pressure, or cardiac rhythm at any concentration of mitochondria tested compared with baseline or vehicle (FIG. 12A). Higher concentrations of mitochondria ($1\times10^9$ and $1\times10^{11}$) significantly enhanced regional and global LV function, as observed by increases in the proportion of LV free-wall segmental shortening ($1\times10^9$ p=0.016 vs. baseline and p=0.015 vs. vehicle; $1\times10^{11}$ p=0.013 vs. baseline and p=0.014 vs. vehicle) and +max dP/dt ($1\times10^9$ p=0.026 vs. baseline and p=0.024 vs. vehicle; $1\times10^{11}$ p<0.001 vs. baseline and p<0.001 vs. vehicle), and by peak LV developed pressure ($1\times10^9$ p=0.034 vs. baseline and p=0.029 vs. vehicle; $1\times10^{11}$ p=0.035 vs. baseline and p=0.028 vs. vehicle) (FIGS. 12B-12E). FIGS. 12A-12E show hemodynamics and left ventricular function after intracoronary injections of mitochondria.

Figure 3D:
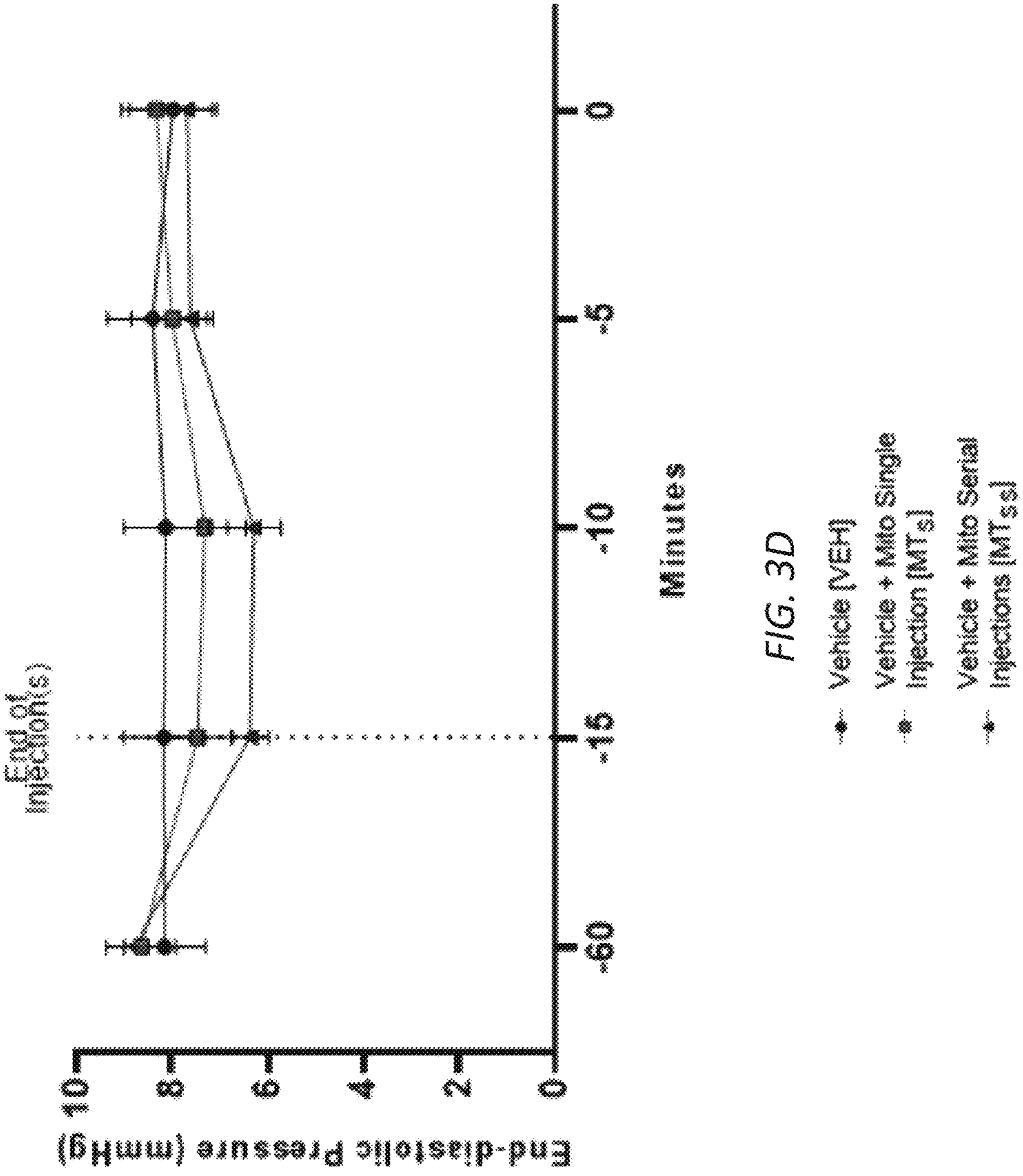
FIG. 3D is a line graph illustrating end diastolic left ventricular pressure following intracoronary injection. All results are shown as mean±SEM for each group. *$P<0.05$ Single Injection vs. Vehicle; #$P<0.05$ Serial Injections vs. Vehicle.
Figure 13C:
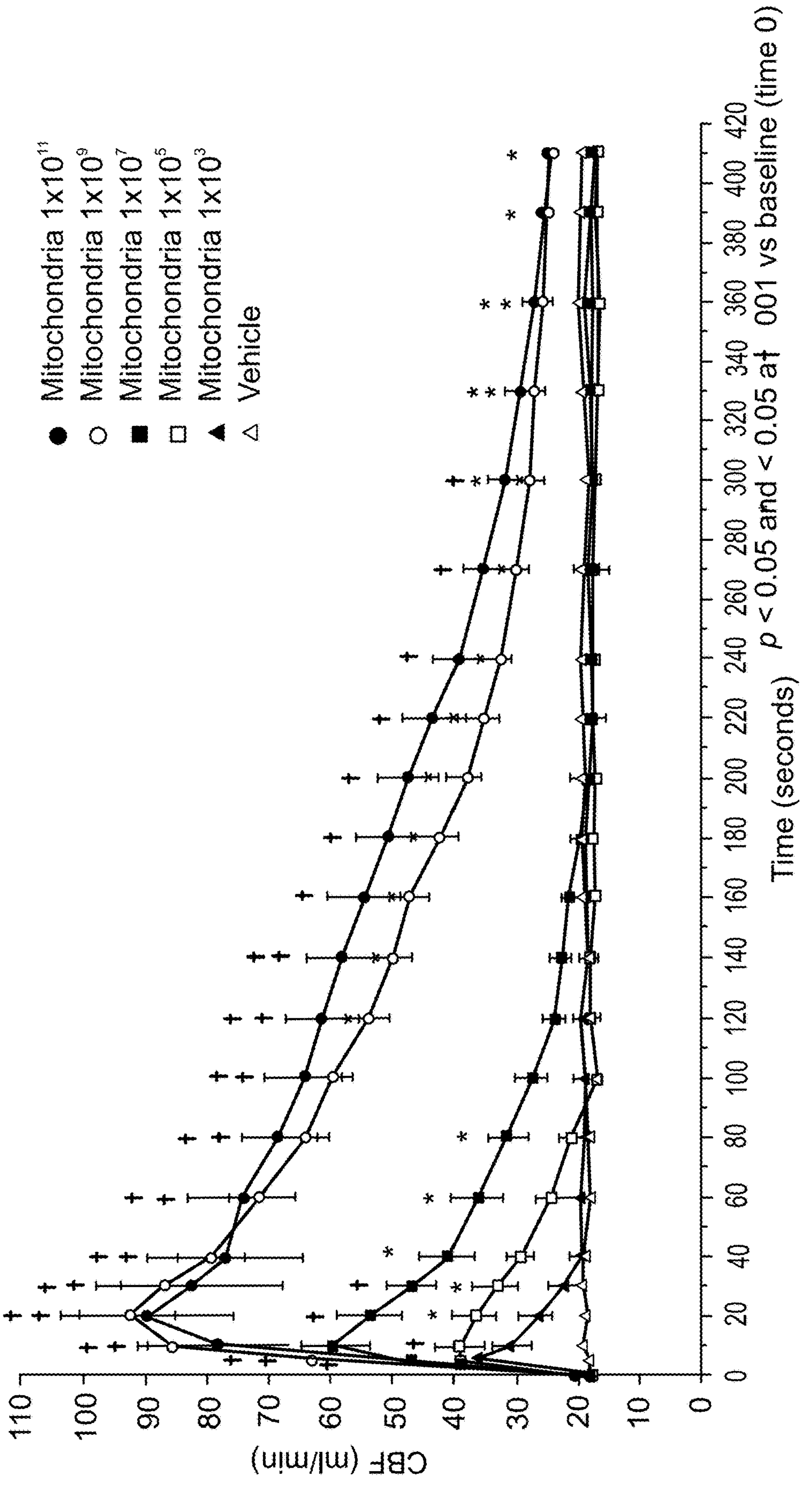
FIG. 13C is a line graph illustrating continuous coronary blood flow (CBF) at the mid left anterior descending artery on intracoronary injection of vehicle and different concentrations of mitochondria (n=6).
Figure 13E:
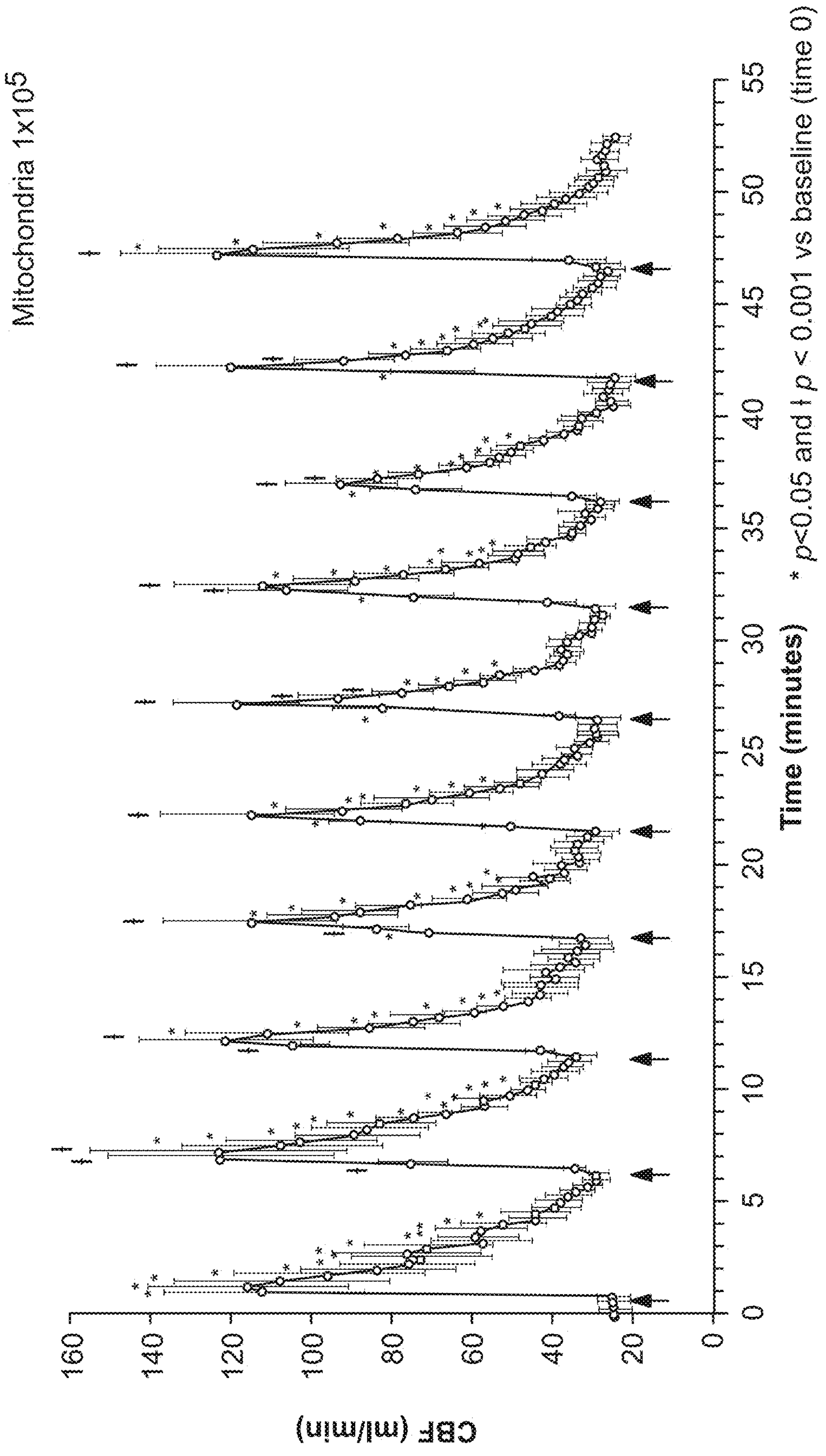
FIG. 13E is a line graph illustrating CBF on serial, intracoronary injections of mitochondria ($1\times10^9$) every 5 min, 10 times. Arrows denote the times of mitochondrial injection. Values are mean±SEM.
Figure 13F:
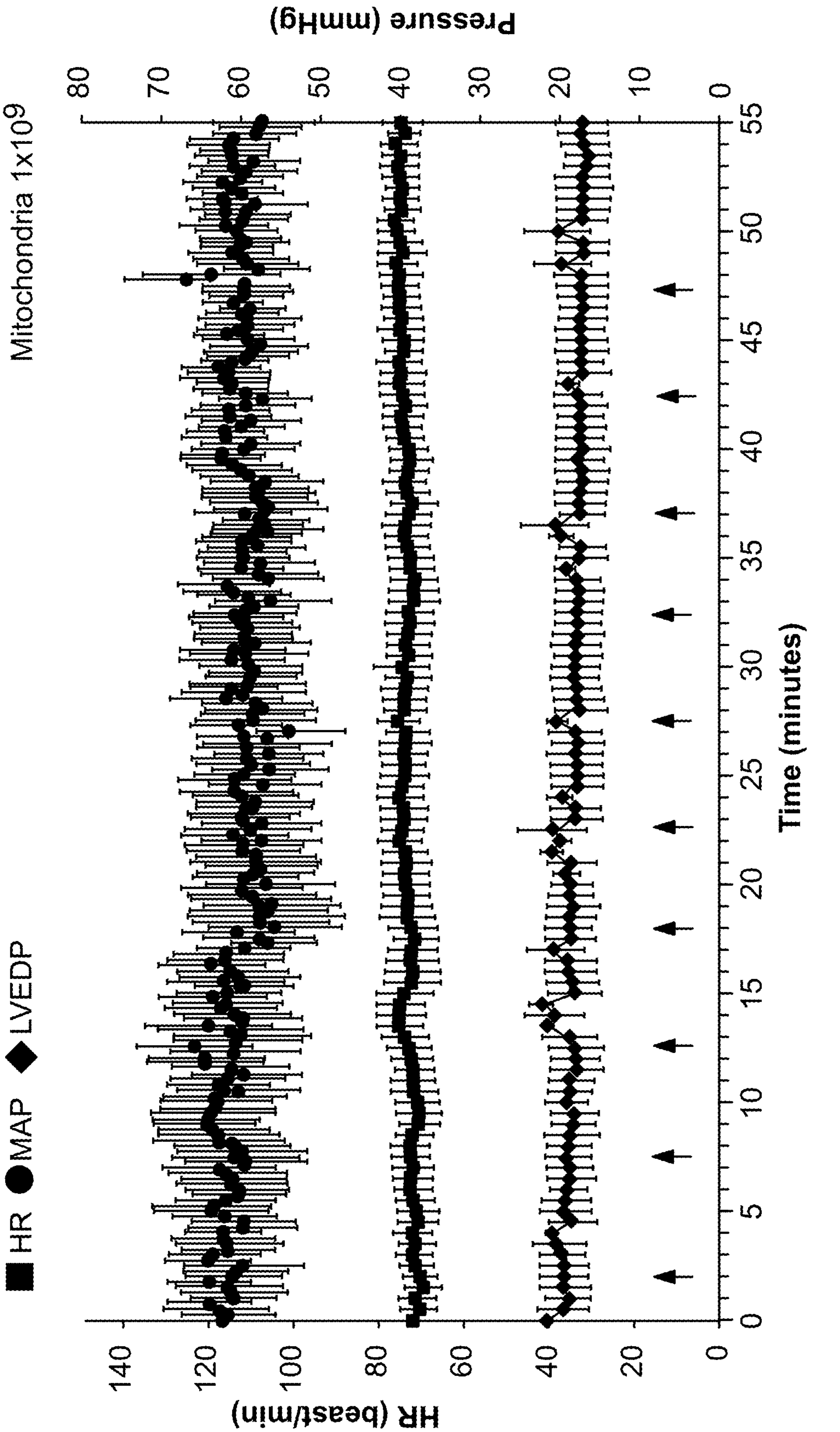
FIG. 13F is a line graph illustrating heart rate, mean arterial pressure, and left ventricular end-diastolic pressure on serial, intracoronary injections of mitochondria ($1\times10^9$) every 5 min, 10 times. Arrows denote the times of mitochondrial injection. Values are mean±SEM. * p<0.05 and † p<0.001 versus baseline (time 0) (n=5). LAD=left anterior descending artery; LCX=left circumflex artery.

Intracoronary injection of mitochondria and CBF. Angiographic analyses showed patent coronary arteries with no detectable lesions or blockages (FIGS. 13A-13B). Mean CBF before mitochondrial injection was 20.5±1.3 ml/min (FIG. 13C). Intracoronary injection of mitochondria increased CBF in a concentration-dependent manner (FIGS. 13C-13D). Analysis of the AUC for CBF showed significant increases in CBF at mitochondrial concentrations of $1\times10^7$ (10.001.7±914.3 ml/min×seconds; p=0.032), $1\times10^9$ (19, 843.7±1,208.4 ml/min×seconds; p<0.001), and $1\times10^{11}$ (18, 262.3±2,131.6 ml/min×seconds; p<0.001) compared with vehicle alone (7,242.9±624.7 ml/min×seconds) (FIG. 3D). Maximum CBF was observed at a mitochondrial concentration of $1\times10^9$, a 325% increase compared with baseline CBF (p<0.001). Increase in CBF was sustained for 6.5±0.6 minutes. No differences were observed in peak CBF (p=0.842) or in the duration of increase (p=0.304) between $1\times10^9$ and $1\times10^{11}$ mitochondria (FIG. 13C-13D). The response of CBF was reproducible with repeated injections of mitochondria ($1\times10^9$), every 5 minutes for 10 repetitions (FIG. 13E). There were no effects on heart rate or mean arterial pressure with either single or serial injections of mitochondria (FIG. 13F). FIGS. 13A-13F shows coronary patency and coronary blood flow.

Intracoronary injection of mitochondria during increased myocardial demand. Intracoronary injection of ADH resulted in coronary vasoconstriction, leading to a significant decrease in CBF (p<0.001) (FIGS. 14A-14B). Intracoronary injection of mitochondria in the ADH-treated coronary artery significantly increased CBF (p<0.001) (FIG. 14B). No changes in heart rate, mean arterial pressure (FIG. 14A), or cardiac rhythm were observed (FIGS. 14A, 14C, and 14D) and no differences in global LV function were detected (FIGS. 14E and 14F). There was a trend toward improved +dP/dt max and LV peak developed pressure when mitochondria were added to ADH compared with ADH alone; however, they did not reach statistical significance. Regional LV function, as measured by the proportion of segmental shortening, showed a modest increase on injection of mitochondria into the vasoconstricted LCA (11.3%±1.5% vs. 8.5%±0.8%; p=0.017) (FIG. 14G). Intracoronary injection of epinephrine produced significant tachycardia and systemic hypertension (FIG. 14A). Mitochondrial injection in the epinephrine-treated coronary artery produced no changes in heart rate, mean arterial pressure, cardiac rhythm, or regional or global LV function (FIGS. 14A-14G). Evaluation of CBF in response to epinephrine with mitochondria was excluded from the analysis because the significant tachycardia and hypertension created by epinephrine causes a secondary increase in CBF and confounds the primary changes in CBF by mitochondria. FIGS. 14A-14G show intracoronary injection of mitochondria during coronary vasoconstriction and tachycardia.

To provide a positive control, a separate study was performed in which polystyrene microbeads (3, 10, and 150 mm, $1\times10^9$ each) were injected separately into the LCA (n=5). The sizes of the microbeads were chosen to exceed the size ranges of mitochondria (0.5-1.0 mm). Intracoronary injection of 3-mm microbeads had no effect on hemodynamics or LV function. In contrast, 10- and 150-mm microbeads, which significantly exceed the size of the injected mitochondria, resulted in significant coronary occlusions and myocardial contractile failure.

PHASE 2: EVALUATION OF INCREASE IN CORONARY BLOOD FLOW. The role of mitochondrial viability and respiration competence. In contrast to intracoronary injection of mitochondria, there was no change in CBF associated with direct injection of mitochondria to the myocardium (FIG. 15A) (n=3). Without being bound by theory, if myocardial oxygen consumption increased, it would also be reflected by the decrease of coronary sinus proportion venous oxygen saturation associated with a compensatory increase in CBF. On the contrary, coronary sinus proportion venous oxygen saturation increased to near arterial levels immediately on intracoronary delivery of mitochondria, from 53.7% 2.4% to 96.1%±1.3% (n=4; p<0.001), concomitant with the increase in CBF (FIG. 15B).

Figure 15D:
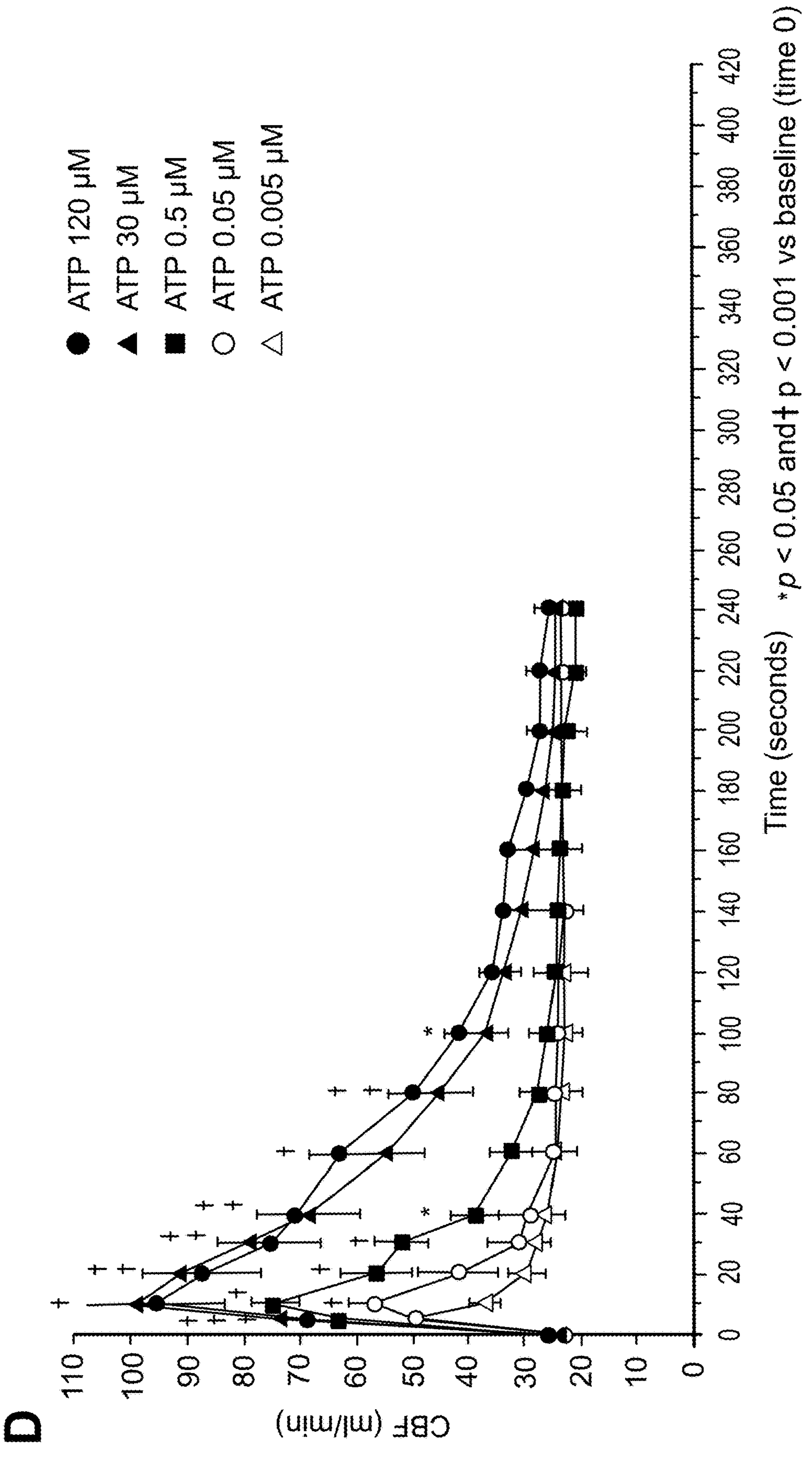
FIG. 15D is a line graph illustrating coronary blood flow on intracoronary injection of ATP alone, as measured in the various concentrations of mitochondria. * $p<0.05$ and † $p<0.001$ versus baseline (time 0) (n=4). ATP=adenosine triphosphate.
Figure 16E:
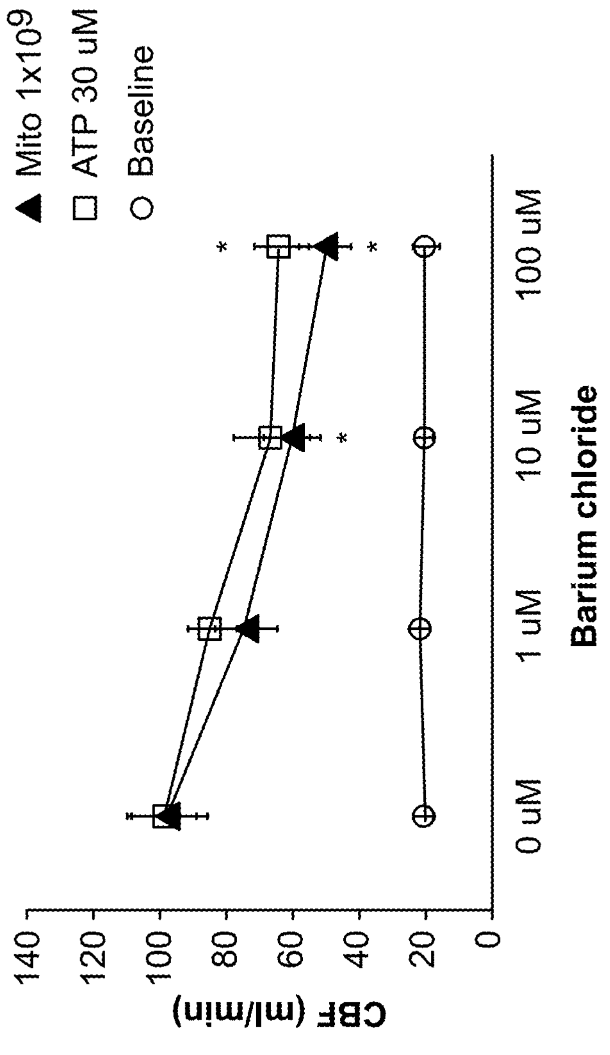
FIG. 16E is a line graph illustrating representative CBF on intracoronary injection of mitochondria after pretreatment with increasing concentrations of $K_{IR}$-channel inhibitor barium chloride. CBF after ATP injection ($K_{IR}$-channel activator, 30 mM) shows positive inhibition of KIR channels (n=4). Values are ±SEM; * $p<0.05$ versus CBF in the absence of inhibitor within the same group.

The role of mitochondrial viability and respiration competence in mitochondria-induced coronary vasodilation was investigated by intracoronary injection of devitalized mitochondria, HeLa and HeLa-$p^0$ mitochondria. FIGS. 15A-15D show coronary blood flow and mitochondrial respiration capacity. Intracoronary injection of devitalized mitochondria ($1\times10^9$) did not alter CBF (n=4) (FIG. 15A). Intracoronary injection of HeLa mitochondria, which are capable of oxidative phosphorylation, increased CBF from 24.6±2.9 ml/min to 79.7±8.1 ml/min (n=6; p<0.001) (FIG. 15A). In contrast, intracoronary injection of HeLa-$p^0$ mitochondria, which are not capable of oxidative phosphorylation, had no effect on CBF (n=6) (HeLa AUC 18,416.5±2,204.4 vs. HeLa-$p^0$ AUC 9,524.27±1,230.1 ml/min×seconds; p=0.005) (FIG. 15A).

The role of ATP. To investigate the role of mitochondrial energy synthesis in coronary vasodilation, ATP content in the previously tested mitochondrial concentrations ($1\times10^3$, $1\times10^5$, $1\times10^7$, $1\times10^9$, and $1\times10^{11}$) was determined and the corresponding doses of ATP alone were injected into the LCA (n=4) (FIG. 15C). Intracoronary injection of ATP in the absence of mitochondria increased CBF similarly to the corresponding concentration of mitochondria (FIG. 15D). However, the duration of hyperemia was significantly shorter than that observed from intracoronary injection of mitochondria. For instance, the injection of $1\times10^9$ mitochondria provided 6.5±0.6 min of increase in CBF versus 3.3±0.2 min when 30 mM of ATP (amount found in $1\times10^9$ mitochondria) was injected alone (p<0.001).

Signaling pathways of coronary vasodilation. Mitochondria-induced increase in CBF was unaffected by the inhibition of endothelium-derived pathways of coronary vasodilation (nitric oxide synthase and cyclooxygenase) (FIGS. 16A and 16B) (n=4 each). Inhibition of the adenosine receptors and inhibition of $K_{ATP}$ channels also had no effect on mitochondria-induced increase in CBF (FIGS. 16C-16E) (n=4 each). In contrast, inhibition of $K_{IR}$ channels significantly attenuated mitochondria-induced increase in CBF from 97.8±11.9 ml/min to 60.1±8.4 ml/min (p=0.018) and to 50.2±7.6 ml/min (p=0.012) at barium chloride concentrations 10 and 100 mM, respectively (FIG. 16E) (n=4). FIGS. 16A-16E illustrate mechanism of mitochondria-induced coronary vasodilation.

PHASE 3: CARDIOPROTECTIVE EFFICACY OF MITOCHONDRIAL TRANSPLANTATION BY INTRACORONARY DELIVERY IN ISCHEMIA-REPERFUSION

INJURY. Animals. There was no significant difference in animal body weight between the mitochondria group and the vehicle-only group (p=0.133). One animal in the vehicle group died of refractory ventricular fibrillation at the onset of reperfusion.

Post-ischemic myocardial function. FIGS. 17A-17G show myocardial function after intracoronary mitochondrial transplantation in regional myocardial IRI. There were no differences in the pre-ischemic vital signs or LV contractility between the 2 groups (FIGS. 17A-17G). With the onset of regional ischemia, significant depressions in LV contractility were observed in both the mitochondria group (n=8) and vehicle-only group (n=7) (FIGS. 17C-17G), but no differences were observed between the groups. During reperfusion, all contractile measures were significantly higher in the mitochondria group (FIGS. 17C-17G) and returned to pre-ischemic levels by the end of the reperfusion period. Similarly, echocardiographic analyses showed superior LV function in the mitochondria group as measured by proportion of LV fractional shortening (23.8%±2.8% vs. 13.9%±1.2%; p=0.004), proportion LV fractional area change (41.8%±2.9% vs. 28.6%±2.3%; p=0.003), and proportion EF (47.9%±4.6% vs. 30.2%±2.3%; p=0.003) at 2 hours of reperfusion (FIGS. 18B-18D).

Figure 18A:
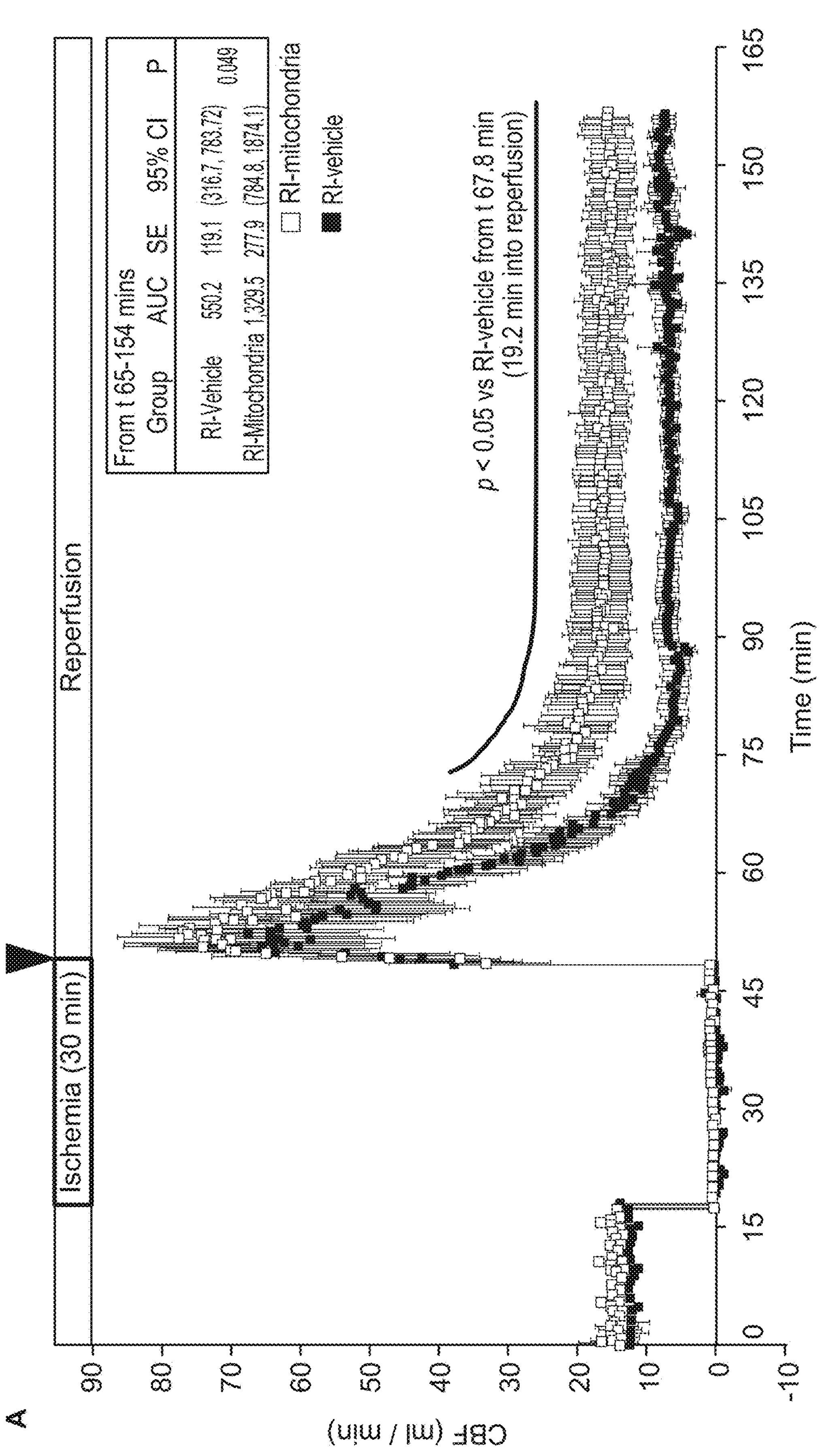
FIG. 18A is a line graph illustrating representative CBF at the left anterior descending artery distal to temporary occlusion in the vehicle group (RI-Vehicle) and mitochondria group (RI-Mito). $p<0.05$ between 2 groups from 67.8 min (19.2 min into reperfusion) to the end of reperfusion (120 min). Areas under the curve are compared between the 2 groups from 65 min after reactive hyperemia, in which mean CBF exhibited a statistically significant difference.

Post-ischemic coronary blood flow. FIGS. 18A-18F show coronary blood flow and tissue survival after intracoronary mitochondrial transplant in regional IRI. The mitochondria group exhibited significantly higher CBF throughout the reperfusion period compared with the vehicle-only group. Pre-ischemic CBF was 13.4±1.9 ml/min and 11.1±2.5 ml/min in the mitochondria group and vehicle-only group, respectively (FIG. 18A) (p=0.462). With the onset of ischemia, CBF decreased to near 0 ml/min in both groups. Immediately on reperfusion, reactive hyperemia was observed in both groups to peak at CBF levels of 76.0±4.5 ml/min in the mitochondria group and 67.4±16.5 ml/min in the vehicle-only group. However, 19.2 minutes post-reperfusion, mean CBF remained significantly higher in the mitochondria group, and this increase was present until the end of the 120-min reperfusion period (AUC 1,329.5±277.9 vs. 550.2±119.1 ml/min×seconds; p=0.042) (FIG. 18A).

Infarct size. There was no difference in the mean area at risk (proportion of LV mass) between the mitochondria group and the vehicle-only group (37.4±1.9 vs. 35.4±2.7; p=0.343). Infarct size (proportion of area at risk) was significantly reduced in the mitochondria group (7.3%±1.1% vs. 38.6%±2.7%; p<0.001) (FIGS. 18E and 18F).

Using $^{18}$F-rhodamine-6G, which specifically labels actively respiring mitochondria, the systemic distribution of mitochondria when delivered via the coronary arteries shows mitochondrial uptake and biodistribution. Positron emission tomographic imaging demonstrated that intracoronary delivery distributed mitochondria specific to the vascular supply of LCA. Minor signal was detected in the descending aorta. The tracer signal was not detected in other organs despite the injection of much higher concentrations of mitochondria than the therapeutic dosage.

According to the results, intracoronary injection of mitochondria at concentrations of $1\times10^3$ to $1\times10^{11}$ has no adverse effects on coronary patency or cardiac function. Mitochondria were also safely injected into severely constricted coronary arteries as well as under hemodynamic stresses of significant tachycardia and hypertension, all of which often accompany various pathologic conditions of the heart. The safety of intracoronary infusion of mitochondria is further corroborated by adverse response to intracoronary injection of microbeads (10 and 150 mm) that are larger than the diameters of the small and midsize coronary arterioles of swine (Kassab G S, Rider C A, Tang N J, Fung Y C. Morphometry of pig coronary arterial trees. Am J Physiol 1993; 265:H350-65.), resulting in significant coronary occlusion, arrhythmia, and contractile failure, none of which were observed with intracoronary injections of mitochondria.

This is the first data to show that intracoronary infusion of mitochondria significantly increases CBF. This effect on CBF was immediate and concentration dependent, with maximal hyperemia achieved by intracoronary injection of $1\times10^9$ mitochondria. The duration of hyperemia by mitochondria (6.5±0.6 min) is significantly higher than that of many of the mainstream pharmacologic coronary vasodilators such as papaverine (~50 s) and adenosine (~20 s) (Layland J, Carrick D, Lee M, Oldroyd K, Berry C. Adenosine: physiology, pharmacology, and clinical applications. J Am Coll Cardiol Intv 2014; 6:581-91), and the hyperemia was safely extendable by serial injections. Furthermore, intracoronary injection of mitochondria was able to entirely reverse the vasoconstrictions induced by a potent coronary vasoconstrictor.

The results show that ATP is partly responsible for mitochondria-induced hyperemia. The observed increase in CBF was achievable through the delivery of intact, respiration-competent mitochondria. Mitochondria-induced hyperemia was attenuated only by the inhibition of the $K_{IR}$ channels and unaffected by the inhibition of nitric oxide synthase, cyclooxygenase, or adenosine receptor. The inhibition of $K_{IR}$ channels partly abolished the vasodilatory effect by mitochondria.

CBF in response to intracoronary injection of ATP alone paralleled that of the corresponding mitochondrial concentrations in the magnitude of increase in CBF; however, the durations of hyperemia were significantly shorter. One possible explanation for these findings may be related to the short half-life of exogenous ATP in blood (0.5 to 1.5 s) (Shapiro M J, Jellinek M, Pyrros D, Sundine M, Baue A E. Clearance and maintenance of blood nucleotide levels with adenosine triphosphatemagnesium chloride injection. Circ Shock 1992; 36:62-7), rendering it undesirable for clinical application (Skrabanja A T, Bouman E A, Dagnelie P C. Potential value of adenosine 5'-triphosphate (ATP) and adenosine in anesthesia and intensive care medicine. Br J Anaesth 2005; 94:556-62). Intact mitochondria with active electron transport chain and ATP synthesis may continuously renew ATP as they are infused in the coronary arteries, leading to the prolongation of the vasodilatory effect of ATP.

The results demonstrate strong cardioprotective efficacy of intracoronary mitochondrial transplantation in myocardial ischemia-reperfusion injury by improving post-ischemic function, perfusion, and infarct size. We used a model of temporary coronary occlusion followed by mitochondrial injection at reperfusion because, in current practice, most patients with acute myocardial ischemia undergo reperfusion by emergency coronary catheterization, which would also be an opportune time to administer mitochondria.

The results also show that the increase in post-ischemic CBF was sustained throughout the 120 min of reperfusion in the mitochondria hearts compared with vehicle hearts. The increase in CBF is an advantageous phenomenon unique to intracoronary injection and absent when mitochondria are directly injected into the heart muscle. The presence of a primary cardioprotective process at the level of the tissue that is separate and successive to the improved CBF after intracoronary infusion of mitochondria. These data show that intracoronary delivery of mitochondria lead to increase in the ATP content of the recipient tissue, upregulation of proteomic pathways for the mitochondrion and precursor metabolites, reduction of inflammatory mediators, upregulation of antiapoptotic markers, and replenishment of damaged mitochondrial deoxyribonucleic acid.

In the setting of ischemia-reperfusion, mitochondria resulted in a post-peak CBF that was higher throughout the entire reperfusion period compared with a transient effect of approximately 7 min in the nonischemic hearts. The biochemical milieu of the ischemic heart is markedly different from that of the normal heart. Intracoronary delivery of mitochondria offers the dual benefit of counteracting impaired tissue perfusion at the level of the coronary arteries and rescuing metabolic and inflammatory pathways at the tissue level. The rescue of cardiomyocytes from both approaches may further reduce the production of various vasoconstrictive signals, producing a synergistic and cascading improvement to CBF, myocardial function, and infarct size.

Intracoronary use of mitochondria provides a variety of possible applications for both angiographic and surgical therapies by exploiting its multifactorial rescue of myocellular damage, coronary vasodilation, and the versatility of the minimally invasive catheter-based delivery. Mitochondria can be effectively delivered by bolus injections to the heart by rapid continuous-flow infusions rather than by the stop-reflow technique, which involves the temporal coronary occlusions used during certain cell therapies such as mesenchymal stem cells, which carry the risk of arrhythmia and myocardial injury (Grieve S M, Bhindi R, Seow J, et al. Microvascular obstruction by intracoronary delivery of mesenchymal stem cells and quantification of resulting myocardial infarction by cardiac magnetic resonance. Circ Heart Fail 2010; 3:e5-6).

In conclusion, mitochondrial transplantation by intracoronary delivery to the myocardium is safe and efficacious, with strong vasodilatory capacity, which translates to significant therapeutic efficacy in treating myocardial ischemia-reperfusion injury. The capacities of metabolic restoration, cardiomyocyte salvage, and coronary vasodilation may be harnessed to produce therapeutic synergy, with the present findings serving as a preclinical platform to help optimize human application across the clinical spectrum of ischemic heart disease and coronary regulation.

Example 7: MT Protects Lung, Liver, Pancreas, and Prostate from IRI-associated Damage Experiments are performed to show that mitochondria delivered to the lung, liver, pancreas and prostate protects it from structural and/or functional loss due to IRI.

In some studies, experiments are performed to show that mitochondria (e.g., delivered by vascular infusion through the pulmonary artery or a nebulizer) can protect the lung from IRI associated loss of global function and/or regional function.

In some studies, the middle and inferior lobes of the right lung in mice are clamped for 1 h (middle) and 2 h (inferior) of ischemia. Prior to ischemia, mice are treated with buffer or with isolated mitochondria. The mice will be evaluated 48 h after reperfusion. It is expected that the mitochondria can preserve lung structure and function following IRI. In some other experiments, mice can also be anesthetized and ventilated. The left hilar structure can be clamped for 2 h. Buffer or 3 cc (cubic centimeter) of mitochondria solution can be injected to the left pulmonary artery, and the mice can be sacrificed the next day. It is expected that the delivery of mitochondria can reduce IRI injury in the left lung.

It is expected that mitochondria can be used to prevent or alleviate loss of function in lungs damaged by ischemia, reperfusion, IRI, smoke, or toxins, and MT can be used to preserve lung structure and function for use in lung transplantation and surgery.

In some cases, experiments are performed to show that mitochondria delivered by vascular infusion through the hepatic portal vein protects the liver from IRI associated loss of global function and/or regional function. Results from these experiments will demonstrate that mitochondria can be used to prevent or alleviate loss of function in a liver damaged by ischemia, reperfusion, or IRI. These results will also demonstrate MT can used to preserve liver structure and function for use in liver transplantation and surgery.

Experiments can also be performed to show that mitochondria delivered by vascular infusion through the greater pancreatic artery protects the pancreas from IRI associated loss of global function and/or regional function. It is expected that mitochondria can be used to prevent or alleviate loss of function in a pancreas damaged by ischemia, reperfusion, or IRI. These results will also demonstrate MT can used to preserve pancreas structure and function for use in pancreas transplantation and surgery.

Experiments can be performed to show that mitochondria delivered by vascular infusion through the prostate artery protects the prostate from IRI associated loss of global function and/or regional function. Results from these experiments will demonstrate that mitochondria can be used to prevent or alleviate loss of function in a prostate damaged by ischemia, reperfusion, or IRI. These results will also demonstrate MT can used to preserve prostate structure and function for use in prostate transplantation and surgery.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing risk of ischemia-reperfusion injury (IRI) in a subject, comprising:

identifying a subject at risk for IRI; and administering to the subject a therapeutically effective amount of a composition comprising isolated mitochondria and/or a combined mitochondrial agent, wherein the composition is administered to the subject prior to ischemia or an ischemic event.

2. A method of preventing or treating cell damage, tissue damage, and/or organ damage associated with IRI in a subject, comprising:

identifying the subject at risk for, or having, cell damage, tissue damage, and/or organ damage associated with IRI; and administering to the subject a therapeutically effective amount of a composition comprising isolated mitochondria and/or a combined mitochondrial agent, wherein the composition is administered prior to ischemia or an ischemic event.

3. The method of claim 1, wherein a subject has an ischemia-related disease, a mitochondrial dysfunction disorder, or a metabolic disorder.

4. The method of claim 1, wherein the composition is administered to the subject by injecting the composition into a blood vessel of the subject.

5. The method of claim 1, wherein the composition is administered to a tissue or an organ by direct injection.

6. The method of claim 5, wherein the organ is selected from the following: heart, kidney, lung, skin, eye, liver, pancreas, lung, or prostate.

7. The method of claim 1, wherein administering is performed by intravenous, intra-articular, subcutaneous, intraperitoneal, intramuscular, intradermal, or intracardiac injection.

8. The method of claim 1, wherein the subject is administered a single dose of the composition or wherein the subject is administered multiple doses of the composition.

9. The method of claim 1, wherein the mitochondria are autogeneic, allogeneic, or xenogeneic.

10. The method of claim 1, further comprising, prior to the administering step, a step of collecting the isolated mitochondria from cells, and wherein the administering step includes administering the isolated mitochondria to the subject immediately after the isolated mitochondria are collected from cells.

11. The method of claim 1, wherein the composition comprises at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ mitochondria and/or combined mitochondrial agents.

12. The method of claim 1, wherein the ischemic event or the ischemic injury is associated with a medical procedure.

13. The method of claim 2, wherein a subject has an ischemia-related disease, a mitochondrial dysfunction disorder, or a metabolic disorder.

14. The method of claim 2, wherein the composition is administered to the subject by injecting the composition into a blood vessel of the subject, or wherein the composition is administered to a tissue or an organ by direct injection.

15. The method of claim 14, wherein the organ is selected from the following: heart, kidney, lung, skin, eye, liver, pancreas, lung, or prostate.

16. The method of claim 2, wherein administering is performed by intravenous, intra-articular, subcutaneous, intraperitoneal, intramuscular, intradermal, or intracardiac injection.

* * * * *